(12) United States Patent
Holcomb et al.

(10) Patent No.: US 8,409,200 B2
(45) Date of Patent: Apr. 2, 2013

(54) SURGICAL GRASPING DEVICE

(75) Inventors: Matthew D. Holcomb, Lebanon, OH (US); James T. Spivey, Cincinnati, OH (US); Omar J. Vakharia, Cincinnati, OH (US); Frederick Q. Johnson, Pleasanton, CA (US); Surag S. Mantri, Sunnyvale, CA (US); Hoang V. Nguyen, San Jose, CA (US); Steven P. Woodard, Cupertino, CA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1244 days.

(21) Appl. No.: 12/203,330

(22) Filed: Sep. 3, 2008

(65) Prior Publication Data

US 2010/0057085 A1 Mar. 4, 2010

(51) Int. Cl.
*A61B 18/18* (2006.01)
(52) U.S. Cl. .......................................... 606/51
(58) Field of Classification Search ............ 606/61, 606/41–52
See application file for complete search history.

(56) References Cited

U.S. PATENT DOCUMENTS

| | | | |
|---|---|---|---|
| 645,576 A | 3/1900 | Tesla | |
| 649,621 A | 5/1900 | Tesla | |
| 787,412 A | 4/1905 | Tesla | |
| 1,127,948 A | 2/1915 | Wappler | |
| 1,482,653 A | 2/1924 | Lilly | |
| 1,625,602 A | 4/1927 | Gould et al. | |
| 1,916,722 A | 7/1933 | Ende | |
| 2,028,635 A | 1/1936 | Wappler | |
| 2,031,682 A | 2/1936 | Wappler et al. | |
| 2,113,246 A | 4/1938 | Wappler | |
| 2,155,365 A | 4/1939 | Rankin | |
| 2,191,858 A | 2/1940 | Moore | |
| 2,196,620 A | 4/1940 | Attarian | |
| 2,388,137 A | 10/1945 | Graumlich | |
| 2,493,108 A | 1/1950 | Casey, Jr. | |
| 2,504,152 A | 4/1950 | Riker et al. | |
| 2,938,382 A | 5/1960 | De Graaf | |
| 2,952,206 A | 9/1960 | Becksted | |
| 3,069,195 A | 12/1962 | Buck | |
| 3,070,088 A | 12/1962 | Brahos | |
| 3,170,471 A | 2/1965 | Schnitzer | |

(Continued)

FOREIGN PATENT DOCUMENTS

| AU | 666310 B2 | 2/1996 |
|---|---|---|
| DE | 3008120 A1 | 9/1980 |

(Continued)

OTHER PUBLICATIONS

International Search Report for PCT/US2009/055140, Mar. 23, 2010 (9 pages).

(Continued)

*Primary Examiner* — Nicholas Lucchesi
*Assistant Examiner* — Jenna Zhang

(57) ABSTRACT

A surgical device comprising a clevis defining a longitudinal axis and a jaw comprising a first member and a second member. A slider is slidably engaged to the clevis, the slider comprising a pin. The pin is receiveably engaged in the first slot and the jaw is selectively moveable between a first position and a second position through longitudinal movement of the slider. In various embodiments, the first and second members are movable between an angular open position, a parallel open position, and a parallel closed position.

26 Claims, 36 Drawing Sheets

U.S. PATENT DOCUMENTS

| | | |
|---|---|---|
| 3,435,824 A | 4/1969 | Gamponia |
| 3,470,876 A | 10/1969 | Barchilon |
| 3,595,239 A | 7/1971 | Petersen |
| 3,669,487 A | 6/1972 | Roberts et al. |
| 3,746,881 A | 7/1973 | Fitch et al. |
| 3,799,672 A | 3/1974 | Vurek |
| 3,854,473 A | 12/1974 | Matsuo |
| 3,946,740 A | 3/1976 | Bassett |
| 3,948,251 A | 4/1976 | Hosono |
| 3,994,301 A | 11/1976 | Agris |
| 4,011,872 A | 3/1977 | Komiya |
| 4,012,812 A | 3/1977 | Black |
| 4,085,743 A | 4/1978 | Yoon |
| 4,164,225 A | 8/1979 | Johnson et al. |
| 4,174,715 A | 11/1979 | Hasson |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,269,174 A | 5/1981 | Adair |
| 4,278,077 A | 7/1981 | Mizumoto |
| 4,285,344 A | 8/1981 | Marshall |
| 4,311,143 A | 1/1982 | Komiya |
| 4,329,980 A | 5/1982 | Terada |
| 4,396,021 A | 8/1983 | Baumgartner |
| 4,406,656 A | 9/1983 | Hattler et al. |
| 4,452,246 A | 6/1984 | Bader et al. |
| 4,461,281 A | 7/1984 | Carson |
| 4,491,132 A | 1/1985 | Aikins |
| 4,527,331 A | 7/1985 | Lasner et al. |
| 4,527,564 A | 7/1985 | Eguchi et al. |
| 4,538,594 A | 9/1985 | Boebel et al. |
| D281,104 S | 10/1985 | Davison |
| 4,569,347 A | 2/1986 | Frisbie |
| 4,580,551 A | 4/1986 | Siegmund et al. |
| 4,646,722 A | 3/1987 | Silverstein et al. |
| 4,653,476 A | 3/1987 | Bonnet |
| 4,655,219 A | 4/1987 | Petruzzi |
| 4,669,470 A | 6/1987 | Brandfield |
| 4,671,477 A | 6/1987 | Cullen |
| 4,685,447 A | 8/1987 | Iversen et al. |
| 4,711,240 A | 12/1987 | Goldwasser et al. |
| 4,712,545 A | 12/1987 | Honkanen |
| 4,721,116 A | 1/1988 | Schintgen et al. |
| 4,733,662 A | 3/1988 | DeSatnick et al. |
| D295,894 S | 5/1988 | Sharkany et al. |
| 4,763,669 A | 8/1988 | Jaeger |
| 4,770,188 A | 9/1988 | Chikama |
| 4,815,450 A | 3/1989 | Patel |
| 4,823,794 A | 4/1989 | Pierce |
| 4,829,999 A | 5/1989 | Auth |
| 4,867,140 A | 9/1989 | Hovis et al. |
| 4,869,238 A | 9/1989 | Opie et al. |
| 4,869,459 A | 9/1989 | Bourne |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,950,285 A | 8/1990 | Wilk |
| 4,960,133 A | 10/1990 | Hewson |
| 4,977,887 A | 12/1990 | Gouda |
| 4,979,950 A | 12/1990 | Transue et al. |
| 4,984,581 A | 1/1991 | Stice |
| 4,994,079 A | 2/1991 | Genese et al. |
| 5,007,917 A | 4/1991 | Evans |
| 5,010,876 A | 4/1991 | Henley et al. |
| 5,020,514 A | 6/1991 | Heckele |
| 5,020,535 A | 6/1991 | Parker et al. |
| 5,025,778 A | 6/1991 | Silverstein et al. |
| 5,033,169 A | 7/1991 | Bindon |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,052,372 A | 10/1991 | Shapiro |
| 5,065,516 A | 11/1991 | Dulebohn |
| 5,066,295 A | 11/1991 | Kozak et al. |
| 5,123,913 A | 6/1992 | Wilk et al. |
| 5,123,914 A | 6/1992 | Cope |
| 5,133,727 A | 7/1992 | Bales et al. |
| 5,147,374 A | 9/1992 | Fernandez |
| 5,174,300 A | 12/1992 | Bales et al. |
| 5,176,126 A | 1/1993 | Chikama |
| 5,190,050 A | 3/1993 | Nitzsche |
| 5,190,555 A | 3/1993 | Wetter et al. |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,217,003 A | 6/1993 | Wilk |
| 5,217,453 A | 6/1993 | Wilk |
| 5,219,357 A | 6/1993 | Honkanen et al. |
| 5,219,358 A | 6/1993 | Bendel et al. |
| 5,222,362 A | 6/1993 | Maus et al. |
| 5,222,965 A | 6/1993 | Haughton |
| 5,234,437 A | 8/1993 | Sepetka |
| 5,234,453 A | 8/1993 | Smith et al. |
| 5,235,964 A | 8/1993 | Abenaim |
| 5,242,456 A | 9/1993 | Nash et al. |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,284,162 A | 2/1994 | Wilk |
| 5,287,845 A | 2/1994 | Faul et al. |
| 5,287,852 A | 2/1994 | Arkinstall |
| 5,290,299 A | 3/1994 | Fain et al. |
| 5,290,302 A | 3/1994 | Pericic |
| 5,295,977 A | 3/1994 | Cohen et al. |
| 5,297,536 A | 3/1994 | Wilk |
| 5,301,061 A | 4/1994 | Nakada et al. |
| 5,312,333 A | 5/1994 | Churinetz et al. |
| 5,312,351 A | 5/1994 | Gerrone |
| 5,312,416 A | 5/1994 | Spaeth et al. |
| 5,312,423 A | 5/1994 | Rosenbluth et al. |
| 5,318,589 A | 6/1994 | Lichtman |
| 5,320,636 A | 6/1994 | Slater |
| 5,324,261 A | 6/1994 | Amundson et al. |
| 5,325,845 A | 7/1994 | Adair |
| 5,330,471 A | 7/1994 | Eggers |
| 5,330,486 A | 7/1994 | Wilk |
| 5,330,488 A | 7/1994 | Goldrath |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,302 A | 10/1994 | Ko |
| 5,354,311 A | 10/1994 | Kambin et al. |
| 5,356,381 A | 10/1994 | Ensminger et al. |
| 5,356,408 A | 10/1994 | Rydell |
| 5,364,408 A | 11/1994 | Gordon |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,370,647 A | 12/1994 | Graber et al. |
| 5,370,679 A | 12/1994 | Atlee, III |
| 5,374,273 A | 12/1994 | Nakao et al. |
| 5,374,275 A | 12/1994 | Bradley et al. |
| 5,374,277 A | 12/1994 | Hassler |
| 5,377,695 A | 1/1995 | An Haack |
| 5,383,877 A | 1/1995 | Clarke |
| 5,383,888 A | 1/1995 | Zvenyatsky et al. |
| 5,386,817 A | 2/1995 | Jones |
| 5,391,174 A | 2/1995 | Weston |
| 5,392,789 A | 2/1995 | Slater et al. |
| 5,395,386 A | 3/1995 | Slater |

| Patent | Date | Name |
|---|---|---|
| 5,401,248 A | 3/1995 | Bencini |
| 5,403,328 A | 4/1995 | Shallman |
| 5,403,342 A | 4/1995 | Tovey et al. |
| 5,403,348 A | 4/1995 | Bonutti |
| 5,405,073 A | 4/1995 | Porter |
| 5,405,359 A | 4/1995 | Pierce |
| 5,409,478 A | 4/1995 | Gerry et al. |
| 5,417,699 A | 5/1995 | Klein et al. |
| 5,423,821 A | 6/1995 | Pasque |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,441,499 A | 8/1995 | Fritzsch |
| 5,443,463 A | 8/1995 | Stern et al. |
| 5,445,638 A | 8/1995 | Rydell et al. |
| 5,449,021 A | 9/1995 | Chikama |
| 5,454,827 A | 10/1995 | Aust et al. |
| 5,456,667 A | 10/1995 | Ham et al. |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,460,629 A | 10/1995 | Shlain et al. |
| 5,462,561 A | 10/1995 | Voda |
| 5,465,731 A | 11/1995 | Bell et al. |
| 5,467,763 A | 11/1995 | McMahon et al. |
| 5,468,250 A | 11/1995 | Paraschac et al. |
| 5,470,308 A | 11/1995 | Edwards et al. |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,990 A | 3/1996 | Schülken et al. |
| 5,499,992 A | 3/1996 | Meade et al. |
| 5,501,692 A | 3/1996 | Riza |
| 5,503,616 A | 4/1996 | Jones |
| 5,505,686 A | 4/1996 | Willis et al. |
| 5,507,755 A | 4/1996 | Gresl et al. |
| 5,511,564 A | 4/1996 | Wilk |
| 5,514,157 A | 5/1996 | Nicholas et al. |
| 5,518,501 A | 5/1996 | Oneda et al. |
| 5,522,829 A | 6/1996 | Michalos |
| 5,522,830 A | 6/1996 | Aranyi |
| 5,527,321 A | 6/1996 | Hinchliffe |
| 5,536,248 A | 7/1996 | Weaver et al. |
| 5,538,509 A | 7/1996 | Dunlap et al. |
| 5,540,648 A | 7/1996 | Yoon |
| 5,554,151 A | 9/1996 | Hinchliffe |
| 5,555,883 A | 9/1996 | Avitall |
| 5,558,133 A | 9/1996 | Bortoli et al. |
| 5,562,693 A | 10/1996 | Devlin et al. |
| 5,569,243 A | 10/1996 | Kortenbach et al. |
| 5,569,298 A | 10/1996 | Schnell |
| 5,573,540 A | 11/1996 | Yoon |
| 5,578,030 A | 11/1996 | Levin |
| 5,582,611 A | 12/1996 | Tsuruta et al. |
| 5,582,617 A | 12/1996 | Klieman et al. |
| 5,584,845 A | 12/1996 | Hart |
| 5,591,179 A | 1/1997 | Edelstein |
| 5,593,420 A | 1/1997 | Eubanks, Jr. et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A | 3/1997 | Edwards et al. |
| 5,607,406 A | 3/1997 | Hernandez et al. |
| 5,607,450 A | 3/1997 | Zvenyatsky et al. |
| 5,613,975 A | 3/1997 | Christy |
| 5,618,303 A | 4/1997 | Marlow et al. |
| 5,620,415 A | 4/1997 | Lucey et al. |
| 5,624,399 A | 4/1997 | Ackerman |
| 5,624,431 A | 4/1997 | Gerry et al. |
| 5,626,578 A | 5/1997 | Tihon |
| 5,628,732 A | 5/1997 | Antoon, Jr. et al. |
| 5,630,782 A | 5/1997 | Adair |
| 5,643,283 A | 7/1997 | Younker |
| 5,643,292 A | 7/1997 | Hart |
| 5,643,294 A * | 7/1997 | Tovey et al. .................. 606/148 |
| 5,644,798 A | 7/1997 | Shah |
| 5,645,083 A | 7/1997 | Essig et al. |
| 5,645,565 A | 7/1997 | Rudd et al. |
| 5,649,372 A | 7/1997 | Souza |
| 5,653,677 A | 8/1997 | Okada et al. |
| 5,653,690 A | 8/1997 | Booth et al. |
| 5,653,722 A | 8/1997 | Kieturakis |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,690,606 A | 11/1997 | Slotman |
| 5,690,656 A | 11/1997 | Cope et al. |
| 5,690,660 A | 11/1997 | Kauker et al. |
| 5,695,448 A | 12/1997 | Kimura et al. |
| 5,695,505 A | 12/1997 | Yoon |
| 5,695,511 A | 12/1997 | Cano et al. |
| 5,700,275 A | 12/1997 | Bell et al. |
| 5,702,438 A | 12/1997 | Avitall |
| 5,704,892 A | 1/1998 | Adair |
| 5,709,708 A | 1/1998 | Thal |
| 5,716,326 A | 2/1998 | Dannan |
| 5,730,740 A | 3/1998 | Wales et al. |
| 5,735,849 A | 4/1998 | Baden et al. |
| 5,741,234 A | 4/1998 | Aboul-Hosn |
| 5,741,278 A | 4/1998 | Stevens |
| 5,741,285 A | 4/1998 | McBrayer et al. |
| 5,741,429 A | 4/1998 | Donadio, III et al. |
| 5,746,759 A | 5/1998 | Meade et al. |
| 5,749,826 A | 5/1998 | Faulkner |
| 5,749,881 A | 5/1998 | Sackier et al. |
| 5,749,889 A | 5/1998 | Bacich et al. |
| 5,752,951 A | 5/1998 | Yanik |
| 5,755,731 A | 5/1998 | Grinberg |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |
| 5,779,727 A | 7/1998 | Orejola |
| 5,782,859 A | 7/1998 | Nicholas et al. |
| 5,782,861 A | 7/1998 | Cragg et al. |
| 5,782,866 A | 7/1998 | Wenstrom, Jr. |
| 5,791,022 A | 8/1998 | Bohman |
| 5,792,113 A | 8/1998 | Kramer et al. |
| 5,792,153 A | 8/1998 | Swain et al. |
| 5,792,165 A | 8/1998 | Klieman et al. |
| 5,797,835 A | 8/1998 | Green |
| 5,797,928 A | 8/1998 | Kogasaka |
| 5,797,939 A | 8/1998 | Yoon |
| 5,797,941 A | 8/1998 | Schulze et al. |
| 5,803,903 A | 9/1998 | Athas et al. |
| 5,808,665 A | 9/1998 | Green |
| 5,810,806 A | 9/1998 | Ritchart et al. |
| 5,810,849 A | 9/1998 | Kontos |
| 5,810,865 A | 9/1998 | Koscher et al. |
| 5,810,876 A | 9/1998 | Kelleher |
| 5,810,877 A | 9/1998 | Roth et al. |
| 5,813,976 A | 9/1998 | Filipi et al. |
| 5,814,058 A | 9/1998 | Carlson et al. |
| 5,817,061 A | 10/1998 | Goodwin et al. |
| 5,817,107 A | 10/1998 | Schaller |
| 5,817,119 A | 10/1998 | Klieman et al. |
| 5,819,736 A | 10/1998 | Avny et al. |
| 5,823,947 A | 10/1998 | Yoon et al. |
| 5,824,071 A | 10/1998 | Nelson et al. |
| 5,827,281 A | 10/1998 | Levin |
| 5,827,299 A | 10/1998 | Thomason et al. |
| 5,830,231 A | 11/1998 | Geiges, Jr. |
| 5,833,700 A | 11/1998 | Fogelberg et al. |
| 5,833,703 A | 11/1998 | Manushakian |
| 5,843,017 A | 12/1998 | Yoon |
| 5,843,121 A | 12/1998 | Yoon |

| | | | | | | |
|---|---|---|---|---|---|---|
| 5,849,022 A | 12/1998 | Sakashita et al. | | 6,106,473 A | 8/2000 | Violante et al. |
| 5,853,374 A | 12/1998 | Hart et al. | | 6,109,852 A | 8/2000 | Shahinpoor et al. |
| 5,855,585 A | 1/1999 | Kontos | | 6,110,154 A | 8/2000 | Shimomura et al. |
| 5,860,913 A | 1/1999 | Yamaya et al. | | 6,110,183 A | 8/2000 | Cope |
| 5,860,995 A | 1/1999 | Berkelaar | | 6,113,593 A | 9/2000 | Tu et al. |
| 5,868,762 A | 2/1999 | Cragg et al. | | 6,117,144 A | 9/2000 | Nobles et al. |
| 5,876,411 A | 3/1999 | Kontos | | 6,117,158 A | 9/2000 | Measamer et al. |
| 5,882,331 A | 3/1999 | Sasaki | | 6,139,555 A | 10/2000 | Hart et al. |
| 5,882,344 A | 3/1999 | Stouder, Jr. | | 6,141,037 A | 10/2000 | Upton et al. |
| 5,893,846 A | 4/1999 | Bales et al. | | 6,146,391 A | 11/2000 | Cigaina |
| 5,893,874 A | 4/1999 | Bourque et al. | | 6,148,222 A | 11/2000 | Ramsey, III |
| 5,893,875 A | 4/1999 | O'Connor et al. | | 6,149,653 A | 11/2000 | Deslauriers |
| 5,897,487 A | 4/1999 | Ouchi | | 6,149,662 A | 11/2000 | Pugliesi et al. |
| 5,899,919 A | 5/1999 | Eubanks, Jr. et al. | | 6,156,006 A | 12/2000 | Brosens et al. |
| 5,902,254 A | 5/1999 | Magram | | 6,159,200 A | 12/2000 | Verdura et al. |
| 5,904,702 A | 5/1999 | Ek et al. | | 6,165,184 A | 12/2000 | Verdura et al. |
| 5,908,420 A | 6/1999 | Parins et al. | | 6,168,570 B1 | 1/2001 | Ferrera |
| 5,908,429 A | 6/1999 | Yoon | | 6,168,605 B1 | 1/2001 | Measamer et al. |
| 5,911,737 A | 6/1999 | Lee et al. | | 6,170,130 B1 | 1/2001 | Hamilton et al. |
| 5,916,146 A | 6/1999 | Allotta et al. | | 6,179,776 B1 | 1/2001 | Adams et al. |
| 5,916,147 A | 6/1999 | Boury | | 6,179,837 B1 | 1/2001 | Hooven |
| 5,921,993 A | 7/1999 | Yoon | | 6,183,420 B1 | 2/2001 | Douk et al. |
| 5,921,997 A | 7/1999 | Fogelberg et al. | | 6,190,353 B1 | 2/2001 | Makower et al. |
| 5,922,008 A | 7/1999 | Gimpelson | | 6,190,384 B1 | 2/2001 | Ouchi |
| 5,925,052 A | 7/1999 | Simmons | | 6,190,399 B1 | 2/2001 | Palmer et al. |
| 5,928,255 A | 7/1999 | Meade et al. | | 6,203,533 B1 | 3/2001 | Ouchi |
| 5,928,266 A | 7/1999 | Kontos | | 6,206,872 B1 | 3/2001 | Lafond et al. |
| 5,936,536 A | 8/1999 | Morris | | 6,206,877 B1 | 3/2001 | Kese et al. |
| 5,944,718 A | 8/1999 | Austin et al. | | 6,206,904 B1 | 3/2001 | Ouchi |
| 5,951,547 A | 9/1999 | Gough et al. | | 6,214,007 B1 | 4/2001 | Anderson |
| 5,951,549 A | 9/1999 | Richardson et al. | | 6,228,096 B1 | 5/2001 | Marchand |
| 5,954,720 A | 9/1999 | Wilson et al. | | 6,234,958 B1 | 5/2001 | Snoke et al. |
| 5,954,731 A | 9/1999 | Yoon | | 6,245,079 B1 | 6/2001 | Nobles et al. |
| 5,957,936 A | 9/1999 | Yoon et al. | | 6,246,914 B1 | 6/2001 | de la Rama et al. |
| 5,957,943 A | 9/1999 | Vaitekunas | | 6,258,064 B1 | 7/2001 | Smith et al. |
| 5,957,953 A | 9/1999 | DiPoto et al. | | 6,261,242 B1 | 7/2001 | Roberts et al. |
| 5,964,782 A | 10/1999 | Lafontaine et al. | | 6,264,664 B1 | 7/2001 | Avellanet |
| 5,971,995 A | 10/1999 | Rousseau | | 6,270,497 B1 | 8/2001 | Sekino et al. |
| 5,972,002 A | 10/1999 | Bark et al. | | 6,270,505 B1 | 8/2001 | Yoshida et al. |
| 5,976,074 A | 11/1999 | Moriyama | | 6,277,136 B1 | 8/2001 | Bonutti |
| 5,976,075 A | 11/1999 | Beane et al. | | 6,283,963 B1 | 9/2001 | Regula |
| 5,976,130 A | 11/1999 | McBrayer et al. | | 6,293,909 B1 | 9/2001 | Chu et al. |
| 5,976,131 A | 11/1999 | Guglielmi et al. | | 6,293,952 B1 | 9/2001 | Brosens et al. |
| 5,980,539 A | 11/1999 | Kontos | | 6,296,630 B1 | 10/2001 | Altman et al. |
| 5,980,556 A | 11/1999 | Giordano et al. | | 6,314,963 B1 | 11/2001 | Vaska et al. |
| 5,984,938 A | 11/1999 | Yoon | | 6,322,578 B1 | 11/2001 | Houle et al. |
| 5,984,939 A | 11/1999 | Yoon | | 6,326,177 B1 | 12/2001 | Schoenbach et al. |
| 5,984,950 A | 11/1999 | Cragg et al. | | 6,328,730 B1 | 12/2001 | Harkrider, Jr. |
| 5,989,182 A | 11/1999 | Hori et al. | | 6,350,267 B1 | 2/2002 | Stefanchik |
| 5,993,447 A | 11/1999 | Blewett et al. | | 6,350,278 B1 | 2/2002 | Lenker et al. |
| 5,993,474 A | 11/1999 | Ouchi | | 6,352,503 B1 | 3/2002 | Matsui et al. |
| 5,997,555 A | 12/1999 | Kontos | | 6,352,543 B1 | 3/2002 | Cole |
| 6,001,120 A | 12/1999 | Levin | | 6,355,013 B1 | 3/2002 | van Muiden |
| 6,004,269 A | 12/1999 | Crowley et al. | | 6,355,035 B1 | 3/2002 | Manushakian |
| 6,004,330 A | 12/1999 | Middleman et al. | | 6,361,534 B1 * | 3/2002 | Chen et al. .................... 606/45 |
| 6,007,566 A | 12/1999 | Wenstrom, Jr. | | 6,371,956 B1 | 4/2002 | Wilson et al. |
| 6,010,515 A | 1/2000 | Swain et al. | | 6,379,366 B1 | 4/2002 | Fleischman et al. |
| 6,012,494 A | 1/2000 | Balazs | | 6,383,195 B1 | 5/2002 | Richard |
| 6,017,356 A | 1/2000 | Frederick et al. | | 6,383,197 B1 | 5/2002 | Conlon et al. |
| 6,019,770 A | 2/2000 | Christoudias | | 6,387,671 B1 | 5/2002 | Rubinsky et al. |
| 6,024,708 A | 2/2000 | Bales et al. | | 6,391,029 B1 | 5/2002 | Hooven et al. |
| 6,024,747 A | 2/2000 | Kontos | | 6,398,708 B1 | 6/2002 | Hastings et al. |
| 6,027,522 A | 2/2000 | Palmer | | 6,402,735 B1 | 6/2002 | Langevin |
| 6,030,365 A | 2/2000 | Laufer | | 6,406,440 B1 | 6/2002 | Stefanchik |
| 6,030,634 A | 2/2000 | Wu et al. | | 6,409,727 B1 | 6/2002 | Bales et al. |
| 6,033,399 A | 3/2000 | Gines | | 6,409,733 B1 | 6/2002 | Conlon et al. |
| 6,036,685 A | 3/2000 | Mueller | | 6,419,641 B1 | 7/2002 | Mark et al. |
| 6,053,927 A | 4/2000 | Hamas | | 6,427,089 B1 | 7/2002 | Knowlton |
| 6,066,160 A | 5/2000 | Colvin et al. | | 6,431,500 B1 | 8/2002 | Jacobs et al. |
| 6,068,603 A | 5/2000 | Suzuki | | 6,436,107 B1 | 8/2002 | Wang et al. |
| 6,068,629 A | 5/2000 | Haissaguerre et al. | | 6,443,970 B1 | 9/2002 | Schulze et al. |
| 6,071,233 A | 6/2000 | Ishikawa et al. | | 6,443,988 B2 | 9/2002 | Felt et al. |
| 6,074,408 A | 6/2000 | Freeman | | 6,447,511 B1 | 9/2002 | Slater |
| 6,086,530 A | 7/2000 | Mack | | 6,447,523 B1 | 9/2002 | Middleman et al. |
| 6,090,105 A | 7/2000 | Zepeda et al. | | 6,454,783 B1 | 9/2002 | Piskun |
| 6,090,108 A | 7/2000 | McBrayer et al. | | 6,454,785 B2 | 9/2002 | De Hoyos Garza |
| 6,090,129 A | 7/2000 | Ouchi | | 6,458,076 B1 | 10/2002 | Pruitt |
| 6,096,046 A | 8/2000 | Weiss | | 6,464,701 B1 | 10/2002 | Hooven et al. |
| 6,102,926 A | 8/2000 | Tartaglia et al. | | 6,464,702 B2 | 10/2002 | Schulze et al. |

| Patent | Date | Inventor |
|---|---|---|
| 6,470,218 B1 | 10/2002 | Behl |
| 6,475,104 B1 | 11/2002 | Lutz et al. |
| 6,485,411 B1 | 11/2002 | Konstorum et al. |
| 6,489,745 B1 | 12/2002 | Koreis |
| 6,491,626 B1 | 12/2002 | Stone et al. |
| 6,491,627 B1 | 12/2002 | Komi |
| 6,491,691 B1 | 12/2002 | Morley et al. |
| 6,493,590 B1 | 12/2002 | Wessman et al. |
| 6,494,893 B2 | 12/2002 | Dubrul et al. |
| 6,500,176 B1 | 12/2002 | Truckai et al. |
| 6,503,192 B1 | 1/2003 | Ouchi |
| 6,506,190 B1 | 1/2003 | Walshe |
| 6,508,827 B1 | 1/2003 | Manhes |
| 6,514,239 B2 | 2/2003 | Shimmura et al. |
| 6,520,954 B2 | 2/2003 | Ouchi |
| 6,527,782 B2 | 3/2003 | Hogg et al. |
| 6,543,456 B1 | 4/2003 | Freeman |
| 6,551,270 B1 | 4/2003 | Bimbo et al. |
| 6,554,766 B2 | 4/2003 | Maeda et al. |
| 6,554,829 B2 | 4/2003 | Schulze et al. |
| 6,558,384 B2 | 5/2003 | Mayenberger |
| 6,562,035 B1 | 5/2003 | Levin |
| 6,562,052 B2 | 5/2003 | Nobles et al. |
| 6,569,159 B1 | 5/2003 | Edwards et al. |
| 6,572,629 B2 | 6/2003 | Kalloo et al. |
| 6,572,635 B1 | 6/2003 | Bonutti |
| 6,575,988 B2 | 6/2003 | Rousseau |
| 6,579,311 B1 | 6/2003 | Makower |
| 6,581,889 B2 | 6/2003 | Carpenter et al. |
| 6,585,642 B2 | 7/2003 | Christopher |
| 6,585,717 B1 | 7/2003 | Wittenberger et al. |
| 6,587,750 B2 | 7/2003 | Gerbi et al. |
| 6,592,559 B1 | 7/2003 | Pakter et al. |
| 6,592,603 B2 | 7/2003 | Lasner |
| 6,602,262 B2 | 8/2003 | Griego et al. |
| 6,605,105 B1 | 8/2003 | Cuschieri et al. |
| 6,610,072 B1 | 8/2003 | Christy et al. |
| 6,610,074 B2 | 8/2003 | Santilli |
| 6,620,193 B1 | 9/2003 | Lau et al. |
| 6,623,448 B2 | 9/2003 | Slater |
| 6,626,919 B1 | 9/2003 | Swanstrom |
| 6,632,229 B1 | 10/2003 | Yamanouchi |
| 6,638,286 B1 | 10/2003 | Burbank et al. |
| 6,645,225 B1 | 11/2003 | Atkinson |
| 6,652,521 B2 | 11/2003 | Schulze |
| 6,652,551 B1 | 11/2003 | Heiss |
| 6,656,194 B1 | 12/2003 | Gannoe et al. |
| 6,663,641 B1 | 12/2003 | Kovac et al. |
| 6,663,655 B2 | 12/2003 | Ginn et al. |
| 6,666,854 B1 | 12/2003 | Lange |
| 6,672,338 B1 | 1/2004 | Esashi et al. |
| 6,673,058 B2 | 1/2004 | Snow |
| 6,673,087 B1 | 1/2004 | Chang et al. |
| 6,679,882 B1 | 1/2004 | Kornerup |
| 6,685,628 B2 | 2/2004 | Vu |
| 6,685,724 B1 | 2/2004 | Haluck |
| 6,692,445 B2 | 2/2004 | Roberts et al. |
| 6,692,462 B2 | 2/2004 | Mackenzie et al. |
| 6,699,180 B2 | 3/2004 | Kobayashi |
| 6,699,256 B1 | 3/2004 | Logan et al. |
| 6,699,263 B2 | 3/2004 | Cope |
| 6,706,018 B2 | 3/2004 | Westlund et al. |
| 6,708,066 B2 | 3/2004 | Herbst et al. |
| 6,709,445 B2 | 3/2004 | Boebel et al. |
| 6,716,226 B2 | 4/2004 | Sixto, Jr. et al. |
| 6,736,822 B2 | 5/2004 | McClellan et al. |
| 6,740,030 B2 | 5/2004 | Martone et al. |
| 6,743,166 B2 | 6/2004 | Berci et al. |
| 6,743,239 B1 | 6/2004 | Kuehn et al. |
| 6,743,240 B2 | 6/2004 | Smith et al. |
| 6,749,560 B1 | 6/2004 | Konstorum et al. |
| 6,749,609 B1 | 6/2004 | Lunsford et al. |
| 6,752,768 B2 | 6/2004 | Burdorff et al. |
| 6,752,811 B2 | 6/2004 | Chu et al. |
| 6,752,822 B2 | 6/2004 | Jespersen |
| 6,758,857 B2 | 7/2004 | Cioanta et al. |
| 6,761,685 B2 | 7/2004 | Adams et al. |
| 6,761,718 B2 | 7/2004 | Madsen |
| 6,773,434 B2 | 8/2004 | Ciarrocca |
| 6,776,787 B2 | 8/2004 | Phung et al. |
| 6,780,151 B2 | 8/2004 | Grabover et al. |
| 6,780,352 B2 | 8/2004 | Jacobson |
| 6,783,491 B2 | 8/2004 | Saadat et al. |
| 6,786,864 B2 | 9/2004 | Matsuura et al. |
| 6,790,173 B2 | 9/2004 | Saadat et al. |
| 6,790,217 B2 | 9/2004 | Schulze et al. |
| 6,795,728 B2 | 9/2004 | Chornenky et al. |
| 6,800,056 B2 | 10/2004 | Tartaglia et al. |
| 6,808,491 B2 | 10/2004 | Kortenbach et al. |
| 6,817,974 B2 | 11/2004 | Cooper et al. |
| 6,824,548 B2 | 11/2004 | Smith et al. |
| 6,836,688 B2 | 12/2004 | Ingle et al. |
| 6,837,847 B2 | 1/2005 | Ewers et al. |
| 6,840,938 B1 | 1/2005 | Morley et al. |
| 6,843,794 B2 | 1/2005 | Sixto, Jr. et al. |
| 6,861,250 B1 | 3/2005 | Cole et al. |
| 6,866,627 B2 | 3/2005 | Nozue |
| 6,866,628 B2 | 3/2005 | Goodman et al. |
| 6,869,394 B2 | 3/2005 | Ishibiki |
| 6,878,106 B1 | 4/2005 | Herrmann |
| 6,878,110 B2 | 4/2005 | Yang et al. |
| 6,881,216 B2 | 4/2005 | Di Caprio et al. |
| 6,884,213 B2 | 4/2005 | Raz et al. |
| 6,887,255 B2 | 5/2005 | Shimm |
| 6,889,089 B2 | 5/2005 | Behl et al. |
| 6,896,683 B1 | 5/2005 | Gadberry et al. |
| 6,896,692 B2 | 5/2005 | Ginn et al. |
| 6,908,427 B2 | 6/2005 | Fleener et al. |
| 6,908,476 B2 | 6/2005 | Jud et al. |
| 6,916,284 B2 | 7/2005 | Moriyama |
| 6,918,871 B2 | 7/2005 | Schulze |
| 6,918,908 B2 | 7/2005 | Bonner et al. |
| 6,926,725 B2 | 8/2005 | Cooke et al. |
| 6,932,810 B2 | 8/2005 | Ryan |
| 6,932,824 B1 | 8/2005 | Roop et al. |
| 6,932,827 B2 | 8/2005 | Cole |
| 6,936,003 B2 | 8/2005 | Iddan |
| 6,939,327 B2 | 9/2005 | Hall et al. |
| 6,942,613 B2 | 9/2005 | Ewers et al. |
| 6,944,490 B1 | 9/2005 | Chow |
| 6,945,472 B2 | 9/2005 | Wuttke et al. |
| 6,945,979 B2 | 9/2005 | Kortenbach et al. |
| 6,958,035 B2 | 10/2005 | Friedman et al. |
| 6,960,162 B2 | 11/2005 | Saadat et al. |
| 6,960,163 B2 | 11/2005 | Ewers et al. |
| 6,962,587 B2 | 11/2005 | Johnson et al. |
| 6,964,662 B2 | 11/2005 | Kidooka |
| 6,966,909 B2 | 11/2005 | Marshall et al. |
| 6,966,919 B2 | 11/2005 | Sixto, Jr. et al. |
| 6,967,462 B1 | 11/2005 | Landis |
| 6,971,988 B2 | 12/2005 | Orban, III |
| 6,972,017 B2 | 12/2005 | Smith et al. |
| 6,974,411 B2 | 12/2005 | Belson |
| 6,976,992 B2 | 12/2005 | Sachatello et al. |
| 6,984,203 B2 | 1/2006 | Tartaglia et al. |
| 6,984,205 B2 | 1/2006 | Gazdzinski |
| 6,986,774 B2 | 1/2006 | Middleman et al. |
| 6,988,987 B2 | 1/2006 | Ishikawa et al. |
| 6,989,028 B2 | 1/2006 | Lashinski et al. |
| 6,991,627 B2 | 1/2006 | Madhani et al. |
| 6,991,631 B2 | 1/2006 | Woloszko et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,001,341 B2 | 2/2006 | Gellman et al. |
| 7,008,375 B2 | 3/2006 | Weisel |
| 7,009,634 B2 | 3/2006 | Iddan et al. |
| 7,010,340 B2 | 3/2006 | Scarantino et al. |
| 7,020,531 B1 | 3/2006 | Colliou et al. |
| 7,025,580 B2 | 4/2006 | Heagy et al. |
| 7,029,435 B2 | 4/2006 | Nakao |
| 7,029,438 B2 | 4/2006 | Morin et al. |
| 7,029,450 B2 | 4/2006 | Gellman |
| 7,032,600 B2 | 4/2006 | Fukuda et al. |
| 7,035,680 B2 | 4/2006 | Partridge et al. |
| 7,037,290 B2 | 5/2006 | Gardeski et al. |
| 7,041,052 B2 | 5/2006 | Saadat et al. |
| 7,052,489 B2 | 5/2006 | Griego et al. |

| | | | | | | |
|---|---|---|---|---|---|---|
| 7,060,024 B2 | 6/2006 | Long et al. | | 7,364,582 B2 | 4/2008 | Lee |
| 7,060,025 B2 | 6/2006 | Long et al. | | 7,371,215 B2 | 5/2008 | Colliou et al. |
| 7,063,697 B2 | 6/2006 | Slater | | 7,381,216 B2 | 6/2008 | Buzzard et al. |
| 7,063,715 B2 | 6/2006 | Onuki et al. | | 7,390,324 B2 | 6/2008 | Whalen et al. |
| 7,066,879 B2 | 6/2006 | Fowler et al. | | 7,393,222 B2 | 7/2008 | Asakura |
| 7,066,936 B2 | 6/2006 | Ryan | | 7,402,162 B2 | 7/2008 | Ouchi |
| 7,070,602 B2 | 7/2006 | Smith et al. | | 7,404,791 B2 | 7/2008 | Linares et al. |
| 7,076,305 B2 | 7/2006 | Imran et al. | | 7,410,483 B2 | 8/2008 | Danitz et al. |
| 7,083,618 B2 | 8/2006 | Couture et al. | | 7,413,563 B2 | 8/2008 | Corcoran et al. |
| 7,083,620 B2 | 8/2006 | Jahns et al. | | 7,416,554 B2 | 8/2008 | Lam et al. |
| 7,083,629 B2 | 8/2006 | Weller et al. | | 7,422,590 B2 | 9/2008 | Kupferschmid et al. |
| 7,083,635 B2 | 8/2006 | Ginn | | 7,435,257 B2 | 10/2008 | Lashinski et al. |
| 7,087,071 B2 | 8/2006 | Nicholas et al. | | 7,452,327 B2 | 11/2008 | Durgin et al. |
| 7,090,673 B2 | 8/2006 | Dycus et al. | | 7,455,208 B2 | 11/2008 | Wales et al. |
| 7,090,683 B2 | 8/2006 | Brock et al. | | 7,468,066 B2 | 12/2008 | Vargas et al. |
| 7,090,685 B2 | 8/2006 | Kortenbach et al. | | 7,488,295 B2 | 2/2009 | Burbank et al. |
| 7,093,518 B2 | 8/2006 | Gmeilbauer | | 7,494,499 B2 | 2/2009 | Nagase et al. |
| 7,101,371 B2 | 9/2006 | Dycus et al. | | 7,497,867 B2 | 3/2009 | Lasner et al. |
| 7,101,372 B2 | 9/2006 | Dycus et al. | | 7,498,950 B1 | 3/2009 | Ertas et al. |
| 7,101,373 B2 | 9/2006 | Dycus et al. | | 7,507,200 B2 | 3/2009 | Okada |
| 7,105,000 B2 | 9/2006 | McBrayer | | 7,510,107 B2 | 3/2009 | Timm et al. |
| 7,105,005 B2 | 9/2006 | Blake | | 7,511,733 B2 | 3/2009 | Takizawa et al. |
| 7,108,696 B2 | 9/2006 | Daniel et al. | | 7,515,953 B2 | 4/2009 | Madar et al. |
| 7,108,703 B2 | 9/2006 | Danitz et al. | | 7,520,876 B2 | 4/2009 | Ressemann et al. |
| 7,112,208 B2 | 9/2006 | Morris et al. | | 7,524,281 B2 | 4/2009 | Chu et al. |
| 7,115,092 B2 | 10/2006 | Park et al. | | 7,524,302 B2 | 4/2009 | Tower |
| 7,117,703 B2 | 10/2006 | Kato et al. | | 7,534,228 B2 | 5/2009 | Williams |
| 7,118,531 B2 | 10/2006 | Krill | | 7,540,872 B2 | 6/2009 | Schechter et al. |
| 7,118,578 B2 | 10/2006 | West, Jr. et al. | | 7,544,203 B2 | 6/2009 | Chin et al. |
| 7,118,587 B2 | 10/2006 | Dycus et al. | | 7,548,040 B2 | 6/2009 | Lee et al. |
| 7,128,708 B2 | 10/2006 | Saadat et al. | | 7,549,564 B2 | 6/2009 | Boudreaux |
| RE39,415 E | 11/2006 | Bales et al. | | 7,553,278 B2 | 6/2009 | Kucklick |
| 7,131,978 B2 | 11/2006 | Sancoff et al. | | 7,553,298 B2 | 6/2009 | Hunt et al. |
| 7,131,979 B2 | 11/2006 | DiCarlo et al. | | 7,559,887 B2 | 7/2009 | Dannan |
| 7,131,980 B1 | 11/2006 | Field et al. | | 7,559,916 B2 | 7/2009 | Smith et al. |
| 7,137,980 B2 | 11/2006 | Buysse et al. | | 7,560,006 B2 | 7/2009 | Rakos et al. |
| 7,137,981 B2 | 11/2006 | Long | | 7,561,916 B2 | 7/2009 | Hunt et al. |
| 7,146,984 B2 | 12/2006 | Stack et al. | | 7,566,334 B2 | 7/2009 | Christian et al. |
| 7,147,650 B2 | 12/2006 | Lee | | 7,575,144 B2 | 8/2009 | Ortiz et al. |
| 7,150,097 B2 | 12/2006 | Sremcich et al. | | 7,575,548 B2 | 8/2009 | Takemoto et al. |
| 7,150,655 B2 | 12/2006 | Mastrototaro et al. | | 7,579,550 B2 | 8/2009 | Dayton et al. |
| 7,150,750 B2 | 12/2006 | Damarati | | 7,582,096 B2 | 9/2009 | Gellman et al. |
| 7,152,488 B2 | 12/2006 | Hedrich et al. | | 7,588,177 B2 | 9/2009 | Racenet |
| 7,153,321 B2 | 12/2006 | Andrews | | 7,588,557 B2 | 9/2009 | Nakao |
| 7,160,296 B2 | 1/2007 | Pearson et al. | | 7,597,229 B2 | 10/2009 | Boudreaux et al. |
| 7,163,525 B2 | 1/2007 | Franer | | 7,604,150 B2 | 10/2009 | Boudreaux |
| 7,172,714 B2 | 2/2007 | Jacobson | | 7,608,083 B2 | 10/2009 | Lee et al. |
| 7,179,254 B2 | 2/2007 | Pendekanti et al. | | 7,618,398 B2 | 11/2009 | Holman et al. |
| 7,188,627 B2 | 3/2007 | Nelson et al. | | 7,632,250 B2 | 12/2009 | Smith et al. |
| 7,195,612 B2 | 3/2007 | Van Sloten et al. | | 7,635,373 B2 | 12/2009 | Ortiz |
| 7,195,631 B2 | 3/2007 | Dumbauld | | 7,637,903 B2 | 12/2009 | Lentz et al. |
| 7,204,820 B2 | 4/2007 | Akahoshi | | 7,650,742 B2 | 1/2010 | Ushijima |
| 7,208,005 B2 | 4/2007 | Frecker et al. | | 7,651,483 B2 | 1/2010 | Byrum et al. |
| 7,211,092 B2 | 5/2007 | Hughett | | 7,651,509 B2 | 1/2010 | Bojarski et al. |
| 7,220,227 B2 | 5/2007 | Sasaki et al. | | 7,654,431 B2 | 2/2010 | Hueil et al. |
| 7,223,272 B2 | 5/2007 | Francere et al. | | 7,662,089 B2 | 2/2010 | Okada et al. |
| 7,229,438 B2 | 6/2007 | Young | | 7,666,180 B2 | 2/2010 | Holsten et al. |
| 7,232,414 B2 | 6/2007 | Gonzalez | | 7,666,203 B2 | 2/2010 | Chanduszko et al. |
| 7,232,445 B2 | 6/2007 | Kortenbach et al. | | 7,674,259 B2 | 3/2010 | Shadduck |
| 7,235,089 B1 | 6/2007 | McGuckin, Jr. | | 7,678,043 B2 | 3/2010 | Gilad |
| 7,241,290 B2 | 7/2007 | Doyle et al. | | 7,684,599 B2 | 3/2010 | Horn et al. |
| 7,244,228 B2 | 7/2007 | Lubowski | | 7,697,970 B2 | 4/2010 | Uchiyama et al. |
| 7,250,027 B2 | 7/2007 | Barry | | 7,699,835 B2 | 4/2010 | Lee et al. |
| 7,252,660 B2 | 8/2007 | Kunz | | 7,699,864 B2 | 4/2010 | Kick et al. |
| 7,255,675 B2 | 8/2007 | Gertner et al. | | 7,713,189 B2 | 5/2010 | Hanke |
| 7,270,663 B2 | 9/2007 | Nakao | | 7,713,270 B2 | 5/2010 | Suzuki |
| 7,294,139 B1 | 11/2007 | Gengler | | 7,736,374 B2 | 6/2010 | Vaughan et al. |
| 7,301,250 B2 | 11/2007 | Cassel | | 7,744,615 B2 | 6/2010 | Couture |
| 7,306,597 B2 | 12/2007 | Manzo | | 7,753,933 B2 | 7/2010 | Ginn et al. |
| 7,308,828 B2 | 12/2007 | Hashimoto | | 7,758,577 B2 | 7/2010 | Nobis et al. |
| 7,318,802 B2 | 1/2008 | Suzuki et al. | | 7,762,949 B2 | 7/2010 | Nakao |
| 7,320,695 B2 | 1/2008 | Carroll | | 7,762,998 B2 | 7/2010 | Birk et al. |
| 7,322,934 B2 | 1/2008 | Miyake et al. | | 7,763,012 B2 | 7/2010 | Petrick et al. |
| 7,323,006 B2 | 1/2008 | Andreas et al. | | 7,771,416 B2 | 8/2010 | Spivey et al. |
| 7,329,256 B2 | 2/2008 | Johnson et al. | | 7,780,683 B2 | 8/2010 | Roue et al. |
| 7,329,257 B2 | 2/2008 | Kanehira et al. | | 7,780,691 B2 | 8/2010 | Stefanchik |
| 7,329,383 B2 | 2/2008 | Stinson | | 7,784,663 B2 | 8/2010 | Shelton, IV |
| 7,344,536 B1 | 3/2008 | Lunsford et al. | | 7,794,409 B2 | 9/2010 | Damarati |
| 7,352,387 B2 | 4/2008 | Yamamoto | | 7,794,475 B2 | 9/2010 | Hess et al. |

| Patent/Publication | Date | Name |
|---|---|---|
| 7,798,386 B2 | 9/2010 | Schall et al. |
| 7,828,186 B2 | 11/2010 | Wales |
| 7,837,615 B2 | 11/2010 | Le et al. |
| 7,842,028 B2 | 11/2010 | Lee |
| 7,842,068 B2 | 11/2010 | Ginn |
| 7,846,171 B2 | 12/2010 | Kullas et al. |
| 7,850,660 B2 | 12/2010 | Uth et al. |
| 7,857,183 B2 | 12/2010 | Shelton, IV |
| 7,862,546 B2 | 1/2011 | Conlon et al. |
| 7,867,216 B2 | 1/2011 | Wahr et al. |
| 7,892,220 B2 | 2/2011 | Faller et al. |
| 7,896,887 B2 | 3/2011 | Rimbaugh et al. |
| 7,905,828 B2 | 3/2011 | Brock et al. |
| 7,909,809 B2 | 3/2011 | Scopton et al. |
| 7,914,513 B2 | 3/2011 | Voorhees, Jr. |
| 7,918,869 B2 | 4/2011 | Saadat et al. |
| 7,931,624 B2 | 4/2011 | Smith et al. |
| 7,945,332 B2 | 5/2011 | Schechter |
| 7,947,000 B2 | 5/2011 | Vargas et al. |
| 7,955,298 B2 | 6/2011 | Carroll et al. |
| 7,963,975 B2 | 6/2011 | Criscuolo |
| 7,965,180 B2 | 6/2011 | Koyama |
| 7,967,808 B2 | 6/2011 | Fitzgerald et al. |
| 7,969,473 B2 | 6/2011 | Kotoda |
| 7,988,685 B2 | 8/2011 | Ziaie et al. |
| 8,048,067 B2 | 11/2011 | Davalos et al. |
| 8,057,510 B2 | 11/2011 | Ginn et al. |
| 8,066,632 B2 | 11/2011 | Dario et al. |
| 8,075,587 B2 | 12/2011 | Ginn |
| 8,088,062 B2 | 1/2012 | Zwolinski |
| 8,118,821 B2 | 2/2012 | Mouw |
| 8,147,424 B2 | 4/2012 | Kassab et al. |
| 8,157,813 B2 | 4/2012 | Ko et al. |
| 2001/0023333 A1 | 9/2001 | Wise et al. |
| 2001/0049497 A1 | 12/2001 | Kalloo et al. |
| 2002/0022771 A1 | 2/2002 | Diokno et al. |
| 2002/0022857 A1 | 2/2002 | Goldsteen et al. |
| 2002/0023353 A1 | 2/2002 | Ting-Kung |
| 2002/0029055 A1 | 3/2002 | Bonutti |
| 2002/0042562 A1 | 4/2002 | Meron et al. |
| 2002/0049439 A1 | 4/2002 | Mulier et al. |
| 2002/0068945 A1 | 6/2002 | Sixto, Jr. et al. |
| 2002/0078967 A1 | 6/2002 | Sixto, Jr. et al. |
| 2002/0082516 A1 | 6/2002 | Stefanchik |
| 2002/0091391 A1 | 7/2002 | Cole et al. |
| 2002/0095164 A1 | 7/2002 | Andreas et al. |
| 2002/0107530 A1 | 8/2002 | Sauer et al. |
| 2002/0133115 A1 | 9/2002 | Gordon et al. |
| 2002/0138086 A1 | 9/2002 | Sixto, Jr. et al. |
| 2002/0147456 A1 | 10/2002 | Diduch et al. |
| 2002/0165592 A1 | 11/2002 | Glukhovsky et al. |
| 2002/0183591 A1 | 12/2002 | Matsuura et al. |
| 2003/0023255 A1 | 1/2003 | Miles et al. |
| 2003/0036679 A1 | 2/2003 | Kortenbach et al. |
| 2003/0069602 A1 | 4/2003 | Jacobs et al. |
| 2003/0083681 A1 | 5/2003 | Moutafis et al. |
| 2003/0114731 A1 | 6/2003 | Cadeddu et al. |
| 2003/0114732 A1 | 6/2003 | Webler et al. |
| 2003/0120257 A1 | 6/2003 | Houston et al. |
| 2003/0124009 A1 | 7/2003 | Ravi et al. |
| 2003/0130564 A1 | 7/2003 | Martone et al. |
| 2003/0130656 A1 | 7/2003 | Levin |
| 2003/0158521 A1 | 8/2003 | Ameri |
| 2003/0167062 A1 | 9/2003 | Gambale et al. |
| 2003/0171651 A1 | 9/2003 | Page et al. |
| 2003/0176880 A1 | 9/2003 | Long et al. |
| 2003/0191497 A1 | 10/2003 | Cope |
| 2003/0195565 A1 | 10/2003 | Bonutti |
| 2003/0216611 A1 | 11/2003 | Vu |
| 2003/0216615 A1 | 11/2003 | Ouchi |
| 2003/0220545 A1 | 11/2003 | Ouchi |
| 2003/0225312 A1 | 12/2003 | Suzuki et al. |
| 2003/0225332 A1 | 12/2003 | Okada et al. |
| 2003/0229269 A1 | 12/2003 | Humphrey |
| 2003/0229371 A1 | 12/2003 | Whitworth |
| 2003/0236549 A1 | 12/2003 | Bonadio et al. |
| 2004/0002683 A1 | 1/2004 | Nicholson et al. |
| 2004/0002735 A1 | 1/2004 | Lizardi et al. |
| 2004/0034369 A1 | 2/2004 | Sauer et al. |
| 2004/0054322 A1 | 3/2004 | Vargas |
| 2004/0098007 A1 | 5/2004 | Heiss |
| 2004/0101456 A1 | 5/2004 | Kuroshima et al. |
| 2004/0104999 A1 | 6/2004 | Okada |
| 2004/0116948 A1 | 6/2004 | Sixto, Jr. et al. |
| 2004/0127940 A1 | 7/2004 | Ginn et al. |
| 2004/0133077 A1 | 7/2004 | Obenchain et al. |
| 2004/0133089 A1 | 7/2004 | Kilcoyne et al. |
| 2004/0136779 A1 | 7/2004 | Bhaskar |
| 2004/0138525 A1 | 7/2004 | Saadat et al. |
| 2004/0138529 A1 | 7/2004 | Wiltshire et al. |
| 2004/0138587 A1 | 7/2004 | Lyons, IV |
| 2004/0161451 A1 | 8/2004 | Pierce et al. |
| 2004/0186350 A1 | 9/2004 | Brenneman et al. |
| 2004/0193009 A1 | 9/2004 | Jaffe et al. |
| 2004/0193146 A1 | 9/2004 | Lee et al |
| 2004/0193186 A1 | 9/2004 | Kortenbach et al. |
| 2004/0193188 A1 | 9/2004 | Francese |
| 2004/0193189 A1 | 9/2004 | Kortenbach et al. |
| 2004/0193200 A1 | 9/2004 | Dworschak et al. |
| 2004/0199052 A1 | 10/2004 | Banik et al. |
| 2004/0199159 A1 | 10/2004 | Lee et al. |
| 2004/0206859 A1 | 10/2004 | Chong et al. |
| 2004/0210245 A1 | 10/2004 | Erickson et al. |
| 2004/0215058 A1 | 10/2004 | Zirps et al. |
| 2004/0225183 A1 | 11/2004 | Michlitsch et al. |
| 2004/0225186 A1 | 11/2004 | Horne, Jr. et al. |
| 2004/0230095 A1 | 11/2004 | Stefanchik et al. |
| 2004/0230096 A1 | 11/2004 | Stefanchik et al. |
| 2004/0230097 A1 | 11/2004 | Stefanchik et al. |
| 2004/0230161 A1 | 11/2004 | Zeiner |
| 2004/0249246 A1 | 12/2004 | Campos |
| 2004/0249367 A1 | 12/2004 | Saadat et al. |
| 2004/0249394 A1 | 12/2004 | Morris et al. |
| 2004/0249443 A1 | 12/2004 | Shanley et al. |
| 2004/0254572 A1 | 12/2004 | McIntyre et al. |
| 2005/0004515 A1 | 1/2005 | Hart et al. |
| 2005/0033265 A1 | 2/2005 | Engel et al. |
| 2005/0033277 A1 | 2/2005 | Clague et al. |
| 2005/0033319 A1 | 2/2005 | Gambale et al. |
| 2005/0033333 A1 | 2/2005 | Smith et al. |
| 2005/0043690 A1 | 2/2005 | Todd |
| 2005/0049616 A1 | 3/2005 | Rivera et al. |
| 2005/0065397 A1 | 3/2005 | Saadat et al. |
| 2005/0065517 A1 | 3/2005 | Chin |
| 2005/0070754 A1 | 3/2005 | Nobis et al. |
| 2005/0070763 A1 | 3/2005 | Nobis et al. |
| 2005/0070764 A1 | 3/2005 | Nobis et al. |
| 2005/0080413 A1 | 4/2005 | Canady |
| 2005/0085693 A1 | 4/2005 | Belson et al. |
| 2005/0085832 A1 | 4/2005 | Sancoff et al. |
| 2005/0090837 A1 | 4/2005 | Sixto, Jr. et al. |
| 2005/0090838 A1 | 4/2005 | Sixto, Jr. et al. |
| 2005/0096502 A1 | 5/2005 | Khalili |
| 2005/0101837 A1 | 5/2005 | Kalloo et al. |
| 2005/0101838 A1 | 5/2005 | Camillocci et al. |
| 2005/0101984 A1 | 5/2005 | Chanduszko et al. |
| 2005/0107663 A1 | 5/2005 | Saadat et al. |
| 2005/0107664 A1 | 5/2005 | Kalloo et al. |
| 2005/0110881 A1 | 5/2005 | Glukhovsky et al. |
| 2005/0113847 A1 | 5/2005 | Gadberry et al. |
| 2005/0119613 A1 | 6/2005 | Moenning et al. |
| 2005/0124855 A1 | 6/2005 | Jaffe et al. |
| 2005/0125010 A1 | 6/2005 | Smith et al. |
| 2005/0131279 A1 | 6/2005 | Boulais et al. |
| 2005/0131457 A1 | 6/2005 | Douglas et al. |
| 2005/0137454 A1 | 6/2005 | Saadat et al. |
| 2005/0143647 A1 | 6/2005 | Minai et al. |
| 2005/0143690 A1 | 6/2005 | High |
| 2005/0143774 A1 | 6/2005 | Polo |
| 2005/0143803 A1 | 6/2005 | Watson et al. |
| 2005/0149087 A1 | 7/2005 | Ahlberg et al. |
| 2005/0149096 A1 | 7/2005 | Hilal et al. |
| 2005/0159648 A1 | 7/2005 | Freed |
| 2005/0165272 A1 | 7/2005 | Okada et al. |
| 2005/0165378 A1 | 7/2005 | Heinrich et al. |
| 2005/0165411 A1 | 7/2005 | Orban, III |
| 2005/0165429 A1 | 7/2005 | Douglas et al. |
| 2005/0182429 A1 | 8/2005 | Yamanouchi |

| | | | | | |
|---|---|---|---|---|---|
| 2005/0192478 A1 | 9/2005 | Williams et al. | 2006/0200005 A1 | 9/2006 | Bjork et al. |
| 2005/0192598 A1 | 9/2005 | Johnson et al. | 2006/0200121 A1 | 9/2006 | Mowery |
| 2005/0192602 A1 | 9/2005 | Manzo | 2006/0200169 A1 | 9/2006 | Sniffin |
| 2005/0192654 A1 | 9/2005 | Chanduszko et al. | 2006/0200170 A1 | 9/2006 | Aranyi |
| 2005/0209624 A1 | 9/2005 | Vijay | 2006/0200199 A1 | 9/2006 | Bonutti et al. |
| 2005/0215858 A1 | 9/2005 | Vail et al. | 2006/0217665 A1 | 9/2006 | Prosek |
| 2005/0216050 A1 | 9/2005 | Sepetka et al. | 2006/0217697 A1 | 9/2006 | Lau et al. |
| 2005/0228406 A1 | 10/2005 | Bose | 2006/0217742 A1 | 9/2006 | Messerly et al. |
| 2005/0234297 A1 | 10/2005 | Devierre et al. | 2006/0217743 A1 | 9/2006 | Messerly et al. |
| 2005/0250983 A1 | 11/2005 | Tremaglio et al. | 2006/0229639 A1 | 10/2006 | Whitfield |
| 2005/0250990 A1 | 11/2005 | Le et al. | 2006/0229640 A1 | 10/2006 | Whitfield |
| 2005/0250993 A1 | 11/2005 | Jaeger | 2006/0237022 A1 | 10/2006 | Chen et al. |
| 2005/0251166 A1 | 11/2005 | Vaughan et al. | 2006/0237023 A1 | 10/2006 | Cox et al. |
| 2005/0251176 A1 | 11/2005 | Swanstrom et al. | 2006/0241570 A1 | 10/2006 | Wilk |
| 2005/0261674 A1 | 11/2005 | Nobis et al. | 2006/0247576 A1 | 11/2006 | Poncet |
| 2005/0267492 A1 | 12/2005 | Poncet et al. | 2006/0247673 A1 | 11/2006 | Voegele et al. |
| 2005/0272975 A1 | 12/2005 | McWeeney et al. | 2006/0253004 A1 | 11/2006 | Frisch et al. |
| 2005/0272977 A1 | 12/2005 | Saadat et al. | 2006/0253039 A1 | 11/2006 | McKenna et al. |
| 2005/0273084 A1 | 12/2005 | Hinman et al. | 2006/0258907 A1 | 11/2006 | Stefanchik et al. |
| 2005/0274935 A1 | 12/2005 | Nelson | 2006/0258908 A1 | 11/2006 | Stefanchik et al. |
| 2005/0277945 A1 | 12/2005 | Saadat et al. | 2006/0258910 A1 | 11/2006 | Stefanchik et al. |
| 2005/0277951 A1 | 12/2005 | Smith et al. | 2006/0258954 A1 | 11/2006 | Timberlake et al. |
| 2005/0277952 A1 | 12/2005 | Arp et al. | 2006/0258955 A1 | 11/2006 | Hoffman et al. |
| 2005/0277954 A1 | 12/2005 | Smith et al. | 2006/0259010 A1 | 11/2006 | Stefanchik et al. |
| 2005/0277955 A1 | 12/2005 | Palmer et al. | 2006/0264752 A1 | 11/2006 | Rubinsky et al. |
| 2005/0277956 A1 | 12/2005 | Francese et al. | 2006/0264904 A1 | 11/2006 | Kerby et al. |
| 2005/0277957 A1 | 12/2005 | Kuhns et al. | 2006/0264930 A1 | 11/2006 | Nishimura |
| 2005/0283118 A1 | 12/2005 | Uth et al. | 2006/0270902 A1 | 11/2006 | Igarashi et al. |
| 2005/0283119 A1 | 12/2005 | Uth et al. | 2006/0271042 A1* | 11/2006 | Latterell et al. .................. 606/51 |
| 2005/0288555 A1 | 12/2005 | Binmoeller | 2006/0271102 A1 | 11/2006 | Bosshard et al. |
| 2006/0004406 A1 | 1/2006 | Wehrstein et al. | 2006/0276835 A1 | 12/2006 | Uchida |
| 2006/0004409 A1 | 1/2006 | Nobis et al. | 2006/0281970 A1 | 12/2006 | Stokes et al. |
| 2006/0004410 A1 | 1/2006 | Nobis et al. | 2006/0282106 A1 | 12/2006 | Cole et al. |
| 2006/0015009 A1 | 1/2006 | Jaffe et al. | 2006/0285732 A1 | 12/2006 | Horn et al. |
| 2006/0020167 A1 | 1/2006 | Sitzmann | 2006/0287644 A1 | 12/2006 | Inganas et al. |
| 2006/0020247 A1 | 1/2006 | Kagan et al. | 2006/0287666 A1 | 12/2006 | Saadat et al. |
| 2006/0025654 A1 | 2/2006 | Suzuki et al. | 2006/0293626 A1 | 12/2006 | Byrum et al. |
| 2006/0025781 A1 | 2/2006 | Young et al. | 2007/0002135 A1 | 1/2007 | Glukhovsky |
| 2006/0025812 A1 | 2/2006 | Shelton, IV | 2007/0005019 A1 | 1/2007 | Okishige |
| 2006/0025819 A1 | 2/2006 | Nobis et al. | 2007/0010801 A1 | 1/2007 | Chen et al. |
| 2006/0036267 A1 | 2/2006 | Saadat et al. | 2007/0015965 A1 | 1/2007 | Cox et al. |
| 2006/0041188 A1 | 2/2006 | Dirusso et al. | 2007/0016255 A1 | 1/2007 | Korb et al. |
| 2006/0058582 A1 | 3/2006 | Maahs et al. | 2007/0032700 A1 | 2/2007 | Fowler et al. |
| 2006/0058776 A1 | 3/2006 | Bilsbury | 2007/0032701 A1 | 2/2007 | Fowler et al. |
| 2006/0069396 A1 | 3/2006 | Meade et al. | 2007/0043261 A1 | 2/2007 | Watanabe et al. |
| 2006/0069424 A1 | 3/2006 | Acosta et al. | 2007/0043345 A1 | 2/2007 | Davalos et al. |
| 2006/0069425 A1 | 3/2006 | Hillis et al. | 2007/0049800 A1 | 3/2007 | Boulais |
| 2006/0069429 A1 | 3/2006 | Spence et al. | 2007/0049902 A1 | 3/2007 | Griffin et al. |
| 2006/0074413 A1 | 4/2006 | Behzadian | 2007/0051375 A1 | 3/2007 | Milliman |
| 2006/0079890 A1 | 4/2006 | Guerra | 2007/0060880 A1 | 3/2007 | Gregorich et al. |
| 2006/0089528 A1 | 4/2006 | Tartaglia et al. | 2007/0067017 A1 | 3/2007 | Trapp |
| 2006/0095031 A1 | 5/2006 | Ormsby | 2007/0073102 A1 | 3/2007 | Matsuno et al. |
| 2006/0095060 A1 | 5/2006 | Mayenberger et al. | 2007/0073269 A1 | 3/2007 | Becker |
| 2006/0100687 A1 | 5/2006 | Fahey et al. | 2007/0079924 A1 | 4/2007 | Saadat et al. |
| 2006/0106423 A1 | 5/2006 | Weisel et al. | 2007/0088370 A1 | 4/2007 | Kahle et al. |
| 2006/0111209 A1 | 5/2006 | Hinman et al. | 2007/0100375 A1 | 5/2007 | Mikkaichi et al. |
| 2006/0111210 A1 | 5/2006 | Hinman et al. | 2007/0100376 A1 | 5/2007 | Mikkaichi et al. |
| 2006/0111704 A1 | 5/2006 | Brenneman et al. | 2007/0106118 A1 | 5/2007 | Moriyama |
| 2006/0129166 A1 | 6/2006 | Lavelle | 2007/0112251 A1 | 5/2007 | Nakhuda |
| 2006/0135962 A1 | 6/2006 | Kick et al. | 2007/0112331 A1 | 5/2007 | Weber et al. |
| 2006/0135971 A1 | 6/2006 | Swanstrom et al. | 2007/0112342 A1 | 5/2007 | Pearson et al. |
| 2006/0135984 A1 | 6/2006 | Kramer et al. | 2007/0112383 A1 | 5/2007 | Conlon et al. |
| 2006/0142644 A1 | 6/2006 | Mulac et al. | 2007/0112384 A1 | 5/2007 | Conlon et al. |
| 2006/0142652 A1 | 6/2006 | Keenan | 2007/0112385 A1 | 5/2007 | Conlon |
| 2006/0142790 A1 | 6/2006 | Gertner | 2007/0112417 A1 | 5/2007 | Shanley et al. |
| 2006/0142798 A1 | 6/2006 | Holman et al. | 2007/0112425 A1 | 5/2007 | Schaller et al. |
| 2006/0149131 A1 | 7/2006 | Or | 2007/0118115 A1 | 5/2007 | Artale et al. |
| 2006/0149132 A1 | 7/2006 | Iddan | 2007/0122425 A1 | 5/2007 | Keeler et al. |
| 2006/0149135 A1 | 7/2006 | Paz | 2007/0123840 A1 | 5/2007 | Cox |
| 2006/0161190 A1 | 7/2006 | Gadberry et al. | 2007/0129605 A1 | 6/2007 | Schaaf |
| 2006/0167416 A1 | 7/2006 | Mathis et al. | 2007/0129719 A1 | 6/2007 | Kendale et al. |
| 2006/0167482 A1 | 7/2006 | Swain et al. | 2007/0129760 A1 | 6/2007 | Demarais et al. |
| 2006/0178560 A1 | 8/2006 | Saadat et al. | 2007/0135709 A1 | 6/2007 | Rioux et al. |
| 2006/0183975 A1 | 8/2006 | Saadat et al. | 2007/0135803 A1 | 6/2007 | Belson |
| 2006/0184161 A1 | 8/2006 | Maahs et al. | 2007/0142706 A1 | 6/2007 | Matsui et al. |
| 2006/0189844 A1 | 8/2006 | Tien | 2007/0142780 A1 | 6/2007 | Van Lue |
| 2006/0189845 A1 | 8/2006 | Maahs et al. | 2007/0154460 A1 | 7/2007 | Kraft et al. |
| 2006/0190027 A1 | 8/2006 | Downey | 2007/0156028 A1 | 7/2007 | Van Lue et al. |
| 2006/0195084 A1 | 8/2006 | Slater | 2007/0156127 A1 | 7/2007 | Rioux et al. |

| | | | | | | |
|---|---|---|---|---|---|---|
| 2007/0161855 A1 | 7/2007 | Mikkaichi et al. | | 2008/0230972 A1 | 9/2008 | Ganley |
| 2007/0162101 A1 | 7/2007 | Burgermeister et al. | | 2008/0234696 A1 | 9/2008 | Taylor et al. |
| 2007/0167901 A1 | 7/2007 | Herrig et al. | | 2008/0243106 A1 | 10/2008 | Coe et al. |
| 2007/0173691 A1 | 7/2007 | Yokoi et al. | | 2008/0243148 A1 | 10/2008 | Mikkaichi et al. |
| 2007/0173869 A1 | 7/2007 | Gannoe et al. | | 2008/0243176 A1 | 10/2008 | Weitzner et al. |
| 2007/0173870 A2 | 7/2007 | Zacharias | | 2008/0249567 A1 | 10/2008 | Kaplan |
| 2007/0173872 A1 | 7/2007 | Neuenfeldt | | 2008/0262513 A1 | 10/2008 | Stahler et al. |
| 2007/0179525 A1 | 8/2007 | Frecker et al. | | 2008/0262540 A1 | 10/2008 | Bangera et al. |
| 2007/0179530 A1 | 8/2007 | Tieu et al. | | 2008/0269782 A1 | 10/2008 | Stefanchik et al. |
| 2007/0197865 A1 | 8/2007 | Miyake et al. | | 2008/0269783 A1 | 10/2008 | Griffith |
| 2007/0198057 A1 | 8/2007 | Gelbart et al. | | 2008/0275474 A1 | 11/2008 | Martin et al. |
| 2007/0203398 A1 | 8/2007 | Bonadio et al. | | 2008/0275475 A1 | 11/2008 | Schwemberger et al. |
| 2007/0203487 A1 | 8/2007 | Sugita | | 2008/0287737 A1 | 11/2008 | Dejima |
| 2007/0208336 A1 | 9/2007 | Kim et al. | | 2008/0287983 A1 | 11/2008 | Smith et al. |
| 2007/0208364 A1 | 9/2007 | Smith et al. | | 2008/0300461 A1 | 12/2008 | Shaw et al. |
| 2007/0213754 A1 | 9/2007 | Mikkaichi et al. | | 2008/0300547 A1 | 12/2008 | Bakos |
| 2007/0225554 A1 | 9/2007 | Maseda et al. | | 2008/0309758 A1 | 12/2008 | Karasawa et al. |
| 2007/0233040 A1 | 10/2007 | Macnamara et al. | | 2008/0312496 A1 | 12/2008 | Zwolinski |
| 2007/0244358 A1 | 10/2007 | Lee | | 2008/0312499 A1 | 12/2008 | Handa et al. |
| 2007/0250038 A1 | 10/2007 | Boulais | | 2008/0312500 A1 | 12/2008 | Asada et al. |
| 2007/0250057 A1 | 10/2007 | Nobis et al. | | 2008/0312506 A1 | 12/2008 | Spivey et al. |
| 2007/0255096 A1 | 11/2007 | Stefanchik et al. | | 2008/0319436 A1 | 12/2008 | Daniel et al. |
| 2007/0255100 A1 | 11/2007 | Barlow et al. | | 2008/0319439 A1 | 12/2008 | Ootsubu |
| 2007/0255273 A1 | 11/2007 | Fernandez et al. | | 2009/0054728 A1 | 2/2009 | Trusty |
| 2007/0255303 A1 | 11/2007 | Bakos et al. | | 2009/0062788 A1 | 3/2009 | Long et al. |
| 2007/0255306 A1 | 11/2007 | Conlon et al. | | 2009/0062792 A1 | 3/2009 | Vakharia et al. |
| 2007/0260112 A1 | 11/2007 | Rahmani | | 2009/0062795 A1 | 3/2009 | Vakharia et al. |
| 2007/0260117 A1 | 11/2007 | Zwolinski et al. | | 2009/0069634 A1 | 3/2009 | Larkin |
| 2007/0260121 A1 | 11/2007 | Bakos et al. | | 2009/0076499 A1 | 3/2009 | Azure |
| 2007/0260242 A1 | 11/2007 | Dycus et al. | | 2009/0078736 A1 | 3/2009 | Van Lue |
| 2007/0260273 A1 | 11/2007 | Cropper et al. | | 2009/0082776 A1 | 3/2009 | Cresina |
| 2007/0270629 A1 | 11/2007 | Charles | | 2009/0082779 A1 | 3/2009 | Nakao |
| 2007/0270889 A1 | 11/2007 | Conlon et al. | | 2009/0112059 A1 | 4/2009 | Nobis |
| 2007/0270895 A1 | 11/2007 | Nobis et al. | | 2009/0112062 A1 | 4/2009 | Bakos |
| 2007/0270907 A1 | 11/2007 | Stokes et al. | | 2009/0112063 A1 | 4/2009 | Bakos et al. |
| 2007/0282371 A1 | 12/2007 | Lee et al. | | 2009/0125042 A1 | 5/2009 | Mouw |
| 2007/0293727 A1 | 12/2007 | Goldfarb et al. | | 2009/0131751 A1 | 5/2009 | Spivey et al. |
| 2007/0299387 A1 | 12/2007 | Williams et al. | | 2009/0131932 A1 | 5/2009 | Vakharia et al. |
| 2008/0004650 A1 | 1/2008 | George | | 2009/0131933 A1 | 5/2009 | Ghabrial et al. |
| 2008/0015409 A1 | 1/2008 | Barlow et al. | | 2009/0143639 A1 | 6/2009 | Stark |
| 2008/0015413 A1 | 1/2008 | Barlow et al. | | 2009/0143649 A1 | 6/2009 | Rossi |
| 2008/0015552 A1 | 1/2008 | Doyle et al. | | 2009/0143794 A1 | 6/2009 | Conlon et al. |
| 2008/0021416 A1 | 1/2008 | Arai et al. | | 2009/0143818 A1 | 6/2009 | Faller et al. |
| 2008/0022927 A1 | 1/2008 | Zhang et al. | | 2009/0149710 A1 | 6/2009 | Stefanchik et al. |
| 2008/0027387 A1 | 1/2008 | Grabinsky | | 2009/0177031 A1 | 7/2009 | Surti et al. |
| 2008/0033451 A1 | 2/2008 | Rieber et al. | | 2009/0177219 A1 | 7/2009 | Conlon |
| 2008/0051629 A1 | 2/2008 | Sugiyama et al. | | 2009/0182332 A1 | 7/2009 | Long et al. |
| 2008/0051735 A1 | 2/2008 | Measamer et al. | | 2009/0192344 A1 | 7/2009 | Bakos et al. |
| 2008/0058586 A1 | 3/2008 | Karpiel | | 2009/0192534 A1 | 7/2009 | Ortiz et al. |
| 2008/0058854 A1 | 3/2008 | Kieturakis et al. | | 2009/0198231 A1 | 8/2009 | Esser et al. |
| 2008/0065169 A1 | 3/2008 | Colliou et al. | | 2009/0198253 A1 | 8/2009 | Omori |
| 2008/0071264 A1 | 3/2008 | Azure | | 2009/0216248 A1 | 8/2009 | Uenohara et al. |
| 2008/0086172 A1 | 4/2008 | Martin et al. | | 2009/0227828 A1 | 9/2009 | Swain et al. |
| 2008/0097159 A1 | 4/2008 | Ishiguro | | 2009/0248055 A1 | 10/2009 | Spivey et al. |
| 2008/0097472 A1 | 4/2008 | Agmon et al. | | 2009/0269317 A1 | 10/2009 | Davalos |
| 2008/0097483 A1 | 4/2008 | Ortiz et al. | | 2009/0281559 A1 | 11/2009 | Swain et al. |
| 2008/0103527 A1 | 5/2008 | Martin et al. | | 2009/0287206 A1 | 11/2009 | Jun |
| 2008/0114384 A1 | 5/2008 | Chang et al. | | 2009/0287236 A1 | 11/2009 | Bakos et al. |
| 2008/0119870 A1 | 5/2008 | Williams | | 2009/0292164 A1 | 11/2009 | Yamatani |
| 2008/0119891 A1 | 5/2008 | Miles et al. | | 2009/0299135 A1 | 12/2009 | Spivey |
| 2008/0125796 A1 | 5/2008 | Graham | | 2009/0299143 A1 | 12/2009 | Conlon et al. |
| 2008/0132892 A1 | 6/2008 | Lunsford et al. | | 2009/0299362 A1 | 12/2009 | Long et al. |
| 2008/0139882 A1 | 6/2008 | Fujimori | | 2009/0299385 A1 | 12/2009 | Stefanchik et al. |
| 2008/0140071 A1 | 6/2008 | Vegesna | | 2009/0299406 A1 | 12/2009 | Swain et al. |
| 2008/0147113 A1 | 6/2008 | Nobis et al. | | 2009/0299409 A1 | 12/2009 | Coe et al. |
| 2008/0171907 A1 | 7/2008 | Long et al. | | 2009/0306658 A1 | 12/2009 | Nobis et al. |
| 2008/0177135 A1 | 7/2008 | Muyari et al. | | 2009/0306683 A1 | 12/2009 | Zwolinski et al. |
| 2008/0188710 A1 | 8/2008 | Segawa et al. | | 2009/0322864 A1 | 12/2009 | Karasawa et al. |
| 2008/0188868 A1 | 8/2008 | Weitzner et al. | | 2009/0326332 A1 | 12/2009 | Carter |
| 2008/0200755 A1 | 8/2008 | Bakos | | 2009/0326561 A1 | 12/2009 | Carroll, II et al. |
| 2008/0200762 A1 | 8/2008 | Stokes et al. | | 2010/0010294 A1 | 1/2010 | Conlon et al. |
| 2008/0200911 A1 | 8/2008 | Long | | 2010/0010298 A1 | 1/2010 | Bakos et al. |
| 2008/0200912 A1 | 8/2008 | Long | | 2010/0010299 A1 | 1/2010 | Bakos et al. |
| 2008/0200933 A1 | 8/2008 | Bakos et al. | | 2010/0010303 A1 | 1/2010 | Bakos |
| 2008/0200934 A1 | 8/2008 | Fox | | 2010/0010510 A1 | 1/2010 | Stefanchik |
| 2008/0208213 A1 | 8/2008 | Benjamin et al. | | 2010/0010511 A1 | 1/2010 | Harris et al. |
| 2008/0221587 A1 | 9/2008 | Schwartz | | 2010/0023032 A1 | 1/2010 | Granja Filho |
| 2008/0221619 A1 | 9/2008 | Spivey et al. | | 2010/0030211 A1 | 2/2010 | Davalos et al. |
| 2008/0228213 A1 | 9/2008 | Blakeney et al. | | 2010/0036198 A1 | 2/2010 | Tacchino et al. |

| | | | | | | |
|---|---|---|---|---|---|---|
| 2010/0042045 A1 | 2/2010 | Spivey | EP | 0724863 B1 | 7/1999 | |
| 2010/0048990 A1 | 2/2010 | Bakos | EP | 0760629 B1 | 11/1999 | |
| 2010/0049190 A1 | 2/2010 | Long et al. | EP | 0818974 B1 | 7/2001 | |
| 2010/0049223 A1 | 2/2010 | Granja Filho | EP | 1281356 A2 | 2/2003 | |
| 2010/0056861 A1 | 3/2010 | Spivey | EP | 0947166 B1 | 5/2003 | |
| 2010/0056862 A1 | 3/2010 | Bakos | EP | 0836832 B1 | 12/2003 | |
| 2010/0056864 A1 | 3/2010 | Lee | EP | 1402837 A1 | 3/2004 | |
| 2010/0057108 A1 | 3/2010 | Spivey et al. | EP | 0744918 B1 | 4/2004 | |
| 2010/0063538 A1 | 3/2010 | Spivey et al. | EP | 0931515 B1 | 8/2004 | |
| 2010/0076451 A1 | 3/2010 | Zwolinski et al. | EP | 0941128 B1 | 10/2004 | |
| 2010/0081877 A1 | 4/2010 | Vakharia | EP | 1411843 B1 | 10/2004 | |
| 2010/0087813 A1 | 4/2010 | Long | EP | 1150614 B1 | 11/2004 | |
| 2010/0113872 A1 | 5/2010 | Asada et al. | EP | 1477104 A1 | 11/2004 | |
| 2010/0121362 A1 | 5/2010 | Clague et al. | EP | 1481642 A1 | 12/2004 | |
| 2010/0130817 A1 | 5/2010 | Conlon | EP | 1493391 A1 | 1/2005 | |
| 2010/0130975 A1 | 5/2010 | Long | EP | 0848598 B1 | 2/2005 | |
| 2010/0131005 A1 | 5/2010 | Conlon | EP | 1281360 B1 | 3/2005 | |
| 2010/0152539 A1 | 6/2010 | Ghabrial et al. | EP | 1568330 A1 | 8/2005 | |
| 2010/0152609 A1 | 6/2010 | Zwolinski et al. | EP | 1452143 B1 | 9/2005 | |
| 2010/0152746 A1 | 6/2010 | Ceniccola et al. | EP | 1616527 A2 | 1/2006 | |
| 2010/0179510 A1 | 7/2010 | Fox et al. | EP | 1006888 B1 | 3/2006 | |
| 2010/0179530 A1 | 7/2010 | Long et al. | EP | 1629764 A1 | 3/2006 | |
| 2010/0191050 A1 | 7/2010 | Zwolinski | EP | 1013229 B1 | 6/2006 | |
| 2010/0191075 A1 | 7/2010 | Angelides | EP | 1721561 A1 | 11/2006 | |
| 2010/0191267 A1 | 7/2010 | Fox | EP | 1153578 B1 | 3/2007 | |
| 2010/0198005 A1 | 8/2010 | Fox | EP | 1334696 B1 | 3/2007 | |
| 2010/0198149 A1 | 8/2010 | Fox | EP | 1769766 A1 | 4/2007 | |
| 2010/0198244 A1 | 8/2010 | Spivey et al. | EP | 1836971 A2 | 9/2007 | |
| 2010/0198248 A1 | 8/2010 | Vakharia | EP | 1836980 A1 | 9/2007 | |
| 2010/0249700 A1 | 9/2010 | Spivey | EP | 1854421 A2 | 11/2007 | |
| 2010/0261994 A1 | 10/2010 | Davalos et al. | EP | 1857061 A1 | 11/2007 | |
| 2010/0286791 A1 | 11/2010 | Goldsmith | EP | 1875876 A1 | 1/2008 | |
| 2010/0298642 A1 | 11/2010 | Trusty et al. | EP | 1891881 A1 | 2/2008 | |
| 2010/0312056 A1 | 12/2010 | Galperin et al. | EP | 1902663 A1 | 3/2008 | |
| 2010/0331622 A2 | 12/2010 | Conlon | EP | 1477106 B1 | 6/2008 | |
| 2010/0331758 A1 | 12/2010 | Davalos et al. | EP | 1949844 A1 | 7/2008 | |
| 2010/0331774 A2 | 12/2010 | Spivey | EP | 1518499 B1 | 8/2008 | |
| 2011/0093009 A1 | 4/2011 | Fox | EP | 1582138 B1 | 9/2008 | |
| 2011/0098694 A1 | 4/2011 | Long | EP | 1709918 B1 | 10/2008 | |
| 2011/0098704 A1 | 4/2011 | Long et al. | EP | 1985226 A2 | 10/2008 | |
| 2011/0105850 A1 | 5/2011 | Voegele et al. | EP | 1994904 A1 | 11/2008 | |
| 2011/0106221 A1 | 5/2011 | Neal, II et al. | EP | 1707130 B1 | 12/2008 | |
| 2011/0112434 A1 | 5/2011 | Ghabrial et al. | EP | 0723462 B1 | 3/2009 | |
| 2011/0115891 A1 | 5/2011 | Trusty | EP | 1769749 B1 | 11/2009 | |
| 2011/0124964 A1 | 5/2011 | Nobis | EP | 1493397 B1 | 9/2011 | |
| 2011/0152609 A1 | 6/2011 | Trusty et al. | FR | 2731610 A1 | 9/1996 | |
| 2011/0152610 A1 | 6/2011 | Trusty et al. | GB | 330629 A | 6/1930 | |
| 2011/0152612 A1 | 6/2011 | Trusty et al. | GB | 2335860 A | 10/1999 | |
| 2011/0152858 A1 | 6/2011 | Long et al. | GB | 2403909 A | 1/2005 | |
| 2011/0152859 A1 | 6/2011 | Long et al. | GB | 2421190 A | 6/2006 | |
| 2011/0152878 A1 | 6/2011 | Trusty et al. | GB | 2443261 A | 4/2008 | |
| 2011/0152923 A1 | 6/2011 | Fox | JP | 56-46674 | 4/1981 | |
| 2011/0160514 A1 | 6/2011 | Long et al. | JP | 63309252 A | 12/1988 | |
| 2011/0190659 A1 | 8/2011 | Long et al. | JP | 4038960 A | 2/1992 | |
| 2011/0190764 A1 | 8/2011 | Long et al. | JP | 8-29699 A | 2/1996 | |
| 2011/0193948 A1 | 8/2011 | Amling et al. | JP | 2000245683 A | 9/2000 | |
| 2011/0245619 A1 | 10/2011 | Holcomb | JP | 2002-369791 A | 12/2002 | |
| 2011/0285488 A1 | 11/2011 | Scott et al. | JP | 2003-088494 A | 3/2003 | |
| 2011/0306971 A1 | 12/2011 | Long | JP | 2003-235852 A | 8/2003 | |
| 2012/0004502 A1 | 1/2012 | Weitzner et al. | JP | 2004-33525 A | 2/2004 | |
| 2012/0088965 A1 | 4/2012 | Stokes et al. | JP | 2004-065745 A | 3/2004 | |
| 2012/0089089 A1 | 4/2012 | Swain et al. | JP | 2005-121947 A | 5/2005 | |
| 2012/0089093 A1 | 4/2012 | Trusty | JP | 2005-261514 A | 9/2005 | |
| 2012/0116155 A1 | 5/2012 | Trusty | JP | 2006297005 A | 11/2006 | |
| 2012/0179148 A1 | 7/2012 | Conlon | NL | 1021295 C2 | 2/2004 | |
| 2012/0191076 A1 | 7/2012 | Voegele et al. | SU | 194230 | 5/1967 | |
| 2012/0220998 A1 | 8/2012 | Long et al. | SU | 980703 | 12/1982 | |
| 2012/0220999 A1 | 8/2012 | Long | WO | WO 84/01707 A1 | 5/1984 | |
| 2012/0221002 A1 | 8/2012 | Long et al. | WO | WO 92/13494 A1 | 8/1992 | |
| | | | WO | WO 93/10850 A1 | 6/1993 | |
| FOREIGN PATENT DOCUMENTS | | | WO | WO 93/20760 A1 | 10/1993 | |
| DE | 19713797 A1 | 10/1997 | WO | WO 93/20765 A1 | 10/1993 | |
| DE | 19757056 B4 | 8/2008 | WO | WO 95/09666 A1 | 4/1995 | |
| DE | 102006027873 B4 | 10/2009 | WO | WO 96/22056 A1 | 7/1996 | |
| EP | 0086338 A1 | 8/1983 | WO | WO 96/27331 A1 | 9/1996 | |
| EP | 0286415 A2 | 10/1988 | WO | WO 96/39946 A1 | 12/1996 | |
| EP | 0589454 A2 | 3/1994 | WO | WO 97/12557 A1 | 4/1997 | |
| EP | 0464479 B1 | 3/1995 | WO | WO 98/01080 A1 | 1/1998 | |
| EP | 0529675 B1 | 2/1996 | WO | WO 99/00060 A1 | 1/1999 | |

| | | |
|---|---|---|
| WO | WO 99/09919 A1 | 3/1999 |
| WO | WO 99/17661 A1 | 4/1999 |
| WO | WO 99/30622 A2 | 6/1999 |
| WO | WO 00/35358 A1 | 6/2000 |
| WO | WO 01/10319 A1 | 2/2001 |
| WO | WO 01/26708 A1 | 4/2001 |
| WO | WO 01/41627 A2 | 6/2001 |
| WO | WO 01/58360 A2 | 8/2001 |
| WO | WO 02/11621 A1 | 2/2002 |
| WO | WO 02/34122 A2 | 5/2002 |
| WO | WO 02/094082 A2 | 11/2002 |
| WO | WO 03/045260 A1 | 6/2003 |
| WO | WO 03/047684 A2 | 6/2003 |
| WO | WO 03/059412 A2 | 7/2003 |
| WO | WO 03/078721 A2 | 9/2003 |
| WO | WO 03/081761 A2 | 10/2003 |
| WO | WO 03/082129 A2 | 10/2003 |
| WO | WO 2004/006789 A1 | 1/2004 |
| WO | WO 2004/028613 A2 | 4/2004 |
| WO | WO 2004/037123 A1 | 5/2004 |
| WO | WO 2004/037149 A1 | 5/2004 |
| WO | WO 2004/052221 A1 | 6/2004 |
| WO | WO 2004/086984 A1 | 10/2004 |
| WO | WO 2005/009211 A2 | 2/2005 |
| WO | WO 2005/018467 A2 | 3/2005 |
| WO | WO 2005/037088 A2 | 4/2005 |
| WO | WO 2005/048827 A1 | 6/2005 |
| WO | WO 2005/065284 A2 | 7/2005 |
| WO | WO 2005/097019 A2 | 10/2005 |
| WO | WO 2005/097234 A2 | 10/2005 |
| WO | WO 2005/112810 A2 | 12/2005 |
| WO | WO 2005/120363 A1 | 12/2005 |
| WO | WO 2005/122866 A1 | 12/2005 |
| WO | WO 2006/007399 A1 | 1/2006 |
| WO | WO 2006/012630 A2 | 2/2006 |
| WO | WO 2006/040109 A1 | 4/2006 |
| WO | WO 2006/041881 A2 | 4/2006 |
| WO | WO 2006/060405 A2 | 6/2006 |
| WO | WO 2006/110733 A2 | 10/2006 |
| WO | WO 2006/113216 A2 | 10/2006 |
| WO | WO 2007/013059 A2 | 2/2007 |
| WO | WO 2007/014063 A2 | 2/2007 |
| WO | WO 2007/048085 A2 | 4/2007 |
| WO | WO 2007/063550 A2 | 6/2007 |
| WO | WO 2007/100067 A1 | 9/2007 |
| WO | WO 2007/109171 A2 | 9/2007 |
| WO | WO 2008/005433 A1 | 1/2008 |
| WO | WO 2008/033356 A2 | 3/2008 |
| WO | WO 2008/041225 A2 | 4/2008 |
| WO | WO 2008/076337 A1 | 6/2008 |
| WO | WO 2008/076800 A2 | 6/2008 |
| WO | WO 2008/079440 A2 | 7/2008 |
| WO | WO 2008/101075 A2 | 8/2008 |
| WO | WO 2008/102154 A2 | 8/2008 |
| WO | WO 2008/108863 A2 | 9/2008 |
| WO | WO 2008/151237 A1 | 12/2008 |
| WO | WO 2009/021030 A1 | 2/2009 |
| WO | WO 2009/027065 A1 | 3/2009 |
| WO | WO 2009/029065 A1 | 3/2009 |
| WO | WO 2009/032623 A2 | 3/2009 |
| WO | WO 2009/121017 A1 | 10/2009 |
| WO | WO 2010/027688 A1 | 3/2010 |
| WO | WO 2010/056716 A2 | 5/2010 |
| WO | WO 2010/080974 A1 | 7/2010 |
| WO | WO 2010/088481 A1 | 8/2010 |

OTHER PUBLICATIONS

Zadno et al., "Linear Superelasticity in Cold-Worked NI-TI," Engineering Aspects of Shape Memory Alloys, pp. 414-419.
U.S. Appl. No. 12/752,701, filed Apr. 1, 2010.
U.S. Appl. No. 11/897,676, filed Aug. 31, 2007.
U.S. App. No. 11/744,271, filed May 4, 2007.
U.S. Appl. No. 11/744,279, filed May 4, 2007.
U.S. Appl. No. 11/796,035, filed Apr. 26, 2007.
U.S. Appl. No. 11/796,357, filed Apr. 27, 2007.
U.S. Appl. No. 11/894,358, filed Aug. 21, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489 filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 11/762,855, filed Jun. 14, 2007.
U.S. Appl. No. 12/192,372, filed Aug. 15, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9, 2008.
U.S. Appl. No. 12/243,334, filed Oct. 1, 2008.
U.S. Appl. No. 12/234,425, filed Sep. 19, 2008.
U.S. Appl. No. 11/756,914, filed Jun. 1, 2007.
U.S. Appl. No. 12/060,601, filed Apr. 1, 2008.
Partial International Search Report for PCT/US2009/055140, Nov. 17, 2009 (2 pages).
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.
U.S. Appl. No. 12/413,479, filed Mar. 27, 2009.
U.S. Appl. No. 12/468,462, filed May 19, 2009.
U.S. Appl. No. 12/607,252, filed Oct. 28, 2009.
U.S. Appl. No. 12/580,400, filed Oct. 16, 2009.
U.S. Appl. No. 12/607,388, filed Oct. 28, 2009.
U.S. Appl. No. 12/612,911, filed Nov. 5, 2009.
U.S. Appl. No. 12/614,143, filed Nov. 6, 2009.
U.S. Appl. No. 12/617,998, filed Nov. 13, 2009.
U.S. Appl. No. 12/635,298, filed Dec. 10, 2009.
U.S. Appl. No. 12/640,440, filed Dec. 17, 2009.
U.S. Appl. No. 12/640,469, filed Dec. 17, 2009.
U.S. Appl. No. 12/640,476, filed Dec. 17, 2009.
U.S. Appl. No. 12/640,492, filed Dec. 17, 2009.
U.S. Appl. No. 12/641,823, filed Dec. 18, 2009.
U.S. Appl. No. 12/641,853, filed Dec. 18, 2009.
U.S. Appl. No. 12/641,837, filed Dec. 18, 2009.
U.S. Appl. No. 12/651,181, filed Dec. 31, 2009.
U.S. Appl. No. 12/696,598, filed Jan. 29, 2010.
U.S. Appl. No. 12/696,626, filed Jan. 29, 2010.
Written Opinion for PCT/US2009/055140, Mar. 23, 2010 (11 pages).
Zadno et al., "Linear Superelasticity in Cold-Worked NI-TI," Engineering Aspects of Shape Memory Alloys, pp. 414-419 (1990).
U.S. Appl. No. 13/013,131, filed Jan. 25, 2011.

U.S. Appl. No. 13/013,147, filed Jan. 25, 2011.
U.S. Appl. No. 12/900,132, filed Oct. 7, 2010.
U.S. Appl. No. 12/939,441, filed Nov. 4, 2010.
U.S. Appl. No. 12/902,531, filed Oct. 12, 2010.
U.S. Appl. No. 12/902,550, filed Oct. 12, 2010.
How Stuff Works "How Smart Structures Will Work," http://science.howstuffworks.com/engineering/structural/smart-structure1.htm; accessed online Nov. 1, 2011 (3 pages).
Instant Armor: Science Videos—Science News—ScienCentral; http://www.sciencentral.com/articles./view.php3?article_id=218392121; accessed online Nov. 1, 2011 (2 pages).
Stanway, Smart Fluids: Current and Future Developments. Material Science and Technology, 20, pp. 931-939, 2004; accessed online Nov. 1, 2011 at http://www.dynamics.group.shef.ac.uk/smart/smart.html (7 pages).
Jolly et al., Properties and Applications of Commercial Magnetorheological Fluids. SPIE 5th Annual Int. Symposium on Smart Structures and Materials, 1998 (18 pages).
U.S. Appl. No. 13/036,895, filed Feb. 28, 2011.
U.S. Appl. No. 13/036,908, filed Feb. 28, 2011.
U.S. Appl. No. 13/267,251, filed Oct. 6, 2011.
U.S. Appl. No. 13/325,791, filed Dec. 14, 2011.
U.S. Appl. No. 13/352,495, filed Jan. 18, 2012.
U.S. Appl. No. 13/399,358, filed Feb. 17, 2012.
U.S. Appl. No. 13/420,805, filed Mar. 15, 2012.
U.S. Appl. No. 13/420,818, filed Mar. 15, 2012.
J.D. Paulson, M.D., et al., "Development of Flexible Culdoscopy," The Journal of the American Association of Gynecologic Laparoscopists, Nov. 1999, vol. 6, No. 4, pp. 487-490.
H. Seifert, et al., "Retroperitoneal Endoscopic Debridement for Infected Peripancreatic Necrosis," The Lancet, Research Letters, vol. 356, Aug. 19, 2000, pp. 653-655.
K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).
D. Wilhelm et al., "An Innovative, Safe and Sterile Sigmoid Access (ISSA) for NOTES," Endoscopy 2007, vol. 39, pp. 401-406.
Nakazawa et al., "Radiofrequency Ablation of Hepatocellular Carcinoma: Correlation Between Local Tumor Progression After Ablation and Ablative Margin," AJR, 188, pp. 480-488 (Feb. 2007).
Miklavčičič et al., "A validated model of in vivo electric field distribution in tissues for electrochemotherapy and for DNA electrotransfer for gene therapy," Biochimica et Biophysica Acta, 1523, pp. 73-83 (2000).
Evans, "Ablative and cathether-delivered therapies for colorectal liver metastases (CRLM)," EJSO, 33, pp. S64-S75 (2007).
Wong et al., "Combined Percutaneous Radiofrequency Ablation and Ethanol Injection for Hepatocellular Carcinoma in High-Risk Locations," AJR, 190, pp. W187-W195 (2008).
Heller et al., "Electrically mediated plasmid DNA delivery to hepatocellular carcinomas in vivo," Gene Therapy, 7, pp. 826-829 (2000).
Widera et al., "Increased DNA Vaccine Delivery and Immunogenicity by Electroporation in Vivo," The Journal of Immunology, 164, pp. 4635-4640 (2000).
Weaver et al., "Theory of electroporation: A review," Bioelectrochemistry and Bioenergetics, 41, pp. 135-160 (1996).
Muller et al., "Radiofrequency Ablation Versus Resection for Resectable Colorectal Liver Metastases: Time for a Randomized Trial?" Annals of Surgical Oncology, 15(1), pp. 144-157 (2008).
Link et al., "Regional Chemotherapy of Nonresectable Colorectal Liver Metastases with Mitoxanthrone, 5-Fluorouracil, Folinic Acid, and Mitomycin C May Prolong Survival," Cancer, 92, pp. 2746-2753 (2001).
Guyton et al., "Membrane Potentials and Action Potentials," W.B. Sanders, ed. Textbook of Medical Physiology, p. 56 (2000).
Guyton et al., "Contraction of Skeletal Muscle," Textbook of Medical Physiology, pp. 82-84 (2000).
"Ethicon Endo-Surgery Novel Investigational Notes and SSL Devices Featured in 15 Presentations at Sages," Apr. 22, 2009 Press Release; URL http://www.jnj.com/connect/news/all/20090422_152000; accessed Aug. 28, 2009 (3 pages).

"Ethicon Endo-Surgery Studies Presented at DDW Demonstrate Potential of Pure NOTES Surgery With Company's Toolbox," Jun. 3, 2009 Press Release; URL http://www.jnj.com/connect/news/product/20090603_120000; accessed Aug. 28, 2009 (3 pages).
Castellvi et al., "Hybrid Transvaginal NOTES Sleeve Gastrectomy in a Porcine Model Using a Magnetically Anchored Camera and Novel Instrumentation," Abstract submitted along with Poster at SAGES Annual Meeting in Phoenix, AZ, Apr. 22, 2009 (1 page).
Castellvi et al., "Hybrid Transvaginal NOTES Sleeve Gastrectomy in a Porcine Model Using a Magnetically Anchored Camera and Novel Instrumentation," Poster submitted along with Abstract at SAGES Annual Meeting in Phoenix, AZ, Apr. 22, 2009 (1 page).
OCTO Port Modular Laparoscopy System for Single Incision Access, Jan. 4, 2010; URL http://www.medgadget.com/archives/2010/01/octo_port_modular_laparo . . . ; accessed Jan. 5, 2010 (4 pages).
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
Michael S. Kavic, M.D., "Natural Orifice Translumenal Endoscopic Surgery: "NOTES"", JSLS, vol. 10, pp. 133-134 (2006).
Ethicon, Inc., "Wound Closure Manual: Chapter 3 (The Surgical Needle)," 15 pages, (publication date unknown).
Guido M. Sclabas, M.D., et al., "Endoluminal Methods for Gastrotomy Closure in Natural Orifice TransEnteric Surgery (NOTES)," Surgical Innovation, vol. 13, No. 1, pp. 23-30, Mar. 2006.
Fritscher-Ravens, et al., "Transgastric Gastropexy and Hiatal Hernia Repair for GERD Under EUS Control: a Porcine Model," Gastrointestinal Endoscopy, vol. 59, No. 1, pp. 89-95, 2004.
Ogando, "Prototype Tools That Go With the Flow," Design News, 2 pages, Jul. 17, 2006.
Edd, et al., "In Vivo Results of a New Focal Tissue Ablation Technique: Irreversible Electroporation," IEEE Trans Biomed Eng, vol. 53, pp. 1409-1415, 2006.
Kennedy, et al., "High-Burst-Strength, Feedback-Controlled Bipolar Vessel Sealing," Surgical Endoscopy, vol. 12, pp. 876-878 (1998).
Collins et al., "Local Gene Therapy of Solid Tumors with GM-CSF and B7-1 Eradicates Both Treated and Distal Tumors," Cancer Gene Therapy, vol. 13, pp. 1061-1071 (2006).
K. Sumiyama et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).
K. Sumiyama et al., "Submucosal Endoscopy with Mucosal Flap Safety Valve," Gastrointest Endosc. Apr. 2007, vol. 65(4) pp. 694-695 (Abstract).
K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).
K. Sumiyama et al., "Endoscopic Caps," Tech. Gastrointest. Endosc., vol. 8, pp. 28-32, 2006.
"Z-Offset Technique Used in the Introduction of Trocar During Laparoscopic Surgery," M.S. Hershey NOTES Presentation to EES NOTES Development Team, Sep. 27, 2007.
F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).
I. Fraser, "An Historical Perspective on Mechanical Aids in Intestinal Anastamosis," Surg. Gynecol. Obstet. (Oct. 1982), vol. 155, pp. 566-574.
M.E. Ryan et al., "Endoscopic Intervention for Biliary Leaks After Laparoscopic Cholecystectomy: A Multicenter Review," Gastrointest. Endosc., vol. 47(3), 1998, pp. 261-266.
C. Cope, "Creation of Compression Gastroenterostomy by Means of the Oral, Percutaneous, or Surgical Introduction of Magnets: Feasibility Study in Swine," J. Vasc Intery Radiol , (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastomoses Achieved with Covered Stents," Gastrointest Endosc, (2001), vol. 53, pp. 780-784.

H. Okajima et al., "Magnet Compression Anastamosis for Bile Duct Stenosis After Duct to Duct Biliary Reconstruction in Living Donor Liver Transplantation," Liver Transplantation (2005), pp. 473-475.

A. Fritscher-Ravens et al., "Transluminal Endosurgery: Single Lumen Access Anastamotic Device for Flexible Endoscopy," Gastrointestinal Endosc, (2003), vol. 58(4), pp. 585-591.

G.A. Hallenbeck, M.D. et al., "An Instrument for Colorectal Anastomosis Without Sutrues," Dis Col Rectum, (1963), vol. 5, pp. 98-101.

T. Hardy, Jr., M.D. et al., "A Biofragmentable Ring for Sutureless Bowel Anastomosis. An Experimental Study," Dis Col Rectum, (1985), vol. 28, pp. 484-490.

P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedical.com/eos/components-gprox.htm—accessed May 30, 2008 (2 pages).

Printout of web page—http://www.vacumed.com/zcom/product/Product.do?compid=27&prodid=852, #51XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. (2007), pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview&navRelId=1000.1003&method=D . . . , accessed Jul. 18, 2008 (4 pages).

U.S. Appl. No. 11/744,271, filed May 4, 2007.

* cited by examiner

SURGICAL GRASPING DEVICE

BACKGROUND

In laparoscopic surgical procedures, a small incision is made in the body and an elongate shaft of a surgical device is inserted through the incision to position a distal end of the shaft at a surgical site. In endoscopic procedures, the elongate shaft of a surgical device is inserted through a natural orifice, such as the mouth or anus, and is advanced along a pathway to position a distal end of the device at a surgical site. Endoscopic procedures typically require the use of a flexible shaft to accommodate the tortuous pathway of the body lumen, whereas rigid shafts can be used in laparoscopic procedures. These tools can be used to engage and/or treat tissue in a number of ways to achieve a diagnostic or therapeutic effect.

Often during laparoscopic and endoscopic procedures, a surgeon must grasp, ablate, manipulate, dissect, or clamp soft tissue. Such actions may be performed using a plier-like tool, such as a hemostat or forceps. In some circumstances, the working end of the tool includes a first electrode and a second electrode, where one of the electrodes is brought into close opposition to the other electrode, thereby allowing an electrical current to pass between the two conductive elements. When soft tissue is captured between the two electrodes, the flowing current can cauterize, vaporize, and/or otherwise treat the soft tissue. Previous bipolar forceps, referring to U.S. Pat. No. 5,944,718, the entire disclosure of which is hereby incorporated be reference herein, have included a first electrode which can be angularly pivoted relative to a stationary second electrode. These forceps have further included a first wire attached to the first electrode where the first wire is configured to supply current to the first electrode from an electrical source. In addition, these forceps have included a second wire which is attached to the second electrode where the second wire is configured to complete the electrical circuit and return the current back to the electrical source. In some circumstances the working end of the tool includes a cutting end with a first blade member and second blade member to allow for the cutting, severing, or dissection of soft tissue. In some circumstances the working end of the tool includes a plurality of teeth to assist in the gripping of tissue.

Generally, these laparoscopic and endoscopic devices require a linkage associated with the working end of the devices which allows for user-controlled operation. The linkage allows the user to move the jaws of the working end between an open position and a closed position. An open position is when the jaws are disposed in spaced relation to one another and a closed position is wherein the jaw members cooperate to grasp tissue therebetween. These linkages used to control the movement of the jaws can often be complex requiring a multitude of small components. Additionally, in some circumstances, such linkages may not provide the desired clamping force or opening force during surgical procedures.

Accordingly, there remains a need for improved methods and devices for controlling actuation of a working end of a surgical device.

FIGURES

The novel features of the various embodiments are set forth with particularity in the appended claims. The various embodiments, however, both as to organization and methods of operation may best be understood by reference to the following description, taken in conjunction with the accompanying drawings as follows.

Figure 26A:
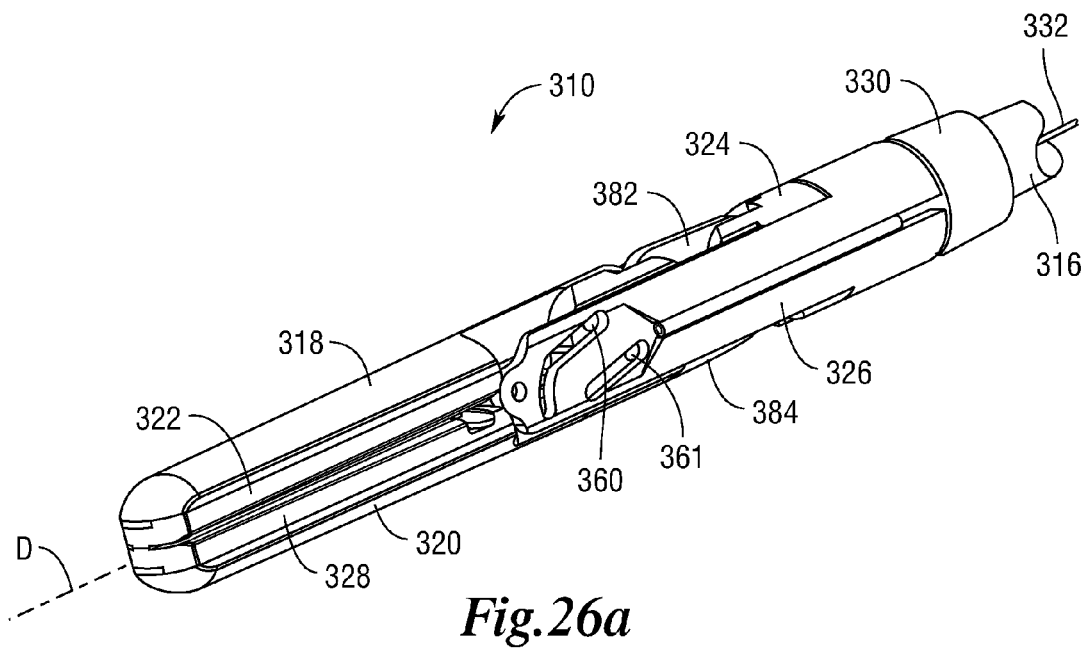
Figure 26B:
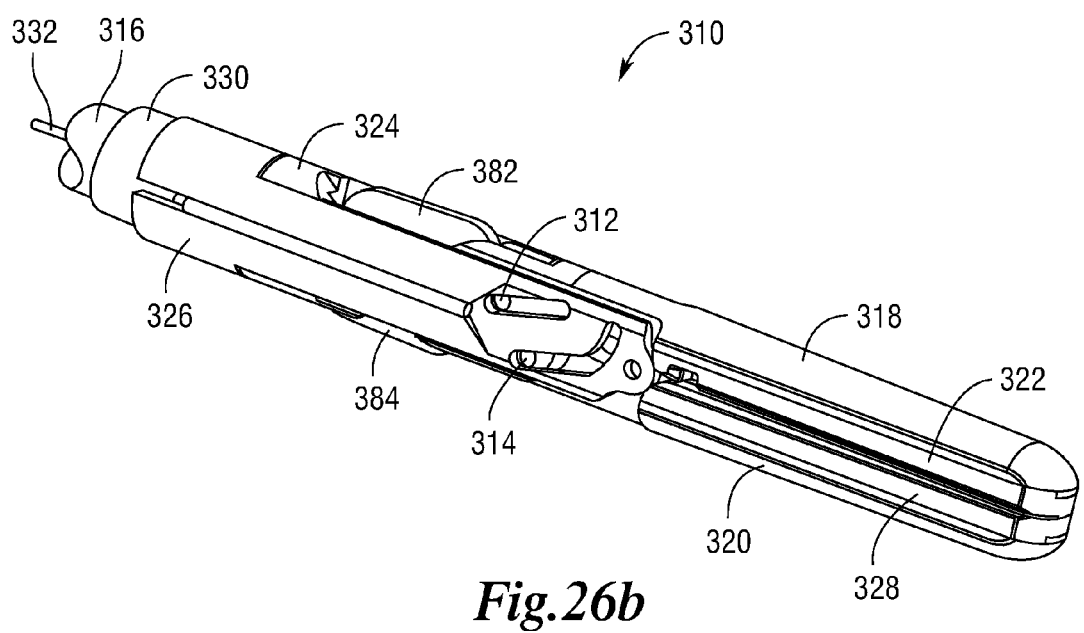

FIGS. 26a-b are perspective views of one embodiment of a surgical grasping device.

Figure 27A:
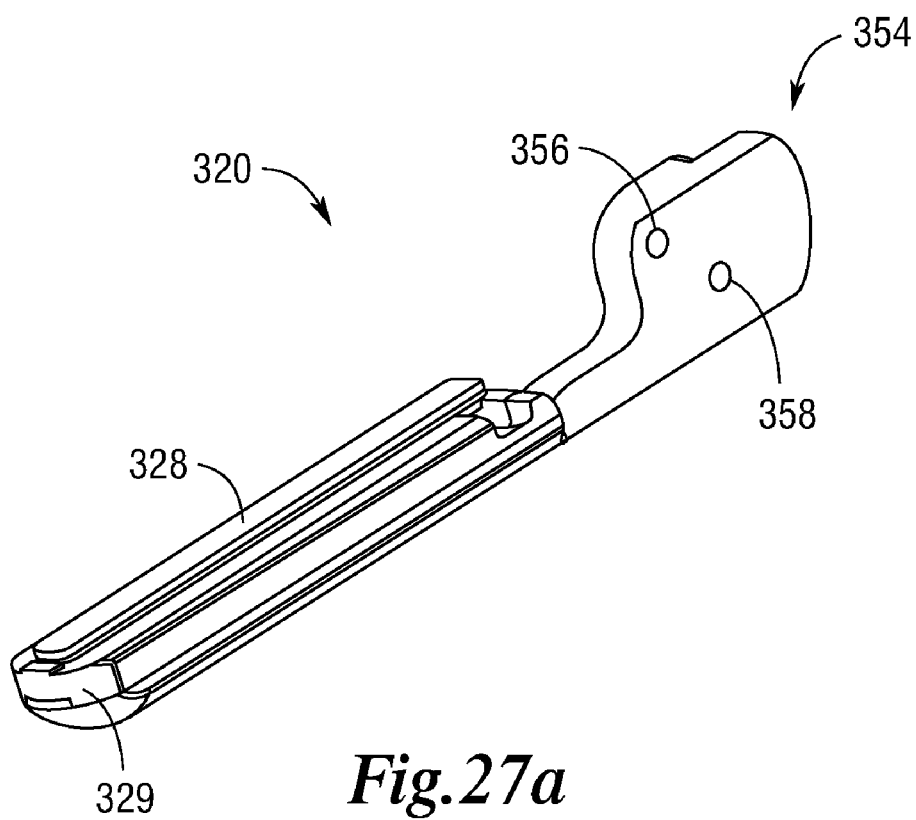
Figure 27B:
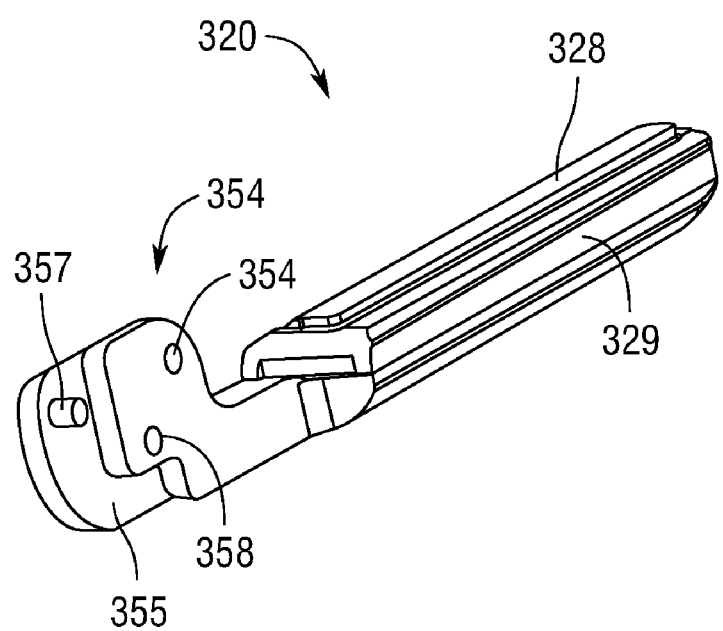

FIGS. 27a-b illustrate one embodiment of a bottom jaw of the surgical grasping device shown in FIGS. 26a-b.

Figure 28A:
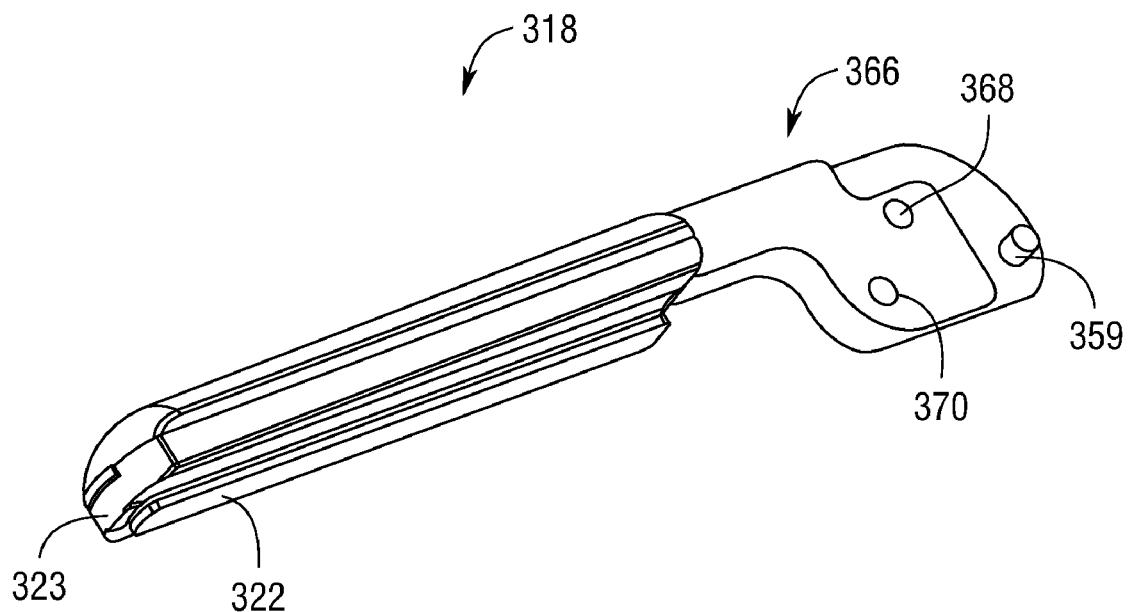
Figure 28B:
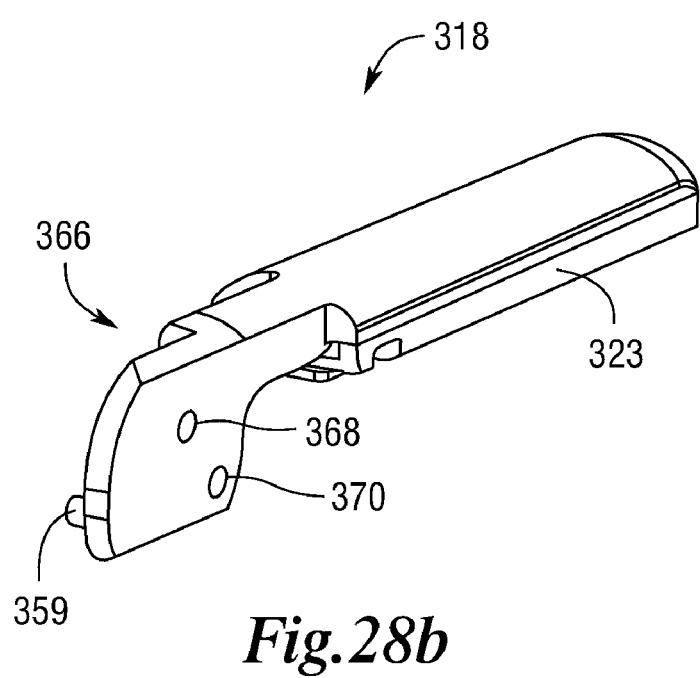

FIGS. 28a-b illustrate one embodiment of a bottom jaw of the surgical grasping device shown in FIGS. 26a-b.

Figure 29A:
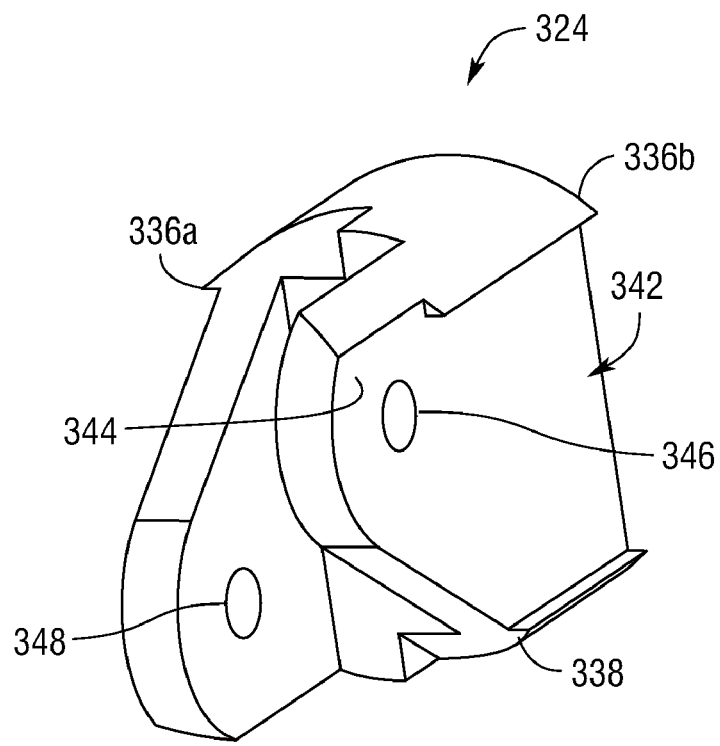
Figure 29B:
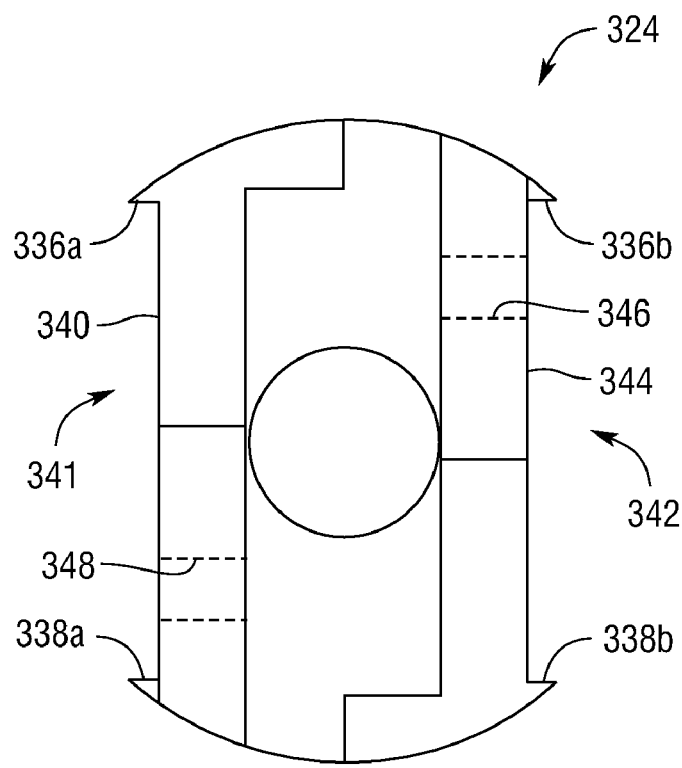

FIGS. 29a-b illustrate one embodiment of a slider of the surgical grasping device shown in FIGS. 26a-b.

Figure 30A:
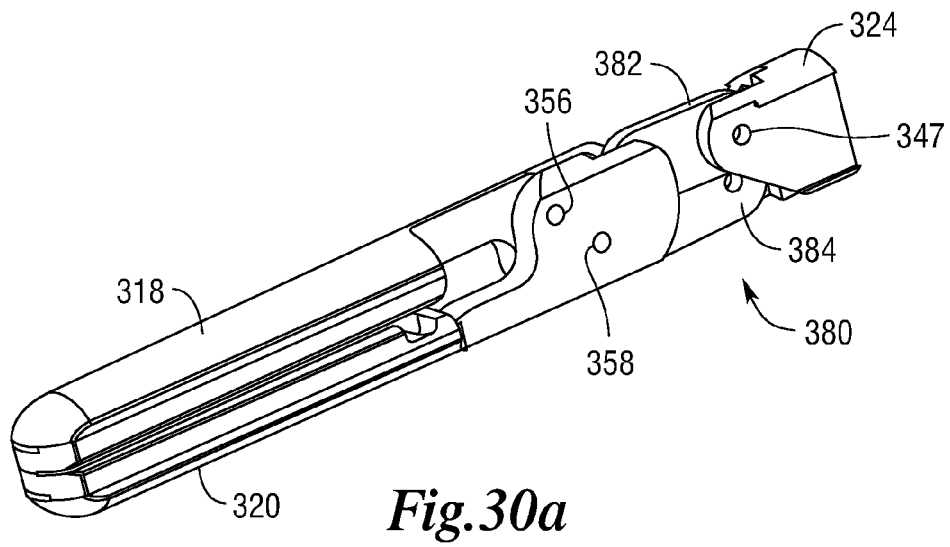
Figure 30B:
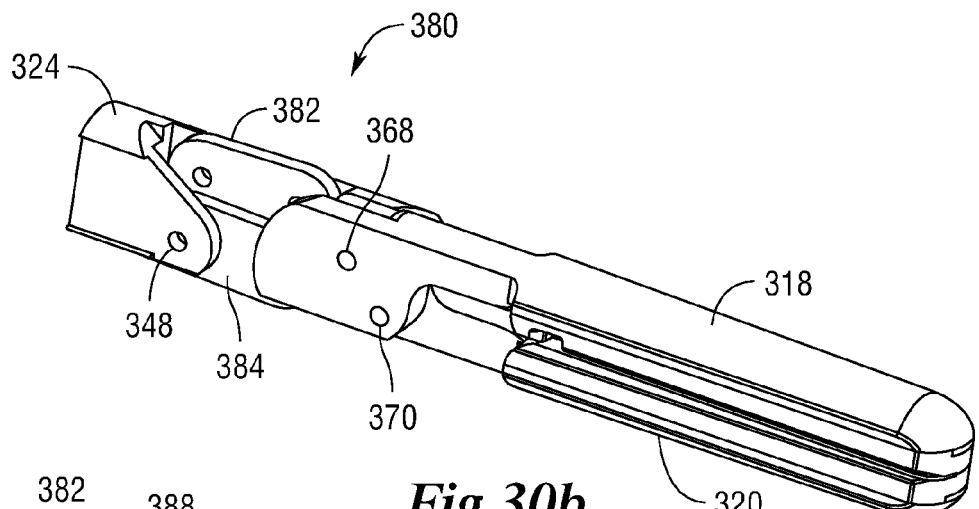
Figure 30C:
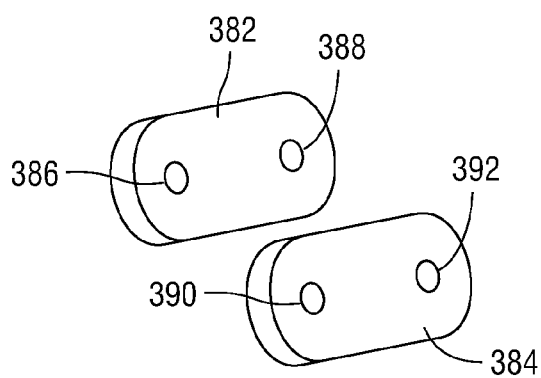

FIGS. 30a-c illustrate one embodiment of a linkage of the surgical grasping device shown in FIGS. 26a-b.

Figure 31A:
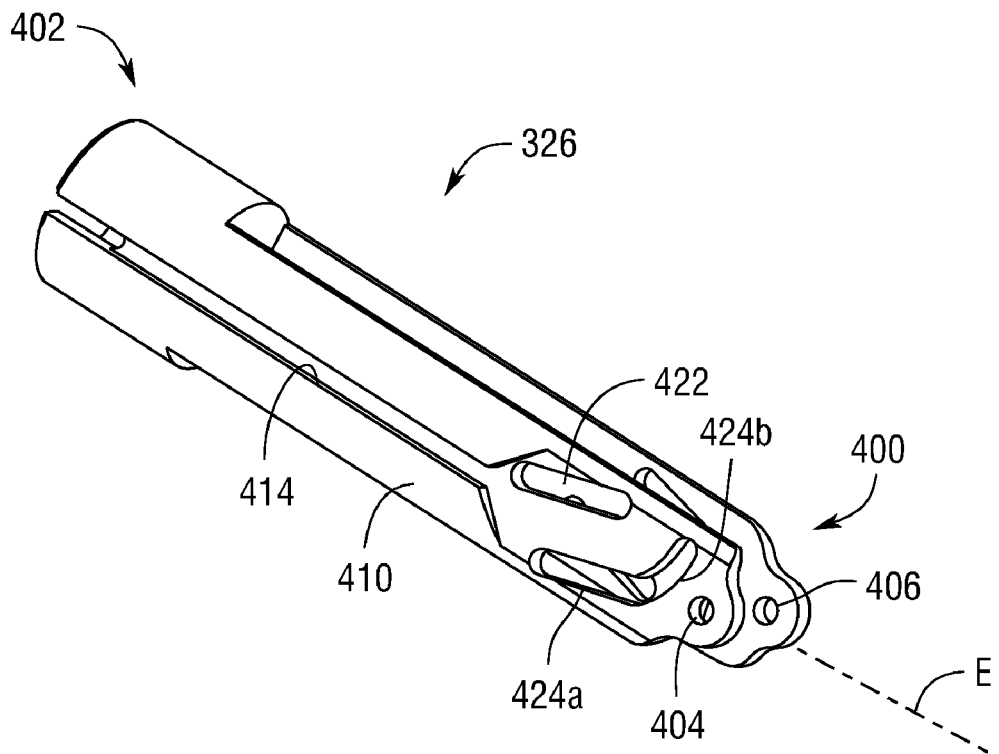
Figure 31B:
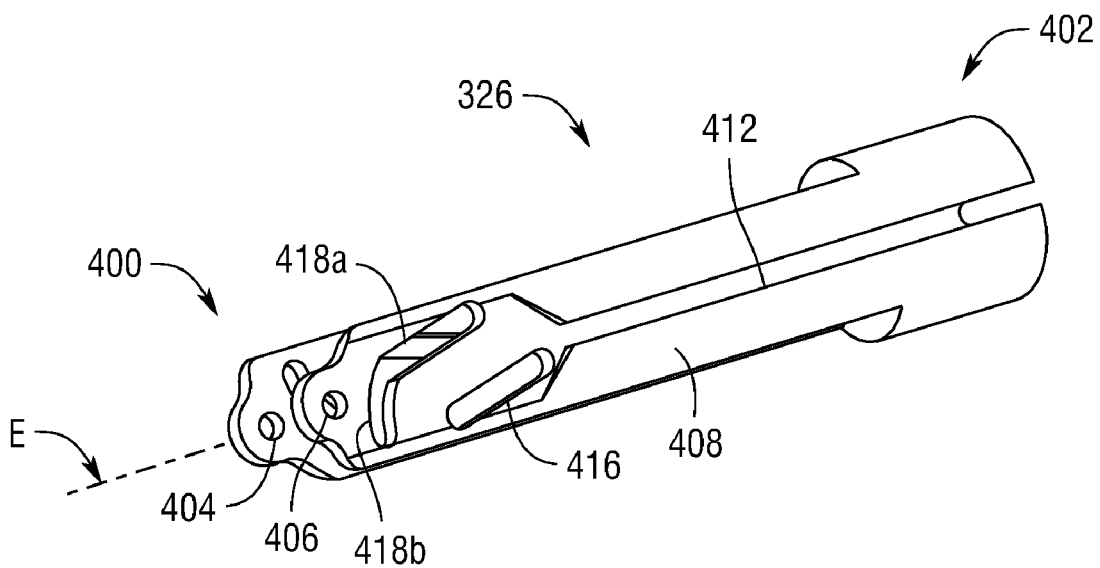

FIGS. 31a-b illustrate one embodiment of a clevis of the surgical grasping device shown in FIGS. 26a-b.

Figure 32A:
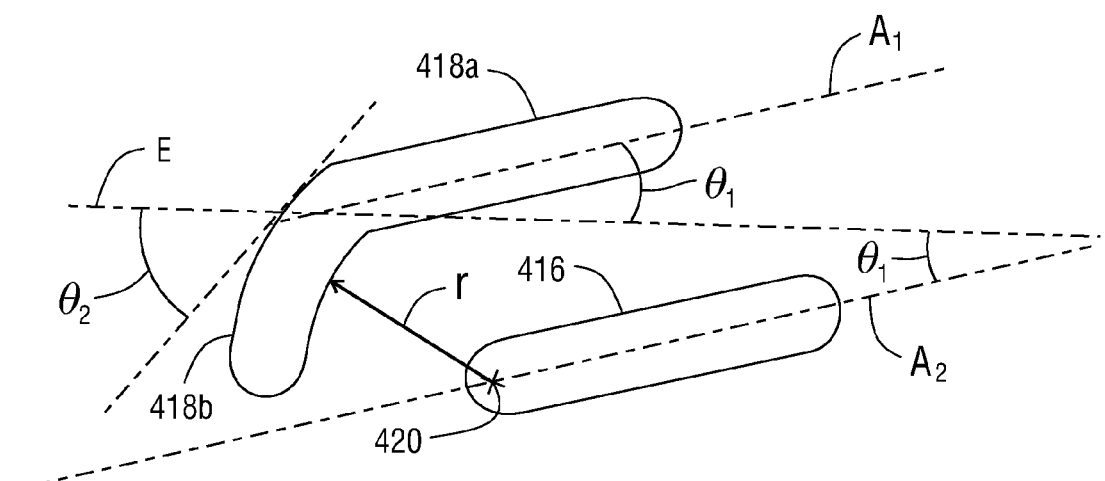
Figure 32B:
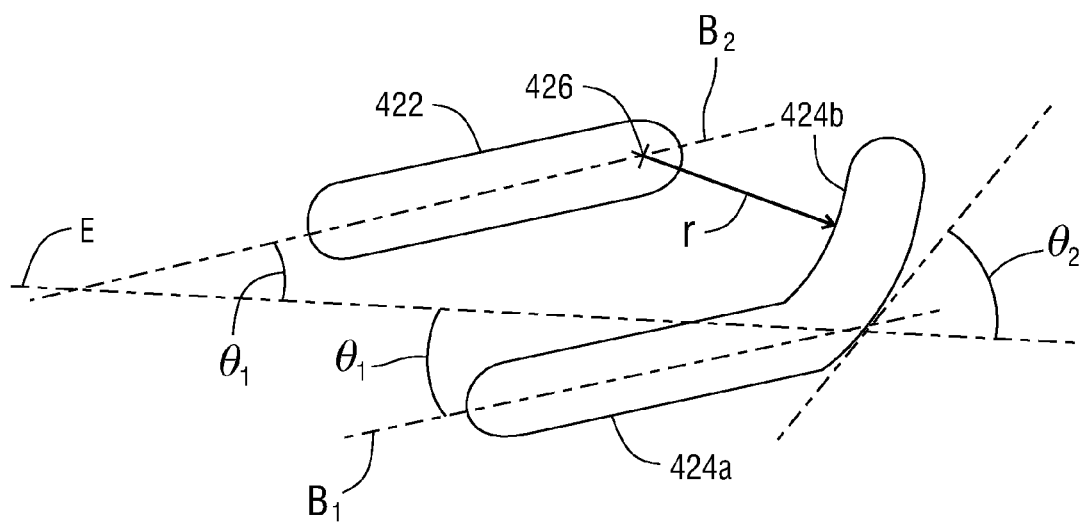

FIGS. 32a-b illustrate one embodiment of a slot configuration on the clevis shown in FIGS. 31a-b.

Figure 33:
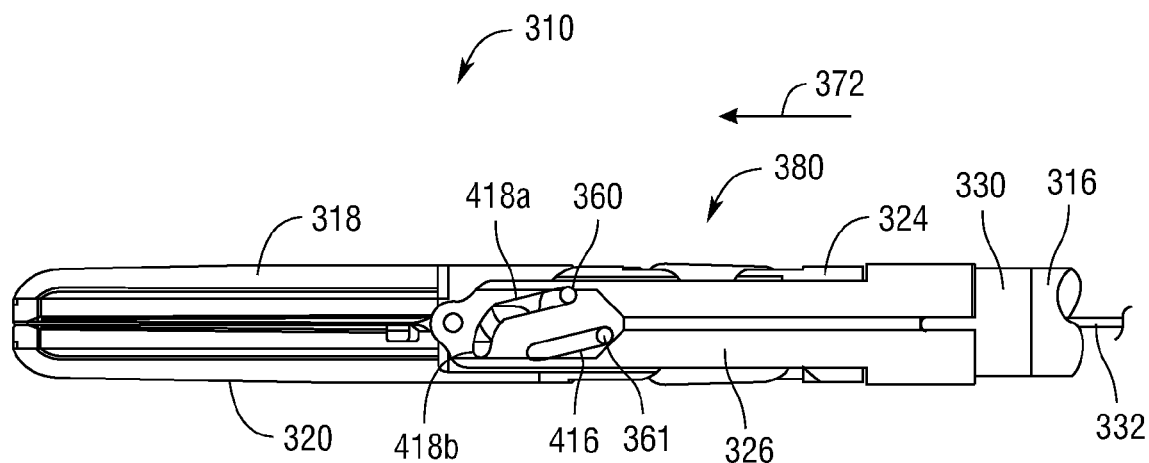

FIG. 33 is a side view of one embodiment of the surgical grasping device shown in FIGS. 26a-b.

Figure 33A:
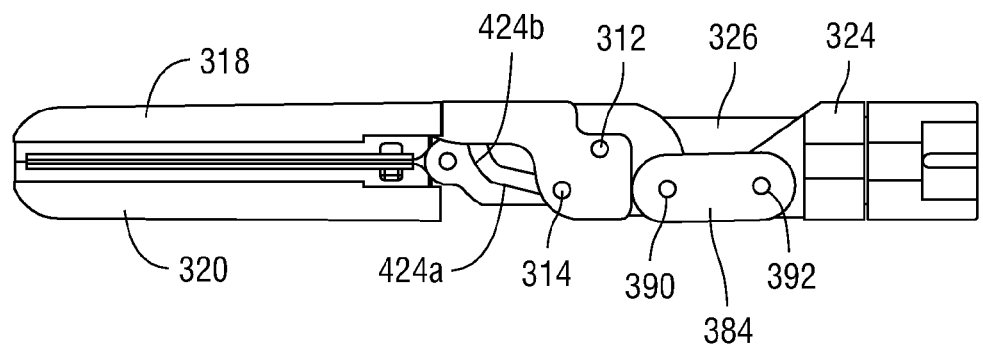

FIG. 33a is a cross-sectional view of one embodiment of the surgical grasping device shown in FIG. 33 taken along the longitudinal axis.

Figure 34:
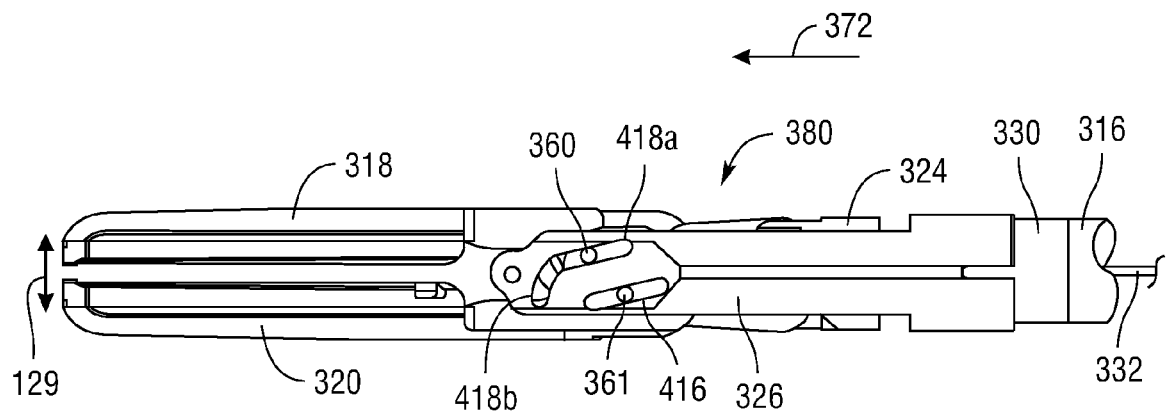

FIG. 34 is a side view of one embodiment of the surgical grasping device shown in FIGS. 26a-b.

Figure 34A:
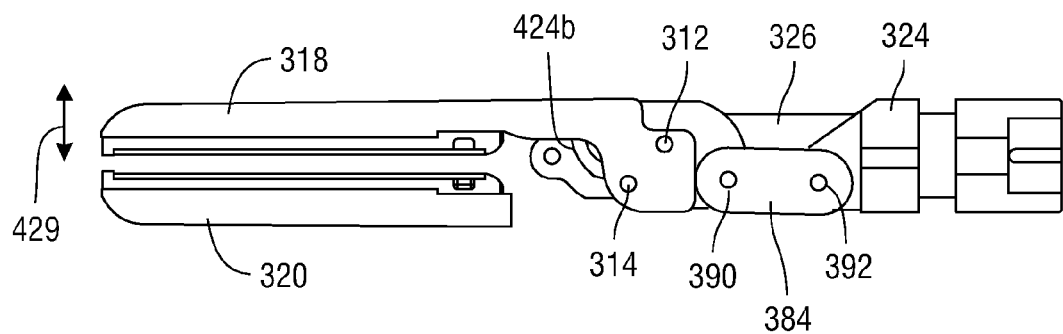

FIG. 34a is a cross-sectional view of one embodiment of the surgical grasping device shown in FIG. 34 taken along the longitudinal axis.

Figure 35:
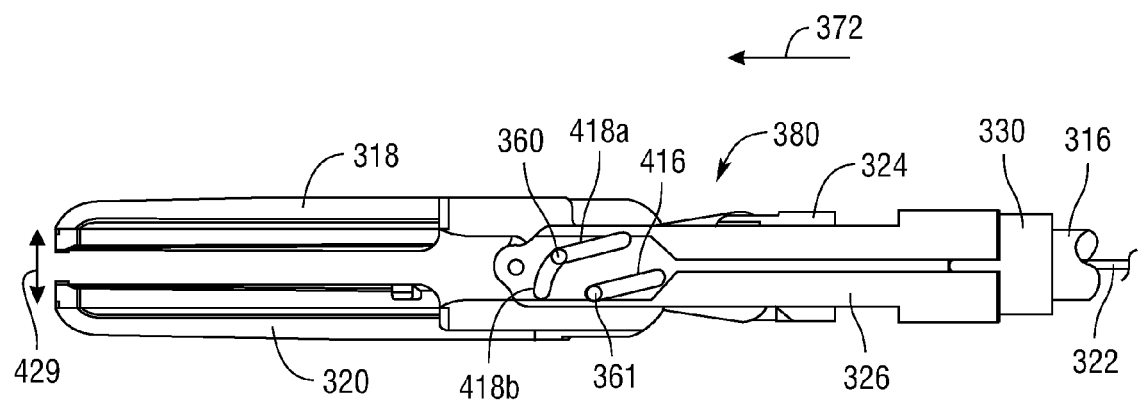

FIG. 35 is a side view of one embodiment of the surgical grasping device shown in FIGS. 26a-b.

Figure 35A:
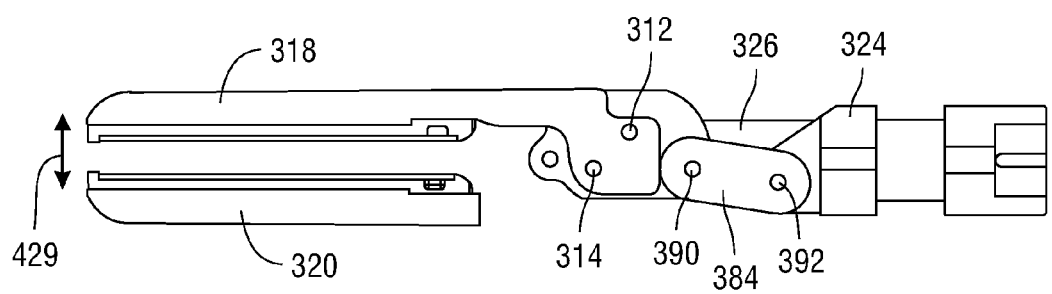

FIG. 35a is a cross-sectional view of one embodiment of the surgical grasping device shown in FIG. 35 taken along the longitudinal axis.

Figure 36:
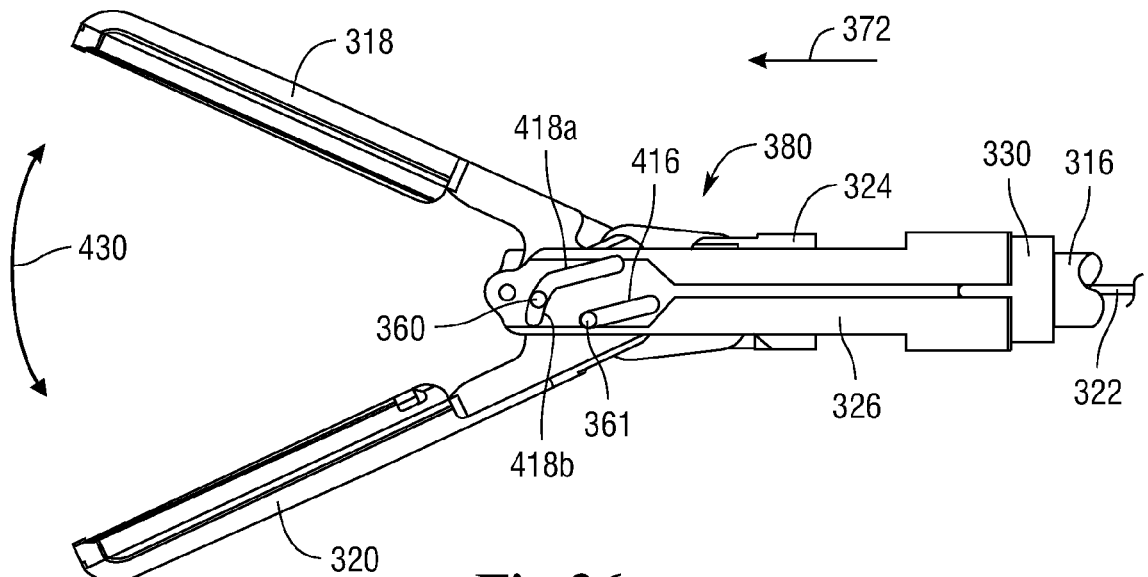

FIG. 36 is a side view of one embodiment of the surgical grasping device shown in FIGS. 26a-b.

Figure 36A:
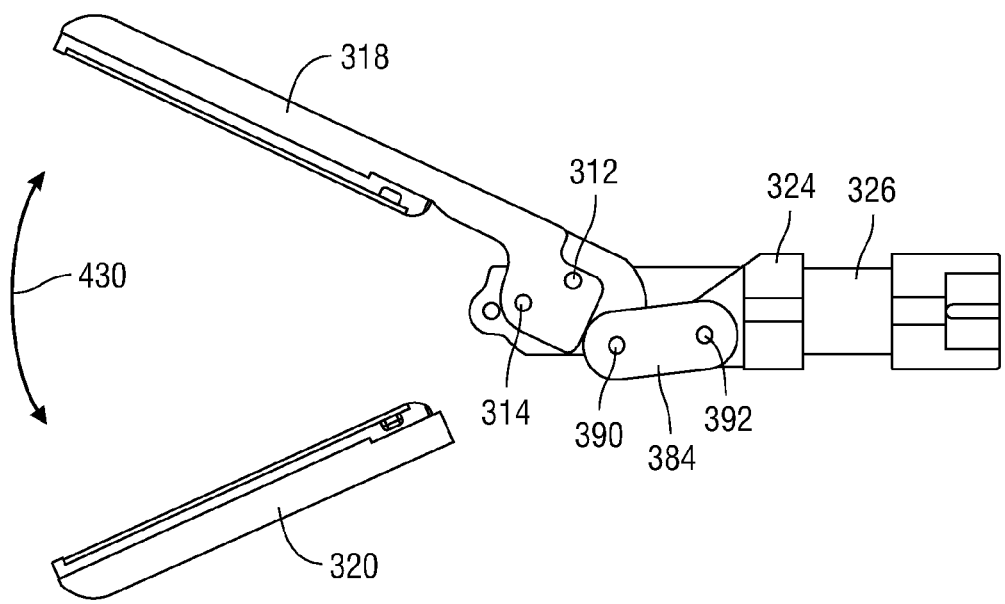

FIG. 36a is a cross-sectional view of one embodiment of the surgical grasping device shown in FIG. 36 taken along the longitudinal axis.

Figure 37:
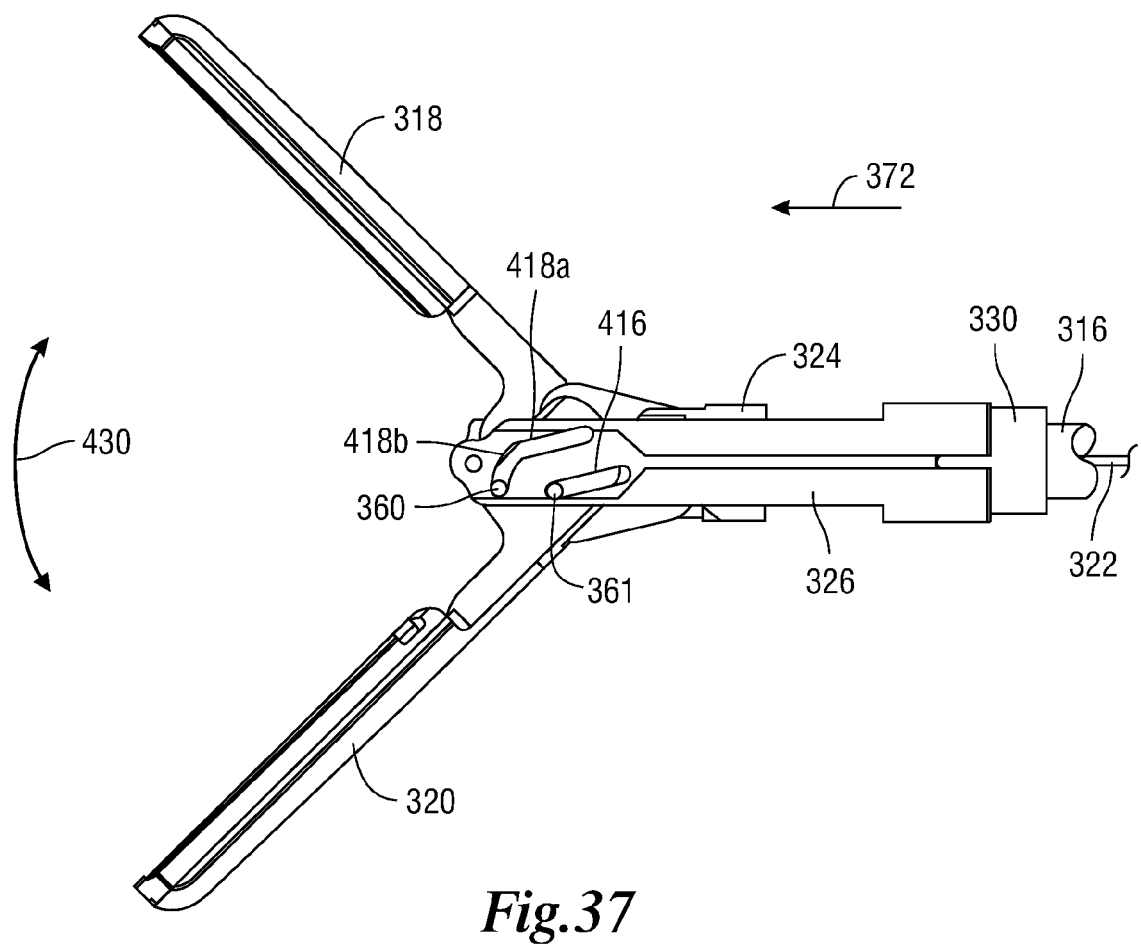

FIG. 37 is a side view of one embodiment of the surgical grasping device shown in FIGS. 26a-b.

Figure 37A:
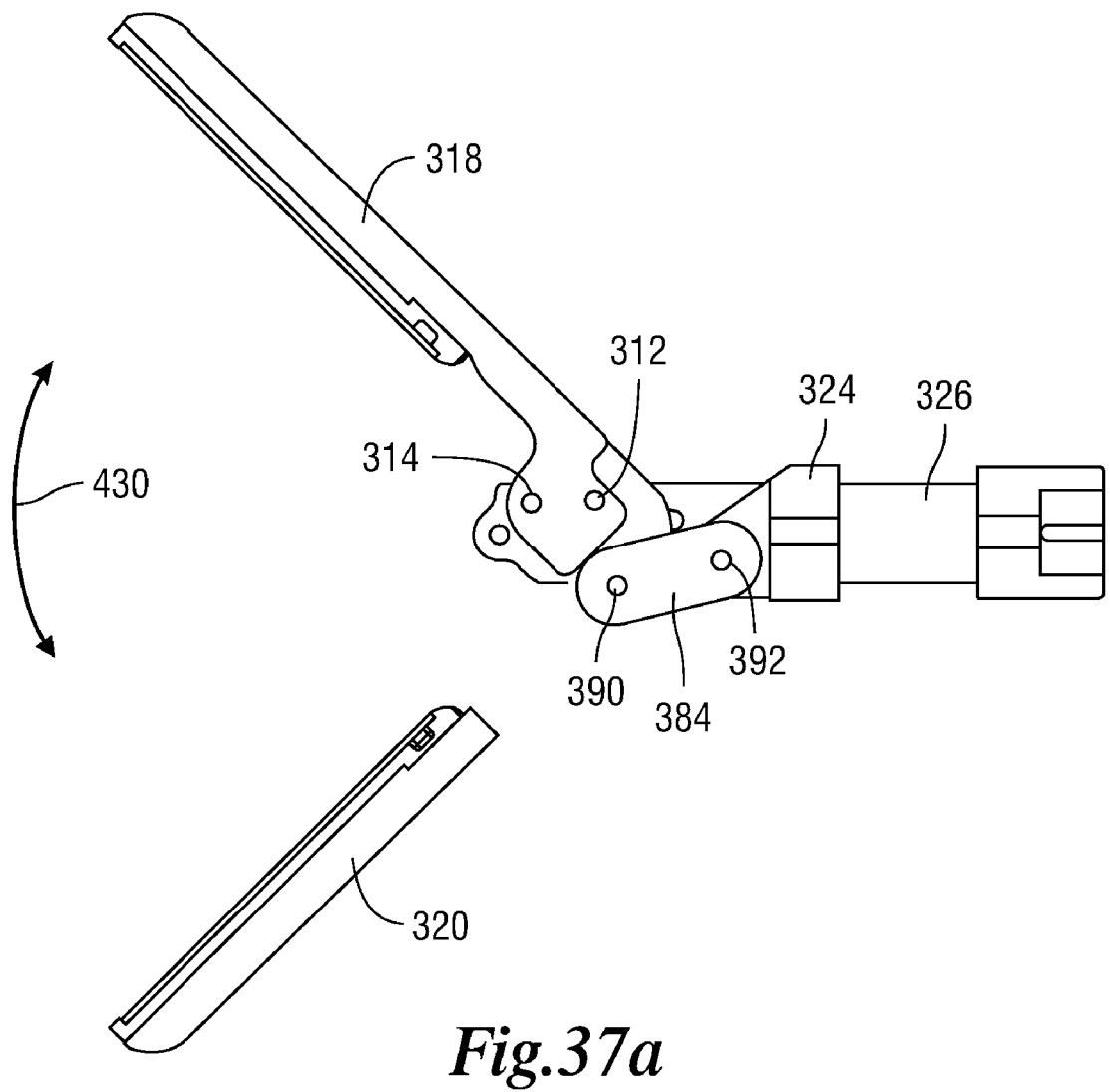

FIG. 37a is a cross-sectional view of one embodiment of the surgical grasping device shown in FIG. 37 taken along the longitudinal axis.

Figure 38:
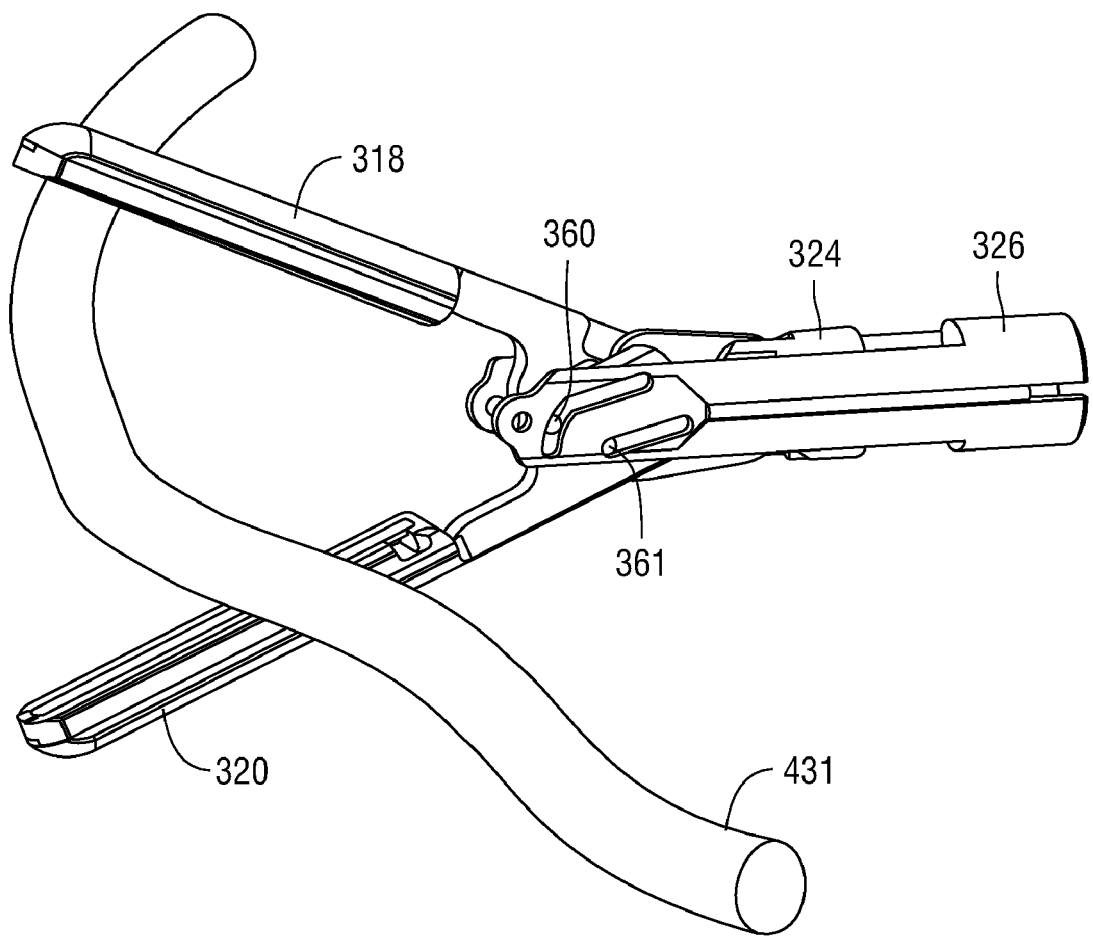

FIG. 38 illustrates an isometric view of the surgical device shown in FIGS. 26a-b ablating tissue.

Figure 39:
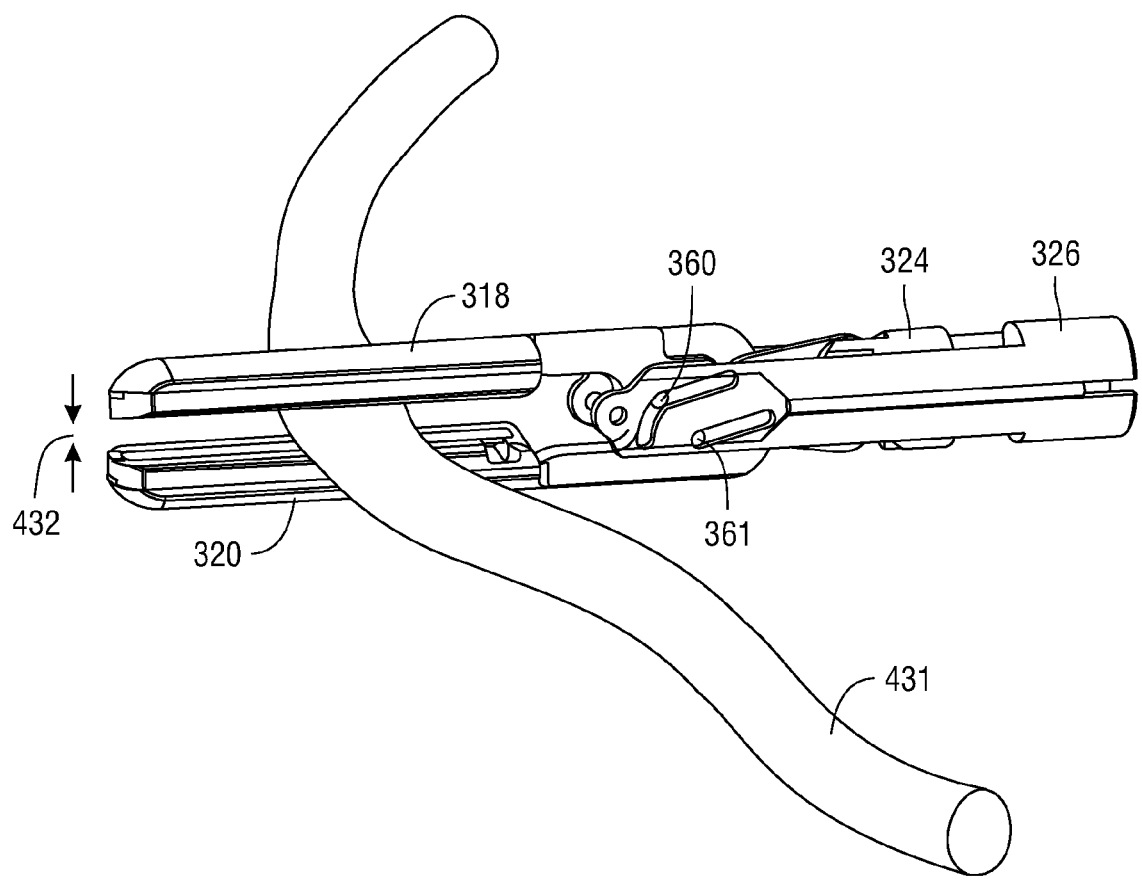

FIG. 39 illustrates an isometric view of the surgical device shown in FIGS. 26a-b ablating tissue.

Figure 40:
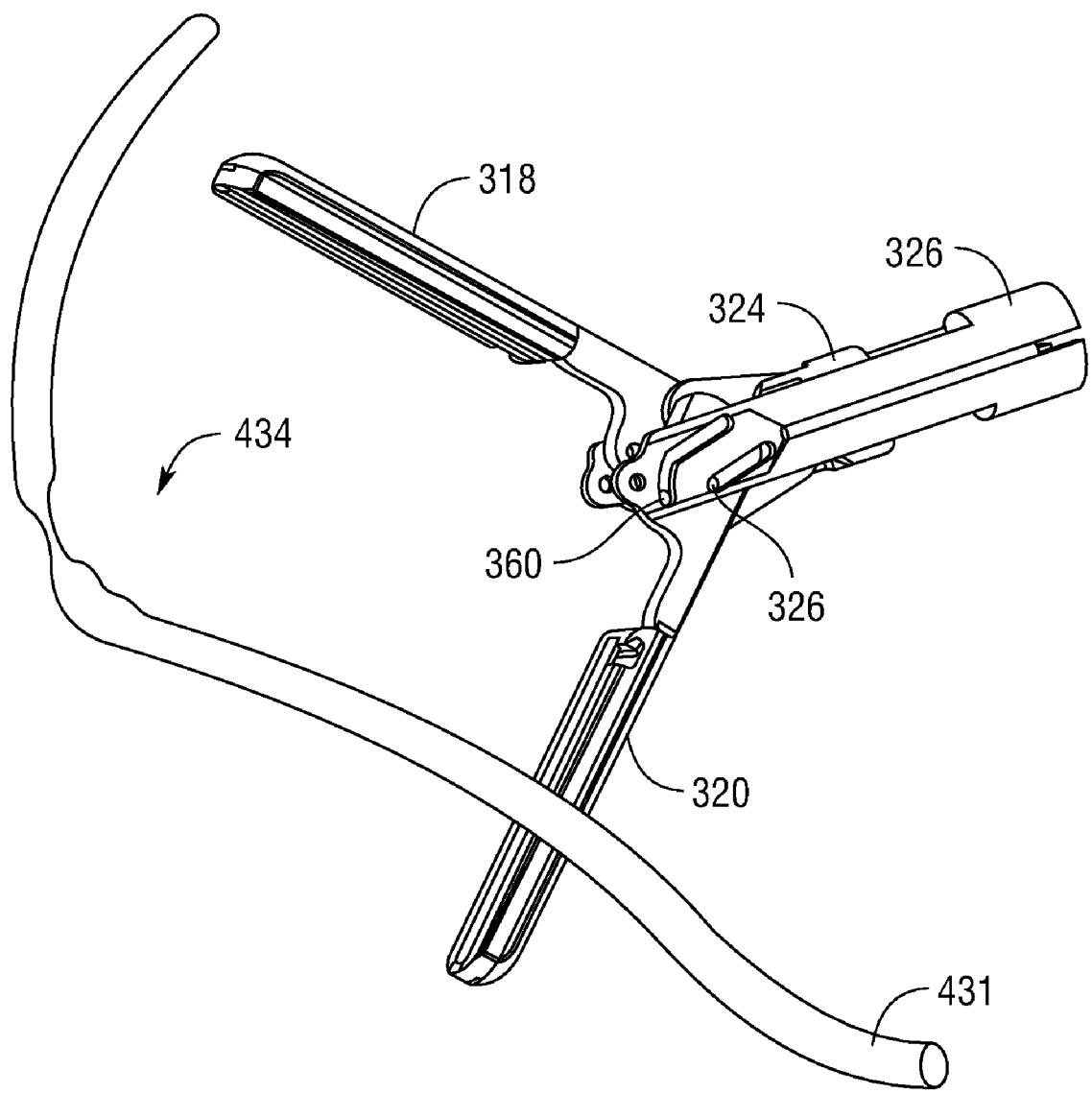

FIG. 40 illustrates an isometric view of the surgical device shown in FIGS. 26a-b ablating tissue.

DESCRIPTION

The various embodiments described herein are directed to actuating surgical devices, including cutting devices, grasping devices and electrical therapy ablation devices. The electrical therapy ablation devices comprise electrodes that can be positioned in or in proximity to a tissue treatment region (e.g., target site) within a patient endoscopically, transcutaneously (percutaneously), or laparoscopically and, in some embodiments, any combination thereof. In at least one form of the invention, a bipolar forceps can include two or more electrodes wherein the electrodes can be positioned against, or adjacent to, a vessel, such as a blood vessel, for example, and energy can be supplied to the electrodes. In various circumstances, the energy can be sufficient to at least substantially seal the vessel such that blood does not substantially flow therethrough. In at least one surgical technique, the bipolar forceps can be used to seal the vessel in two locations such that the vessel can be incised, or transected, at a location positioned intermediate the two seal locations. In at least one embodiment, the bipolar forceps can include a cutting element which can be configured to incise the vessel. In various embodiments, the cutting element can include a sharp edge which can be moved relative to the vessel. In at least one embodiment, the cutting element can be electrically connected to a source of energy wherein the energized cutting element can be configured to incise the tissue.

In at least one form of the invention, a bipolar forceps can include first and second electrodes positioned within first and second jaw members, respectively, wherein at least one of the jaw members can include a substantially tapered profile. In various surgical techniques, the jaw members can be positioned in a substantially closed position such that the distal end of the jaw members can be positioned intermediate a vessel, for example, and tissue at least partially surrounding the vessel. Thereafter, in at least one surgical technique, the jaw members can be opened in order to pull the vessel away from the soft tissue. In various techniques, the jaw members can be opened and closed repeatedly to enlarge a hole between the vessel and the tissue and/or otherwise separate the vessel from the tissue. In at least one embodiment, at least one of the jaw members can include ridges, teeth, and/or a textured outer surface configured to grip the soft tissue and/or vessel.

Once positioned, the electrical therapy electrodes are adapted to deliver energy, for example in the form of electrical current, to the treatment region. The electrical current may be generated by a control unit or generator located external to the patient. The electrical current may be characterized by a particular waveform in terms of frequency, amplitude, polarity, and pulse width. Depending on the diagnostic or therapeutic treatment rendered, the surgical device may comprise one electrode containing both a cathode and an anode or may contain a plurality of electrodes with at least one serving as a cathode and at least one serving as an anode. Depending on the diagnostic or therapeutic treatment rendered, the diseased tissue can be electrically ablated or destroyed. More particularly, the electrical therapy ablation devices may be employed to deliver sufficient energy to the diseased tissue to ablate or destroy tumors, masses, lesions, and other abnormal tissue growths. In at least one embodiment, the electrical therapy ablation devices and techniques described herein may be employed in the treatment of cancer by quickly creating necrosis and destroying live cancerous tissue in-vivo. Such devices and techniques are further described in a commonly-owned, U.S. patent application Ser. No. 11/897,676, entitled ELECTRICAL ABLATION SURGICAL INSTRUMENTS, filed on Aug. 31, 2007, published as United States Patent Application Publication No. 2009/0062788, the entire disclosure of which is hereby incorporated by reference herein.

Electrical therapy ablation may employ electroporation or electropermeabilization techniques where an externally applied electric field (electric potential) significantly increases the electrical conductivity and permeability of a cell plasma membrane. Electroporation is the generation of a destabilizing electric potential across such biological membranes. In electroporation, pores are formed when the voltage across the cell plasma membrane exceeds its dielectric strength. Electroporation destabilizing electric potentials are generally in the range of several hundred volts across a distance of several millimeters. Below certain magnitude thresholds, the electric potentials may be applied across a biological membrane as a way of introducing some substance into a cell, such as loading it with a molecular probe, a drug that can change the function of the cell, a piece of coding DNA, or increasing the uptake of drugs in cells. If the strength of the applied electrical field and/or the duration of exposure to it are suitably chosen, the pores formed by the electrical pulse reseal after a short period of time, during which period extracellular compounds may enter into the cell. Below a certain field threshold, the process is reversible and the potential does not permanently damage the cell membrane. This process may be referred to as reversible electroporation (RE).

On the other hand, excessive exposure of live cells to large electric fields can cause apoptosis and/or necrosis—the processes that result in cell death. Excessive exposure of live cells to large excessive electrical fields or potentials across the cell membranes causes the cells to die and therefore may be referred to as irreversible electroporation (IRE).

Electroporation may be performed with devices called electroporators. These appliances create the electric current and send it through the cell. Electroporators may comprise two or more metallic (e.g., aluminum) electrically conductive electrodes connected to an energy source. The energy source generates an electric field having a suitable characteristic waveform output in terms of frequency, amplitude, polarity, and pulse width.

Endoscopy refers to looking inside the human body for medical reasons. Endoscopy may be performed using an instrument called an endoscope. Endoscopy is a minimally invasive diagnostic medical procedure used to evaluate the interior surfaces of an organ by inserting a small tube into the body, often, but not necessarily, through a natural body opening or through a relatively small incision. Through the endoscope, an operator may observe surface conditions of the organs, including abnormal or diseased tissue such as lesions and other surface conditions. The endoscope may have a rigid or a flexible tube and in addition to providing an image for visual inspection and photography, the endoscope may be adapted and configured for taking biopsies, retrieving foreign objects, and introducing medical instruments to a tissue treatment region referred to as the target site. Endoscopy is a vehicle for minimally invasive surgery.

Laparoscopic surgery is a minimally invasive surgical technique in which operations in the abdomen are performed through small incisions (usually 0.5-1.5 cm), keyholes, as compared to larger incisions needed in traditional surgical procedures. Laparoscopic surgery includes operations within the abdominal or pelvic cavities, whereas keyhole surgery performed on the thoracic or chest cavity is called thoracoscopic surgery. Laparoscopic and thoracoscopic surgery belong to the broader field of endoscopy.

A key element in laparoscopic surgery is the use of a laparoscope: a telescopic rod lens system that is usually connected to a video camera (single-chip or three-chip). Also attached is a fiber-optic cable system connected to a "cold" light source (halogen or xenon) to illuminate the operative field, inserted through a 5 mm or 10 mm cannula to view the operative field. The abdomen is usually insufflated with carbon dioxide gas to create a working and viewing space. The abdomen is essentially blown up like a balloon (insufflated), elevating the abdominal wall above the internal organs like a dome. Carbon dioxide gas is used because it is common to the human body and can be removed by the respiratory system if it is absorbed through tissue.

The embodiments of the actuating cutting, dissecting, and electrical therapy ablation devices and techniques described herein may be employed to treat diseased tissue, tissue masses, tissue tumors, and lesions (diseased tissue) at a tissue treatment region (target site) within the body. Minimally invasive therapeutic procedures to treat diseased tissue by introducing medical instruments to a tissue treatment region through a natural opening of the patient are known as Natural Orifice Translumenal Endoscopic Surgery (NOTES)™.

Figure 1:
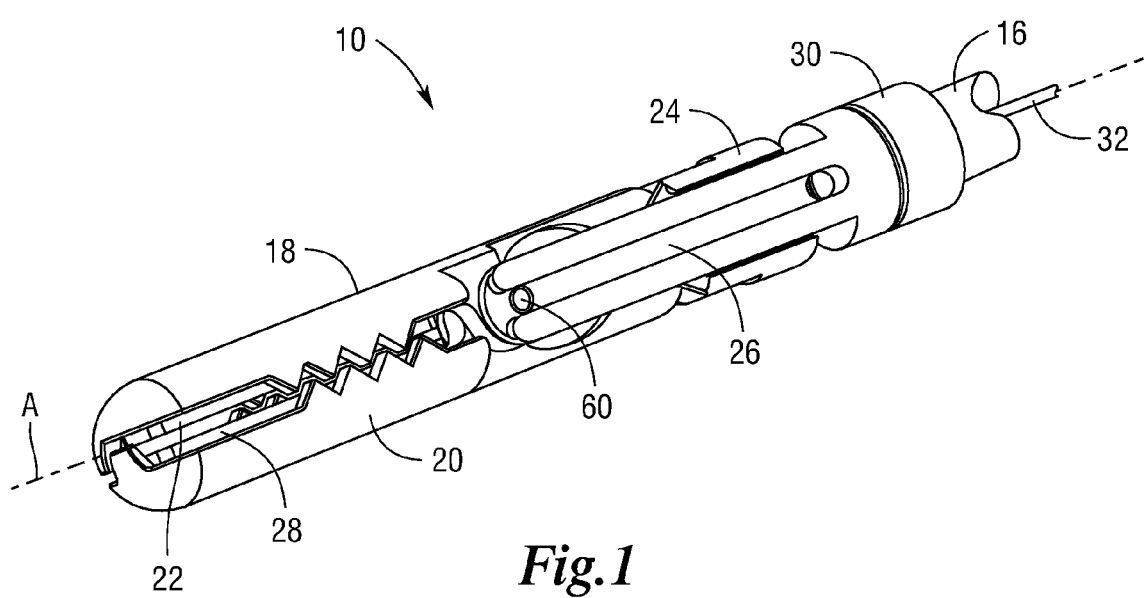
FIG. 1 is a perspective view of one embodiment of a surgical grasping device.

FIG. 1 illustrates one embodiment of a surgical device 10. Surgical device 10 may be employed to treat diseased tissue such as tumors and lesions inside a patient with electrical energy or otherwise dissect, cut, or manipulate tissue. Surgical device 10 may be used to treat the desired tissue treatment region in minimally invasive, open, or noninvasive surgical procedures. Minimally invasive surgical procedures include, for example, endoscopic, laparoscopic, thoracoscopic, or other surgical procedures that require small incisions or keyholes. Surgical device 10 also may be used in traditional open laparotomy procedures as well as external noninvasive procedures to treat diseased tissue outside the body. In one embodiment, surgical device 10 may be configured to be positioned within a natural opening of the patient such as the mouth, anus, vagina, or colon and subsequently advanced and positioned within internal body lumens such as the esophagus and/or uterus to reach the tissue treatment region or target site. Internal organs may be reached using trans-organ or transluminal surgical procedures. Surgical device 10 also may be configured to be positioned through a small incision or keyhole on the patient and can be passed through the incision to reach a tissue treatment region or target site through a trocar. The tissue treatment region may be located in various body lumens or organs such as the esophagus, stomach, colon, liver, breast, brain, lung, and other organs or locations within the body. Surgical device 10 can be configured to treat a number of lesions and ostepathologies comprising metastatic lesions, tumors, fractures, infected sites, inflamed sites, and the like. Once positioned in the tissue treatment region, surgical device 10 can be configured to treat and ablate the diseased tissue in that region. In one embodiment, surgical device 10 may be adapted to treat diseased tissue, such as cancers, of the gastrointestinal (GI) tract, esophagus, or lung that may be accessed orally. In another embodiment, surgical device 10 may be adapted to treat diseased tissue, such as cancers, of the liver or other organs that may be accessible trans-anally through the colon and/or the abdomen via well-known procedures.

In one embodiment, surgical device 10 may be employed in conjunction with a flexible endoscope, such as the GIF-100 model available from Olympus Corporation. The flexible endoscope may be introduced into the patient trans-anally through the colon, orally through the esophagus, vaginally through the uterus, or the abdomen via an incision or keyhole and a trocar, for example. The endoscope assists the surgeon to guide and position the surgical device 10 near the tissue treatment region to treat diseased tissue in various body lumens and organs such as the esophagus, stomach, colon, liver, breast, brain, lung, and other internal tissue treatment regions.

FIG. 1 shows a perspective view of one embodiment of a surgical device 10. Surgical device 10 generally comprises a top jaw 18, a bottom jaw 20, a clevis 26 and a slider 24. In various embodiments, top jaw 18 may house a top electrode 22 and bottom jaw 20 may house a bottom electrode 28. A coupling 30 allows for the attachment of clevis 26 to a shaft 16. In various embodiments coupling 30 may be optionally configured to allow the surgical device 10 to rotate relative to and about a longitudinal axis "A", thus allowing surgical device 10 to be positioned in multiple angular orientations. Some embodiments may have multiple couplings 30. Optionally, surgical device 10 may, for example, be attached to a laparoscopic and endoscopic instrument. Accordingly, in various embodiments, shaft 16 may be either flexible or rigid, or a combination thereof. A driveline 32 is located inside shaft 16. In various embodiments, driveline 32 passes through the center of coupling 30 and is attached to slider 24. Driveline 32 may be coupled to slider 24 using any suitable means, such as laser welding. Slider 24 functions to slide on longitudinal axis "A."

As shown in FIG. 1, surgical device 10 is configured for electrical therapy ablation, but in other embodiments may be configured for cutting, dissecting, or grasping. For example, top jaw 18 and bottom jaw 20 may be configured with cutting blades, a plurality of teeth, or any other configuration providing the required functionality.

Figure 2:
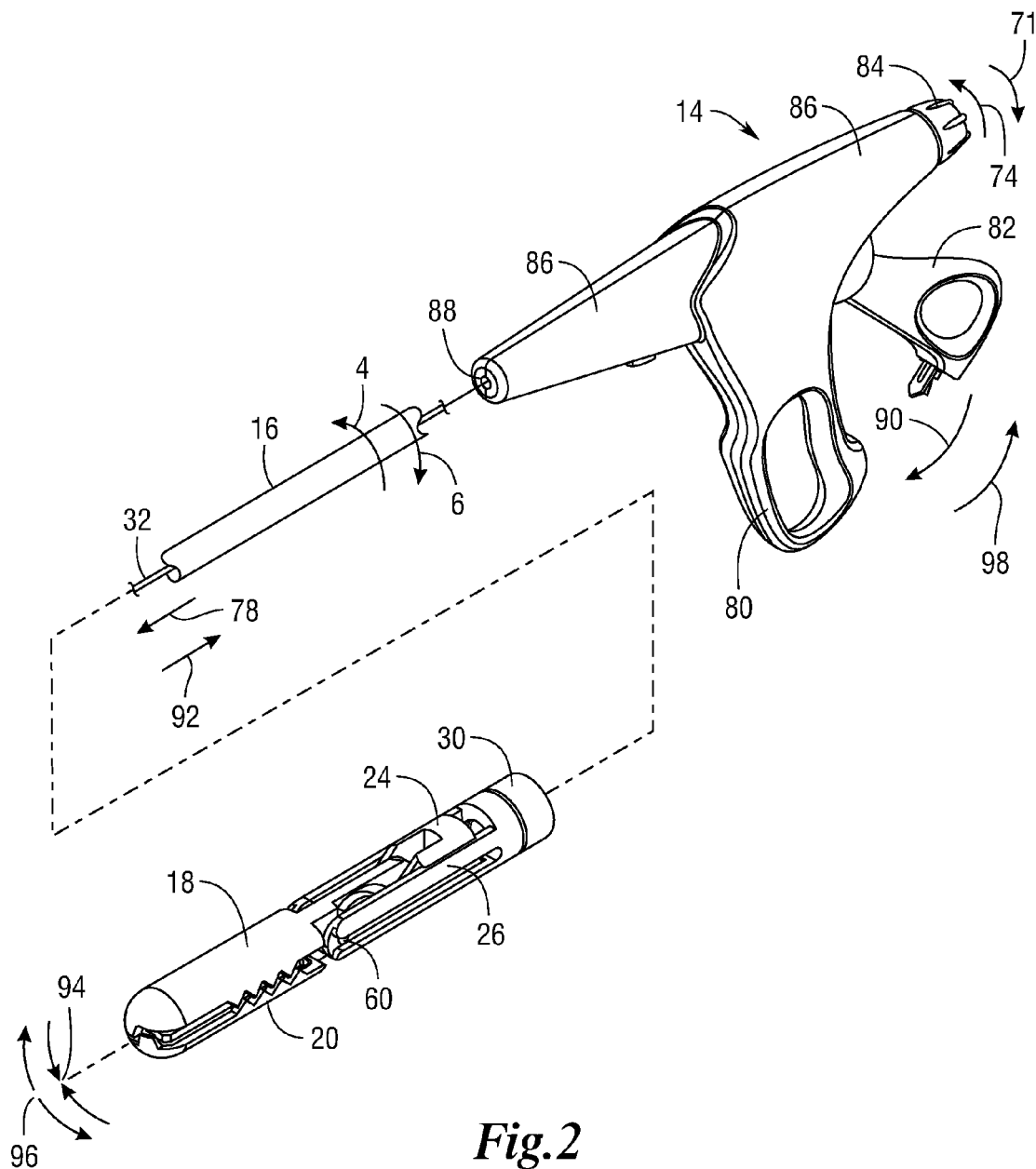
FIG. 2 is a perspective view of one embodiment of a system comprising the surgical grasping device shown in FIG. 1.

FIG. 2 is a perspective view of surgical device 10 and a handle assembly 14 coupled thereto. It is understood by those skilled in the art that surgical device 10 can be coupled to any control device, mechanical or electrical, which allows for actuation of top jaw 18 and bottom jaw 20. Handle assembly 14 comprises a base handle portion 86, a trigger 82, a rotation knob 84, and an opening 88 to receive the proximal end of driveline 32. Trigger 82 is operatively coupled to driveline 32. When trigger 82 is pivotally moved (e.g., squeezed) in a direction indicated by arrow 90, driveline 32 moves in a direction indicated by arrow 92, and top and bottom jaw members 18, 20 close in a direction indicated by arrow 94. When trigger 82 is pivotally moved (e.g., released) in a direction indicated by arrow 98, driveline 32 moves in a direction indicated by arrow 78, and top and bottom jaw members 18, 20 open in a direction indicated by arrow 96. The distal end of driveline 32 is received within rotation knob 84. When rotation knob 84 is rotated in a direction indicated by arrow 74, surgical device 10 also is rotated in a direction indicated by arrow 4. When rotation knob 84 is rotated in a direction indicated by arrow 76, surgical device 10 is also rotated in direction indicated by arrow 6. In various embodiments, an energy source, such as a waveform generator (not shown), may be connected to surgical device 10 in order to provide electrical energy to any electrodes incorporated into surgical device 10.

Figure 2A:
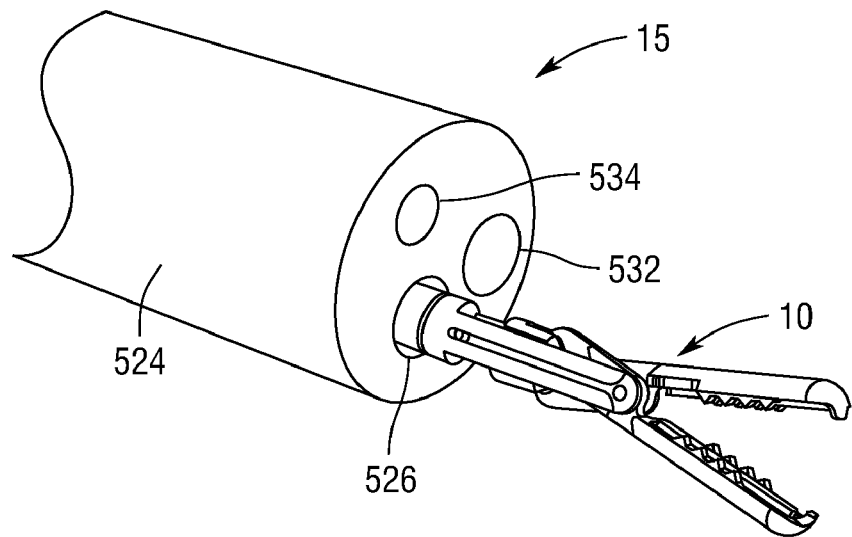
FIG. 2A illustrates an embodiment with a surgical grasping device protruding from the working channel of an endoscope.

FIG. 2A illustrates one embodiment surgical device 10 with an endoscope 15. In the illustrated embodiment, surgical device 10 is introduced into a working channel 526 at the proximal end of the endoscope 15. As surgical device 10 is inserted through working channel 526, surgical device 10 protrudes from a distal end of endoscopic portion 524. As shown in FIG. 2A, endoscopic portion 524 may comprise a light source 532, a viewing port 534, and working channel 526. Viewing port 532 may transmit an image within its field of view to an optical device such as a charge coupled device (CCD) camera within the endoscope 15 so that an operator may view the image on a display monitor (not shown).

Figure 3:
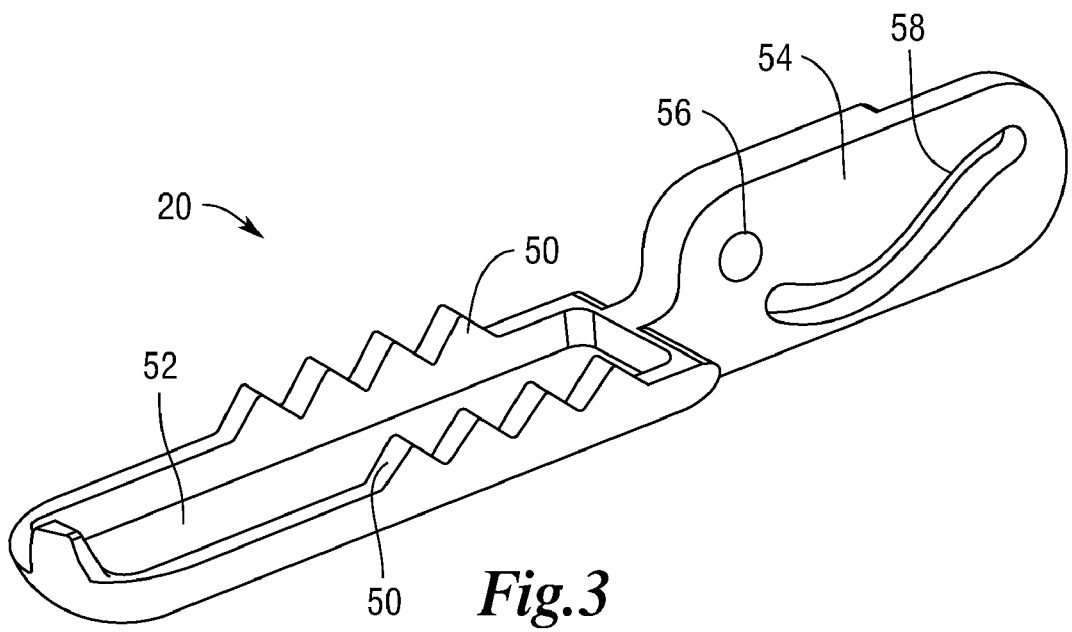
FIG. 3 illustrates one embodiment of a bottom jaw of the surgical grasping device shown in FIG. 1.

FIG. 3 shows a perspective view of bottom jaw 20 of one embodiment of surgical device 10. Jaw 20 may include a plurality of teeth 50. Jaw 20 also may define a cavity 52 to house bottom electrode 28. A rear fin 54 defines a hole 56 and a slot 58. Hole 56 is suitable to receive jaw pin 60 (FIG. 1). Slot 58 may extend through rear fin 54 to create an elongated opening or may only extend partially into rear fin 54 to create a groove or indention in rear fin 54. The shape of slot 58 may be of any desired curved, arcuate, or generally linear profile. In some embodiments, slot 58 may comprise any combination of curved, arcuate, or generally linear sections in order to achieve the desired functionality (i.e., open force, close force, clamp force).

Figure 4:
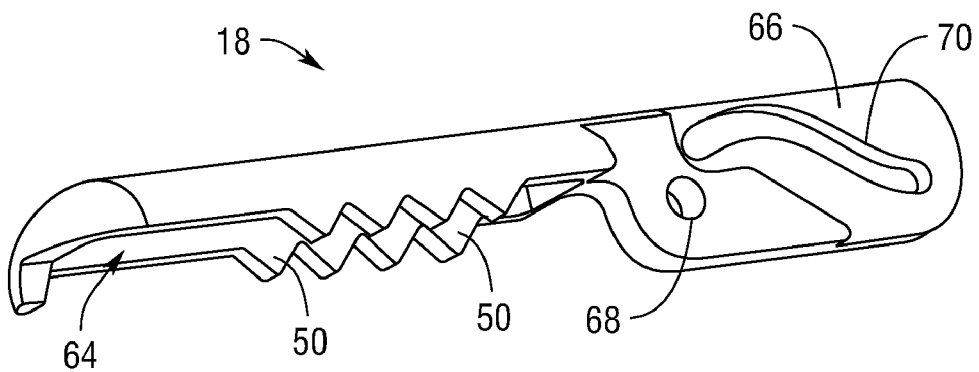
FIG. 4 illustrates one embodiment of a top jaw of the surgical grasping device shown in FIG. 1.

FIG. 4 shows a perspective view of top jaw 18 of one embodiment of the surgical device 10. Top jaw 18 is constructed similarly to bottom jaw 20. Jaw 18 may include a plurality of teeth 50. Jaw 18 also may define a cavity 64 to house top electrode 22. A rear fin 66 defines a hole 68 and may have a slot 70. Hole 68 is suitable to receive jaw pin 60 (FIG. 1). Slot 70 may extend through rear fin 66 to create an elongated opening or may only extend partially into rear fin 66 to create a groove or indention in rear fin 66. The shape of slot 70 may be of any desired profile, such as curved, arcuate, or generally linear. When surgical device 10 is assembled, jaw pin 60 is inserted through holes 56, 68 to serve as a pivot point for top jaw 18 and bottom jaw 20.

Figure 5:
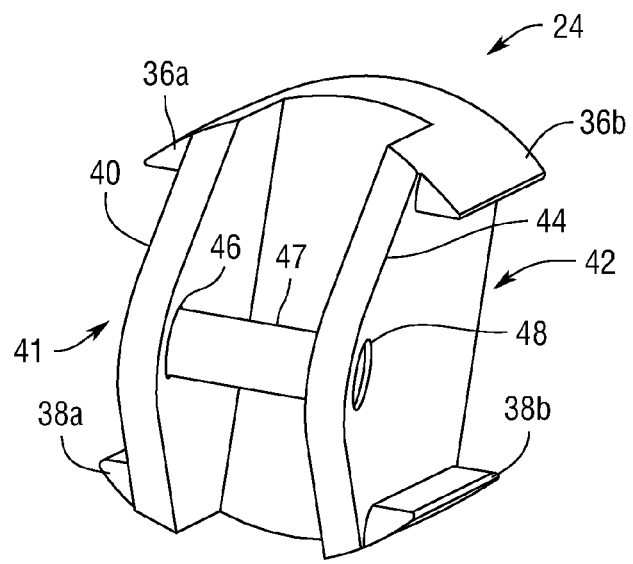
FIG. 5 illustrates one embodiment of a slider of the surgical grasping device shown in FIG. 1.

As shown in FIG. 5, slider 24 may have top flanges 36a, 36b and bottom flanges 38a, 38b extending from either side of slider 24. Top flange 36a and bottom flange 38a on first side 40 define a first channel 41, and top flange 36b and bottom flange 38b define a second channel 42 on second side 44. First side 40 and second side 42 also may define a first hole 46 and second hole 48, respectively. First hole 46 and second hole 48 are suitable to receive a slider pin 47. In various embodiments, slider 24 is positioned in surgical device 10 such that clevis 26 is received by first channel 41 and second channel 42. As described in more detail below, slider 24 functions to slide on longitudinal axis "A", as shown in FIG. 1, along clevis 26. Top flanges 36a, 36b and bottom flanges 38a, 38b keep slider 24 generally affixed to clevis 26 while allowing for axial movement. Since driveline 32 is coupled to slider 24, the actuation of trigger 82 also serves to move slider 24. Therefore, movement of trigger 82 is translated into longitudinal movement of slider 24 along clevis 26.

Figure 6:
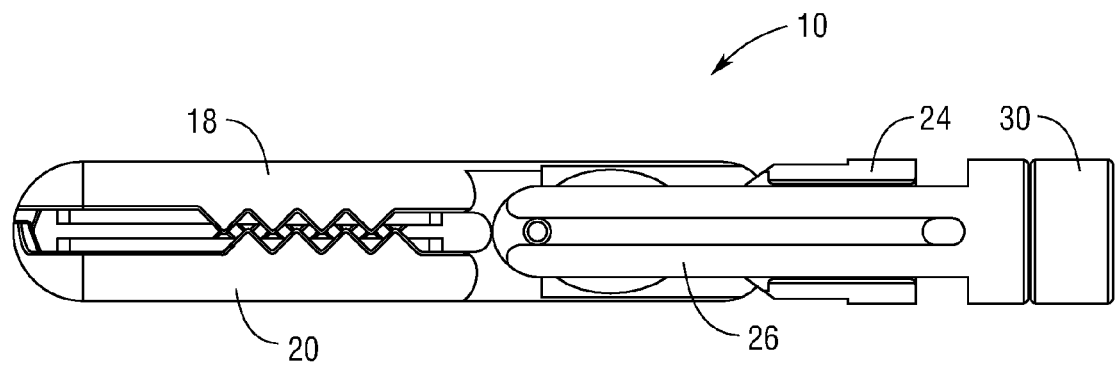
FIG. 6 is a side view of one embodiment of the surgical grasping device shown in FIG. 1.

FIG. 6 is a side view of one embodiment of surgical device 10. When assembled, jaw pin 60 is inserted through hole 68 of top jaw 18 and hole 56 of bottom jaw 20. Jaw pin 60 serves as a pivot point during actuation of top jaw 18 and bottom jaw 20. Rear fins 54, 66 are positioned beside each other such that slider pin 47 may extend through first side 40 of slider 24, through slot 70 of top jaw 18, through slot 58 of bottom jaw 20, and through second side 44 of slider 24.

Figure 6A:
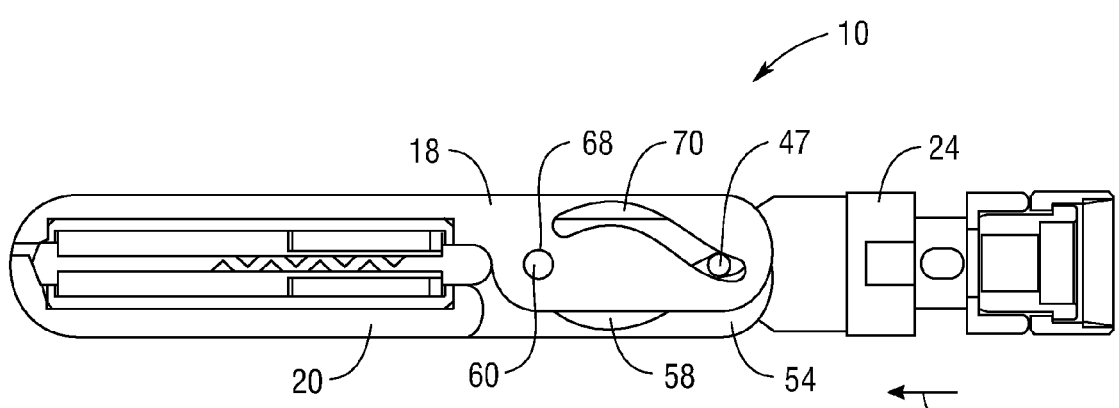
FIG. 6a is a cross-sectional view of one embodiment of the surgical grasping device shown in FIG. 6 taken along the longitudinal axis.

FIGS. 6, 6a, 7, 7a, 8, and 8a demonstrate a progression of the actuation of one embodiment of surgical device 10. Referring first to FIGS. 6 and 6a, a cross-sectional perspective view of one embodiment of surgical device 10 taken along longitudinal axis "A" of FIG. 6, surgical device 10 is shown in a "closed position." In its closed position top jaw 18 and bottom jaw 20 are in close proximity to each other, allowing for the cutting, grasping, or ablating of tissue. In order to actuate, or open, top jaw 18 and bottom jaw 20, the user imparts movement to driveline 32. In various embodiments, trigger 82 may be used to impart such movement. Slider 24 is coupled to driveline 32; therefore, movement of driveline 32 in a first direction 72 moves slider 24 longitudinally in first direction 72, or toward the distal end of surgical device 10.

Figure 7:
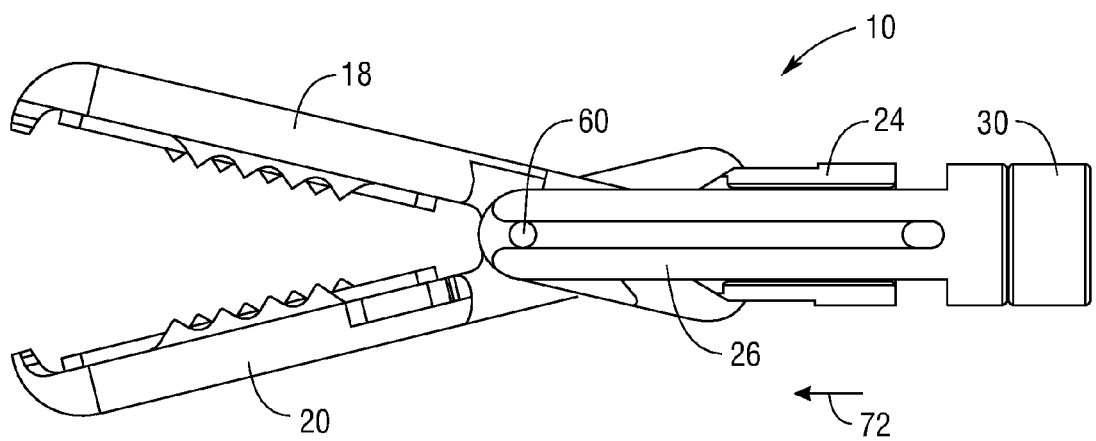
FIG. 7 is a side view of one embodiment of the surgical grasping device shown in FIG. 1 during actuation.
Figure 7A:
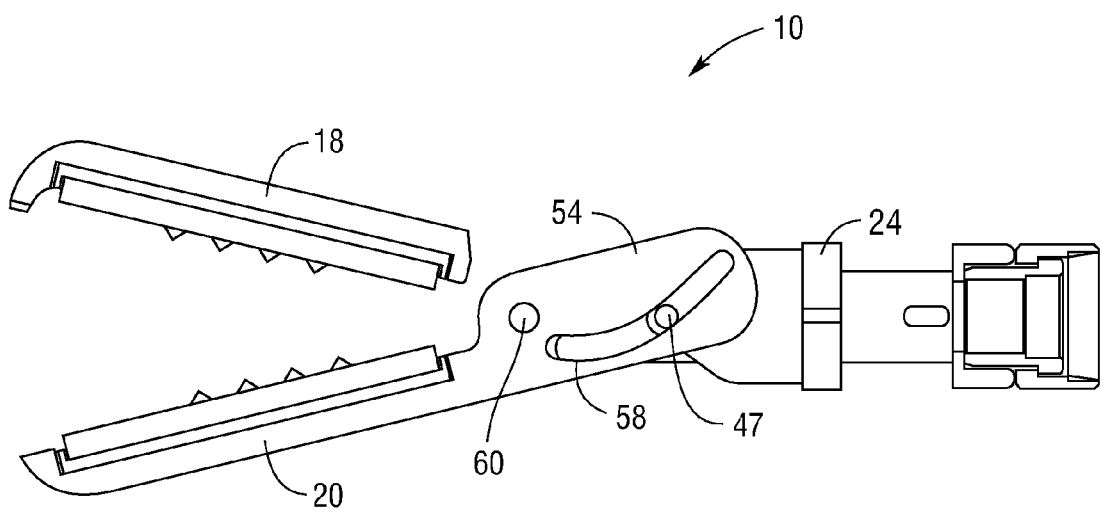
FIG. 7a is a cross-sectional view of one embodiment of the surgical grasping device shown in FIG. 7 taken along the longitudinal axis.

FIG. 7 shows the position of top jaw 18 and bottom jaw 20 after slider 24 has moved in first direction 72. By virtue of the movement of driveline 32, slider 24 has been moved longitudinally along clevis 26. FIG. 7a is a cross-sectional perspective view of one embodiment of surgical device 10 taken along the longitudinal axis of FIG. 7. Movement of slider 24 in first direction 72 moves slider pin 47 in first direction 72. This movement of slider pin 47 causes slider pin 47 to travel within slot 58 of bottom jaw 20 and slot 70 of top jaw 18. Due to the profile of slots 58, 70, top jaw 18 and bottom jaw 20 pivot about jaw pin 60 and separate from each other.

Figure 8:
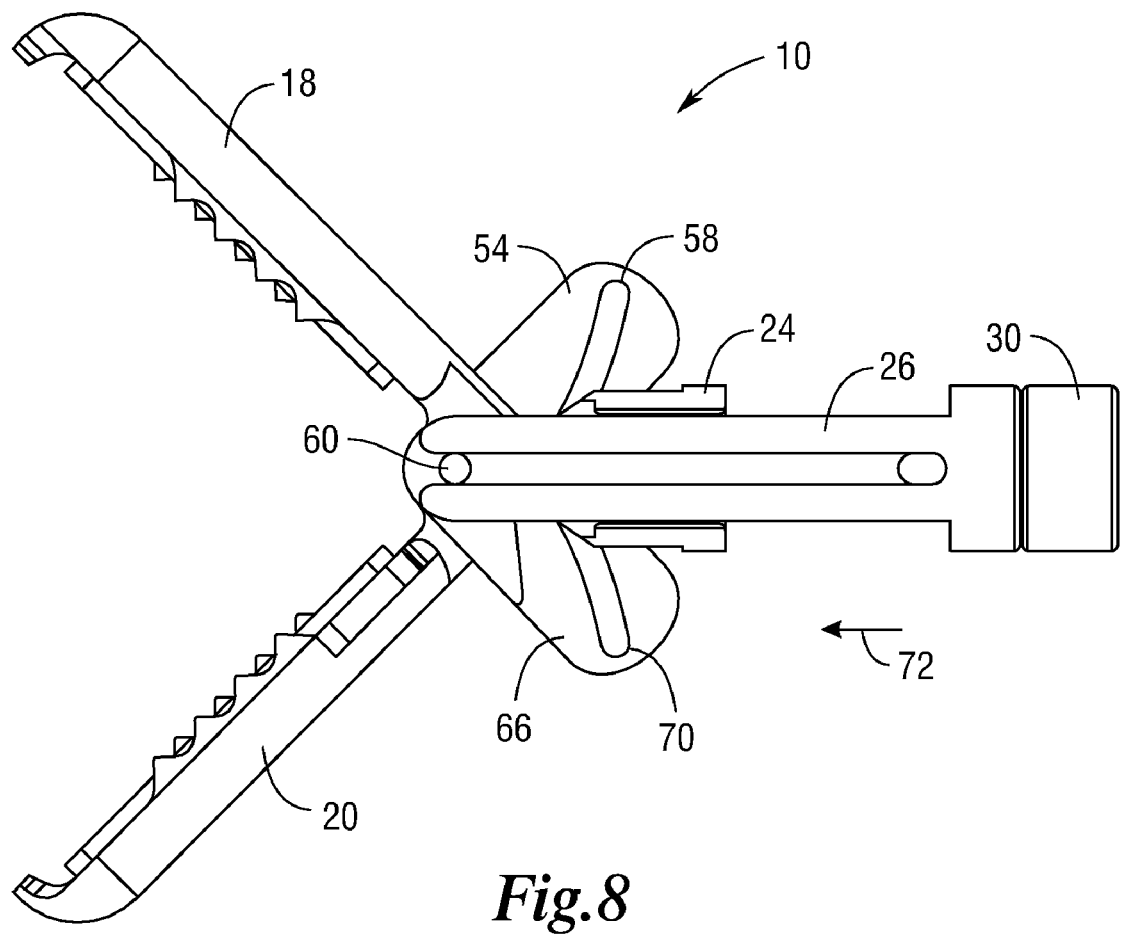
FIG. 8 is a side view of one embodiment of the surgical grasping device shown in FIG. 1 during actuation.
Figure 8A:
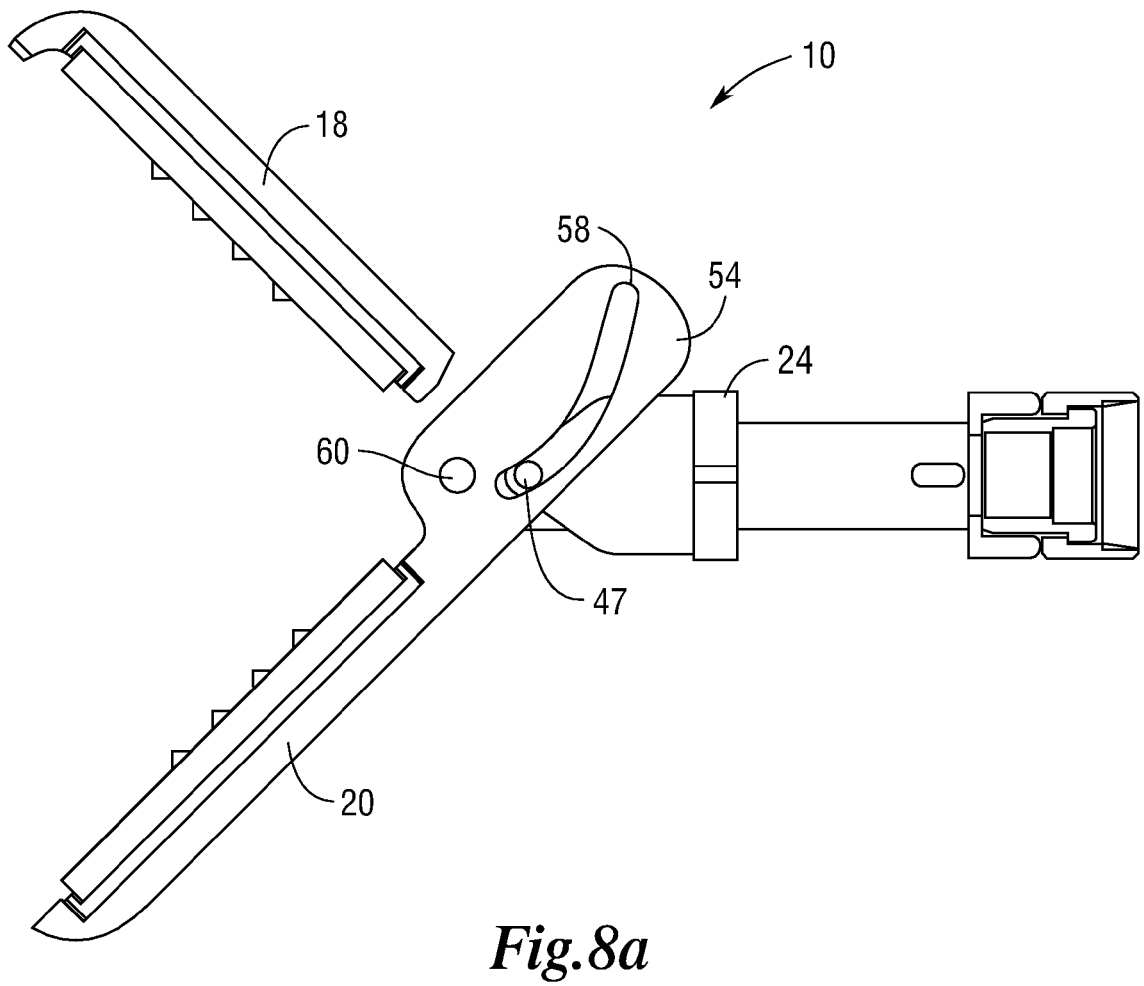
FIG. 8a is a cross-sectional view of one embodiment of the surgical grasping device shown in FIG. 8 taken along the longitudinal axis.

FIG. 8 shows the position of top jaw 18 and bottom jaw 20 after slider 24 has moved further in first direction 72. Slider 24 has been further moved longitudinally along clevis 26. FIG. 8a is a cross-sectional view of one embodiment of surgical device 10 taken along the longitudinal axis of FIG. 8. Due to the profile of slots 58, 70, top jaw 18 and bottom jaw 20 pivot about jaw pin 60 and separate further from each other. As shown, top jaw 18 and bottom jaw 20 are nearly at a completely opened position. Furthermore, pin 47 has traveled nearly the full length of slots 58, 70.

In various embodiments, other techniques may be utilized to move slider 34 longitudinally along clevis 26. For instance, rotational movement of driveline 32 may be utilized to translate slider 24 along 26. In one embodiment, the distal end of driveline 32 comprises a first threaded feature that engages a second threaded feature associated with slider 24. As the user rotates or twists driveline 32, the first threaded feature on the distal end of driveline 32 also rotates. As driveline 32 rotates, the threaded engagement of the first and second threaded features imparts longitudinal motion to the slider 24. In one embodiment, the user may lock, or selectively fix, top jaw 18 and bottom jaw 20 at any desired angle by impeding rotational movement of driveline 32.

Figure 9:
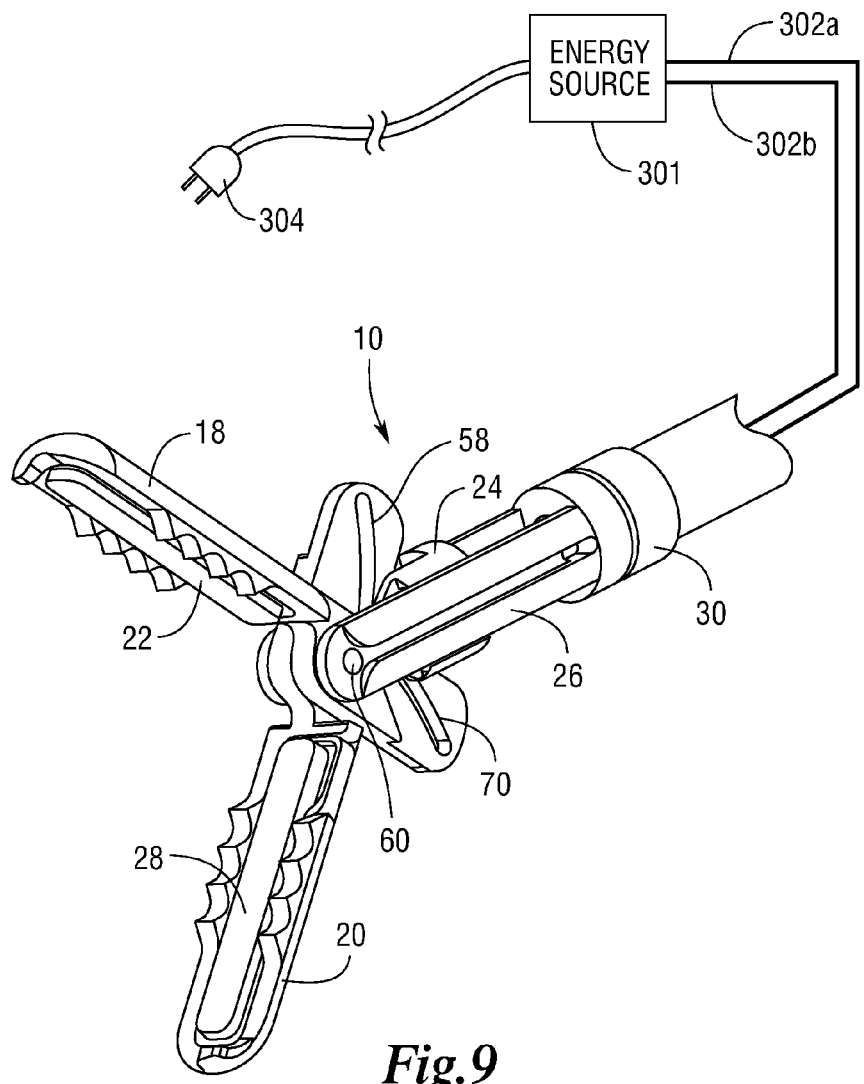
FIG. 9 is a perspective view of one embodiment of a surgical grasping device.

FIG. 9 shows an embodiment of the present invention which may be used for electrical ablation therapy. First and second electrical conductors 302a, 302b are electrically coupled to the respective top and bottom electrodes 22, 28 formed in the respective top and bottom jaw members 18, 20. In one embodiment, driveline 32 may serve as an electrical conductor. In various embodiments, top and bottom electrodes 22, 28 may be formed having a substantially flat, paddle-like shape. First and second electrical conductors 302a, 302b may be received through lumens formed in shaft 16 and are coupled to top and bottom electrodes 22, 28 in any suitable manner. A switch may be coupled to electrical conductors 302a, 302b to enable an operator to activate and deactivate top and bottom electrodes 22, 28 after tissue at the desired target site is grasped between respective top and bottom jaw members 18, 20.

An energy source 301, such as an electrical waveform generator, is employed to energize top and bottom electrodes 22, 28 with an electrical energy level suitable to produce an arc between top electrode 22 and bottom electrode 28. The electric arc is suitable to ablate fibrous tissues such as adhesions growing between internal organs of a patient, for example. The input to energy source 301 is connected to a commercial power supply by way of a plug 304. The output of energy source 301 is coupled to surgical device 10 through first and second electrical conductors 302a, 302b.

In one embodiment, energy source 301 comprises a timing circuit to interrupt the output of energy source 301 and produce a cyclical pattern. The timing circuit may comprise suitable switching elements to produce a cyclical or pulsed output energy signal to drive top and bottom electrodes 22, 28 of surgical device 10. For example, energy source 301 may produce a series of n pulses suitable to generate the electric arc, when the pulsed energy is applied to top and bottom electrodes 22, 28.

In one embodiment, energy source 301 comprises an electrical waveform generator to produce an electrical waveform. The electrical waveform generator produces electric potentials at predetermined frequencies, amplitudes, polarities, and pulse widths.

In one embodiment, energy source 301 comprises a radio frequency (RF) generator to produce RF waveforms at predetermined frequencies, amplitudes, polarities, and pulse widths. The RF generator may be a conventional, bipolar/monopolar electrosurgical generator such as one of the many models commercially available, including Model Number ICC 350, available from Erbe, GmbH.

In one embodiment, energy source 301 may be a conventional, bipolar/monopolar pulsed DC generator such as one of the many models commercially available, including Model Number ECM 830, available from BTX Molecular Delivery Systems, Boston, Mass. In bipolar mode, top electrode 22 may be electrically coupled to one polarity and bottom electrode 28 may be electrically coupled to the opposite polarity.

In various embodiments, energy source 301 produces direct current (DC) electrical pulses delivered at frequencies in the range of 1-20 Hz, amplitudes in the range of ±100 to ≅1000 VDC, and pulse widths in the range of 0.01-100 ms. For example, an electrical waveform having an amplitude of +500 VDC and a pulse duration of 20 ms may be delivered at a pulse repetition rate or frequency of 10 HZ to ablate tissue. In one embodiment, the polarity of top and bottom electrodes 22, 28 may be electronically reversed. For example, the polarity of electrical pulses initially delivered at amplitudes in the range of +100 to +1000 VDC may be reversed to −100 to −1000 VDC.

Figure 10:
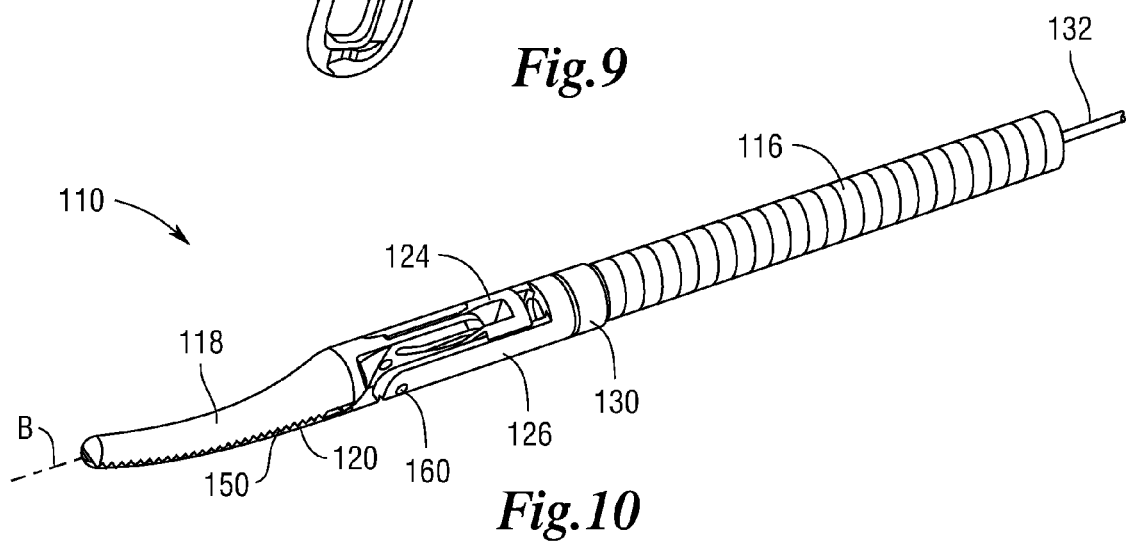
FIG. 10 is a perspective view of one embodiment of a surgical grasping device.

FIG. 10 shows an embodiment of surgical device 110. In various embodiments, surgical device 110 may have a top jaw 118 and a bottom jaw 120 pivotally coupled to a clevis 126. Surgical device 110 may further comprise a slider 124 and a coupling 130. Coupling 130 allows for the attachment of clevis 126 to a shaft 116. In various embodiments coupling 130 may be optionally configured to allow the surgical device 110 to rotate relative to and about a longitudinal axis "B", thus allowing surgical device 110 to be positioned in multiple angular orientations. Some embodiments may have multiple couplings 130. Optionally, surgical device 110 may, for example, be attached to a laparoscopic and endoscopic instrument. In various embodiments, shaft 116 may be rigid or flexible. A driveline 132 is located inside shaft 116. Driveline 132 passes through the center of coupling 130 and is attached to slider 124. Driveline 132 may be coupled to slider 124 using any suitable means, such as laser welding. Slider 124 functions to slide on longitudinal axis "B."

As shown in FIG. 10 top jaw 118 and bottom jaw 120 comprise a plurality of teeth 150, but in various embodiments other jaw configurations may be used, such as scissors, or the jaw may be configured with an electrode, or plurality of electrodes, for ablation.

Figure 11:
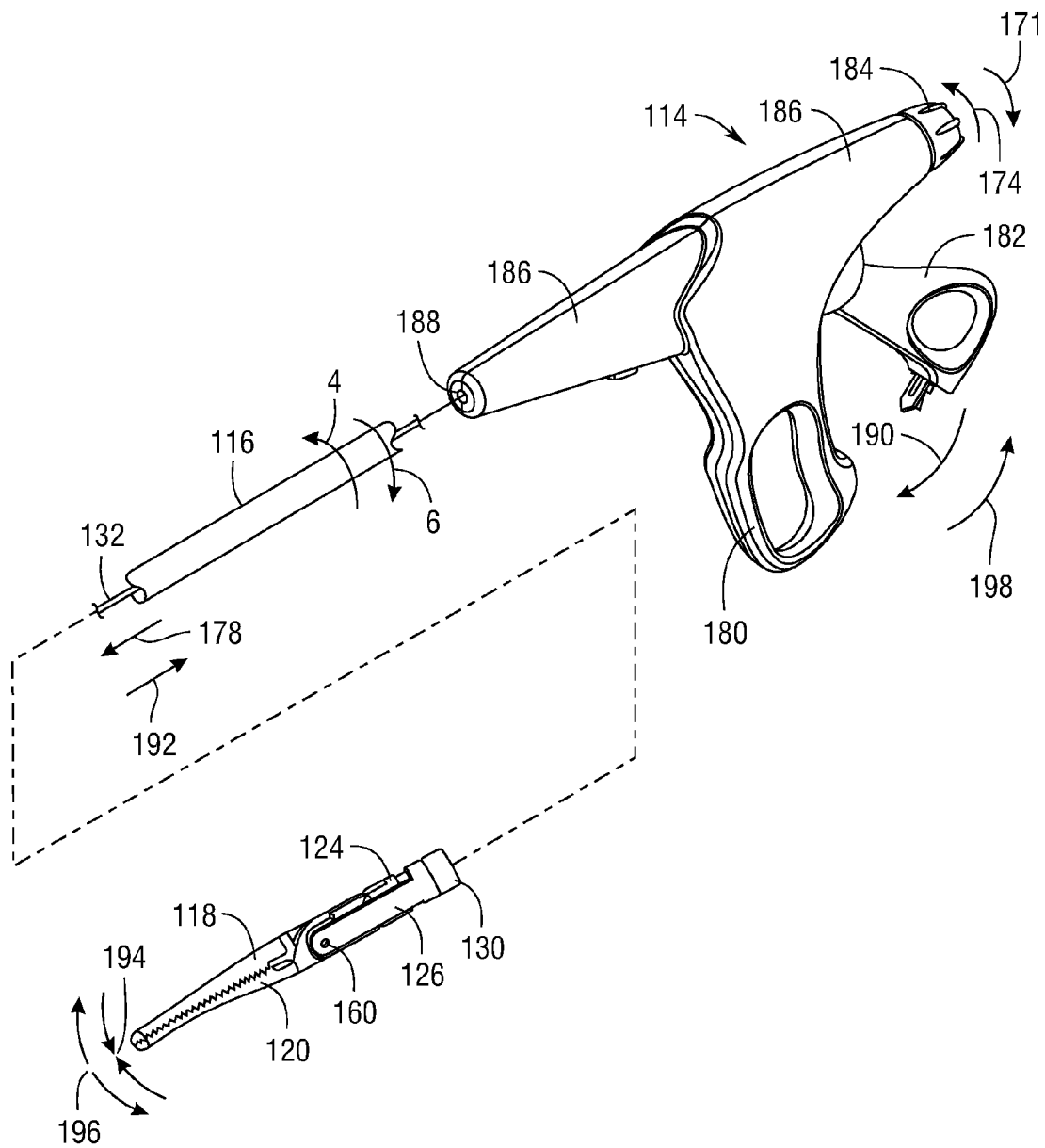
FIG. 11 is a perspective view of a system comprising the surgical grasping device shown in FIG. 10.

FIG. 11 is a perspective view of surgical device 110 and a handle assembly 114 coupled thereto. It is understood by those skilled in the art that surgical device 110 can be coupled to any control device, mechanical or electrical, which allows for actuation of top jaw 118 and bottom jaw 120. The handle assembly 114 comprises a base handle portion 186, a trigger 182, a rotation knob 184, and an opening 188 to receive the proximal end of driveline 132. Trigger 182 is operatively coupled to driveline 132. When trigger 182 is pivotally moved (e.g., squeezed) in a direction indicated by arrow 190, driveline 132 moves in a direction indicated by arrow 192, and top and bottom jaw members 118, 120 close in a direction indicated by arrow 194. When trigger 182 is pivotally moved (e.g., released) in a direction indicated by arrow 198, driveline 132 moves in a direction indicated by arrow 178, and top and bottom jaws 118, 120 open in a direction indicated by arrow 196. The distal end of driveline 132 is received within rotation knob 184. When rotation knob 184 is rotated in a direction indicated by arrow 174, surgical device 110 is also rotated in a direction indicated by arrow 104. When rotation knob 184 is rotated in a direction indicated by arrow 176, surgical device 110 is also rotated in a direction indicated by arrow 106. In various embodiments, a waveform generator (not shown) may be connected to surgical device 110 in order to provide electrical energy to any electrodes incorporated into surgical device 110.

Figure 12:
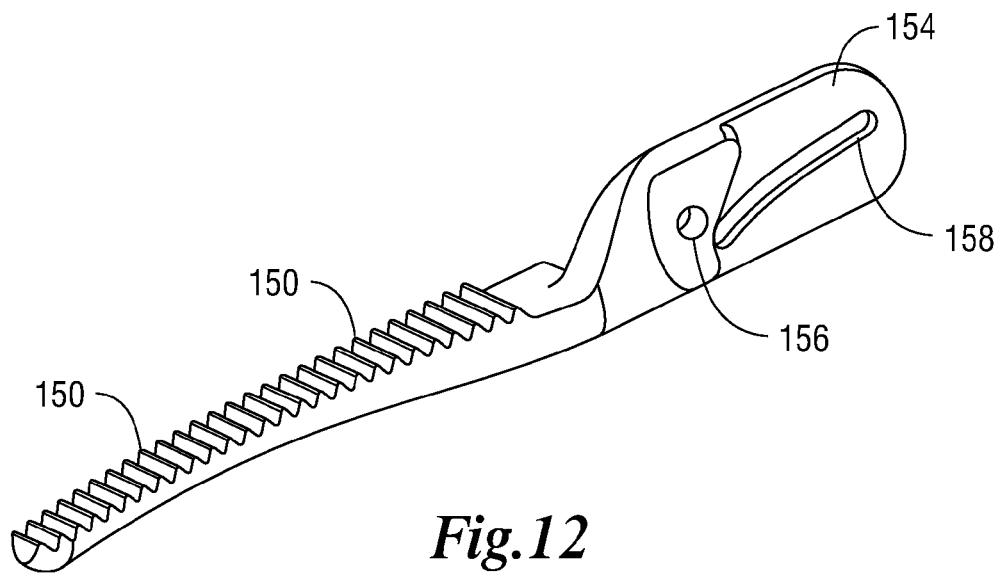
FIG. 12 illustrates one embodiment of a bottom jaw of the surgical grasping device shown in FIG. 10.

FIG. 12 shows a perspective view of one embodiment of a bottom jaw 120 of a surgical device 110. Bottom jaw 120 may include a plurality of teeth 150. A rear fin 154 defines a hole 156 and a slot 158. Hole 156 is suitable to receive jaw pin 160 (FIG. 9). Slot 158 may extend through rear fin 154 to create an elongated opening or may only extend partially into fin 154 to create a groove or indention in rear fin 154. The shape of slot 158 may be of any desired curved, arcuate, or generally linear profile. In some embodiments, slot 158 may comprise any combination of curved, arcuate, or generally linear sections in order to achieve the desired functionality.

Figure 13:
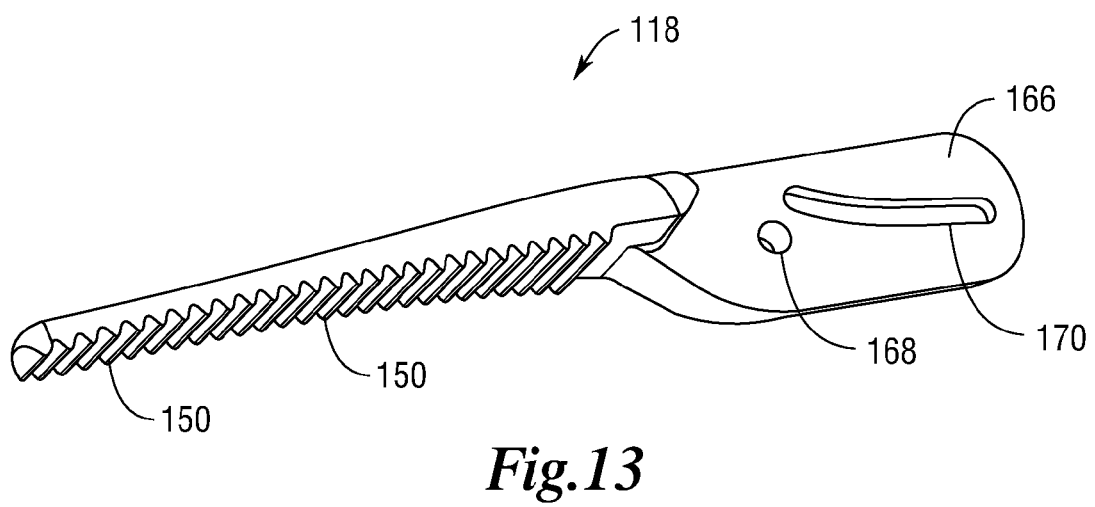
FIG. 13 illustrates one embodiment of a top jaw of the surgical grasping device shown in FIG. 10.

FIG. 13 shows a perspective view of one embodiment of a top jaw 118. Top jaw 118 is constructed similarly to bottom jaw 120. Jaw 118 may include a plurality of teeth 150. A rear fin 166 defines a hole 168 and may have a slot 170. Hole 168 is suitable to receive jaw pin 160 (FIG. 10). Slot 170 may extend through rear fin 166 to create an elongated opening or may only extend partially into fin 166 to create a groove or indention in rear fin 166. The shape of slot 170 may be of any desired curved, arcuate, or generally linear profile. In some embodiments, slot 170 may comprise any combination of curved, arcuate, or generally linear sections in order to achieve the desired functionality. When surgical device 110 is assembled, jaw pin 160 is inserted through holes 156, 168 to serve as a pivot point for top jaw 118 and bottom jaw 120.

Figure 14:
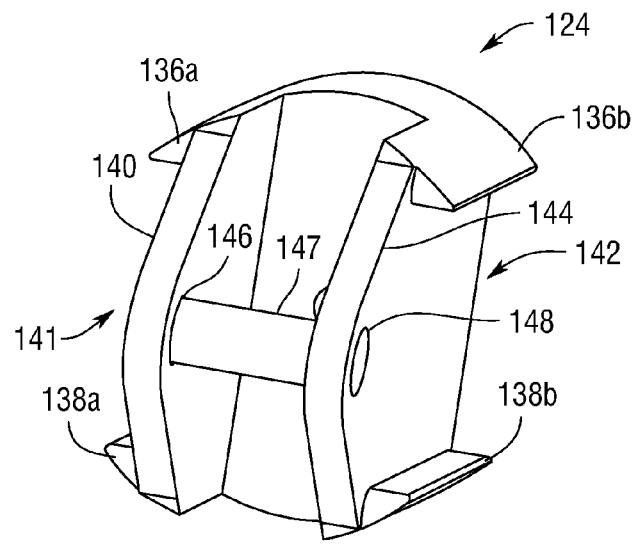
FIG. 14 illustrates one embodiment of a slider of the surgical grasping device shown in FIG. 10.

As shown in FIG. 14, slider 124 may have top flanges 136*a*, 136*b* and bottom flanges 138*a*, 138*b* extending from either side of slider 124. Top flange 136*a* and bottom flange 138*a* on first side 140 define a first channel 141, and top flange 136*b* and bottom flange 138*b* define a second channel 142 on second side 144. First side 140 and second side 142 may also define a first hole 146 and second hole 148, respectively. First hole 146 and second hole 148 are suitable to receive a slider pin 147. In various embodiments, slider 124 is positioned in surgical device 110 such that clevis 126 is received by first channel 141 and second channel 142. As described in more detail below, slider 124 functions to slide on a longitudinal axis "B", shown in FIG. 10, along clevis 126. Top flanges 136*a*, 136*b* and bottom flanges 138*a*, 138*b* keep slider 124 generally affixed to clevis 126. Since driveline 132 is coupled to slider 124, the actuation of trigger 182 also serves to move slider 124. Therefore, movement of trigger 182 is translated into longitudinal movement of slider 124 along clevis 126.

Figure 15:
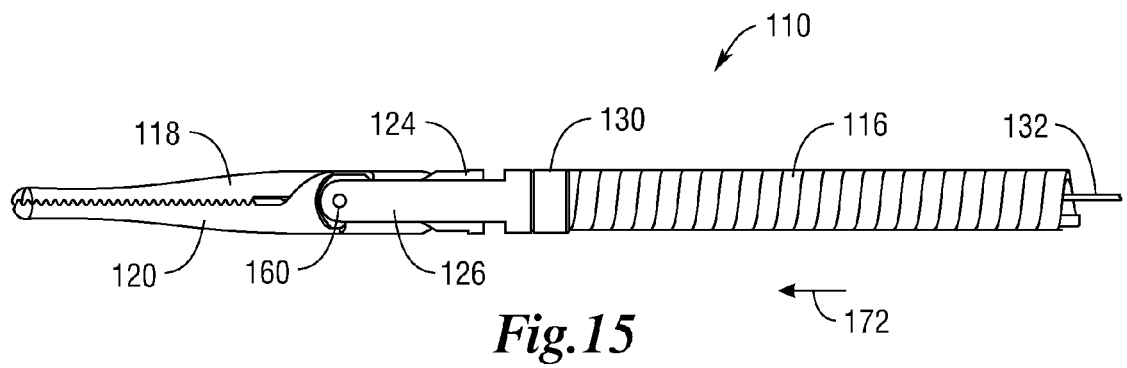
FIG. 15 is a side view of one embodiment of the surgical grasping device shown in FIG. 10.

FIG. 15 is a side view of one embodiment of surgical device 110. When assembled, jaw pin 160 is inserted through hole 168 of top jaw 118 and hole 156 of bottom jaw 120. Jaw pin 160 serves as a pivot point during actuation of top jaw 118 and bottom jaw 120. Rear fin 154 and rear fin 166 are positioned beside each other such that slider pin 147 may extend through first side 140 of slider 124, through slot 170 of top jaw 118, through slot 158 of bottom jaw 120, and through second side 144 of slider 124.

Figure 15A:
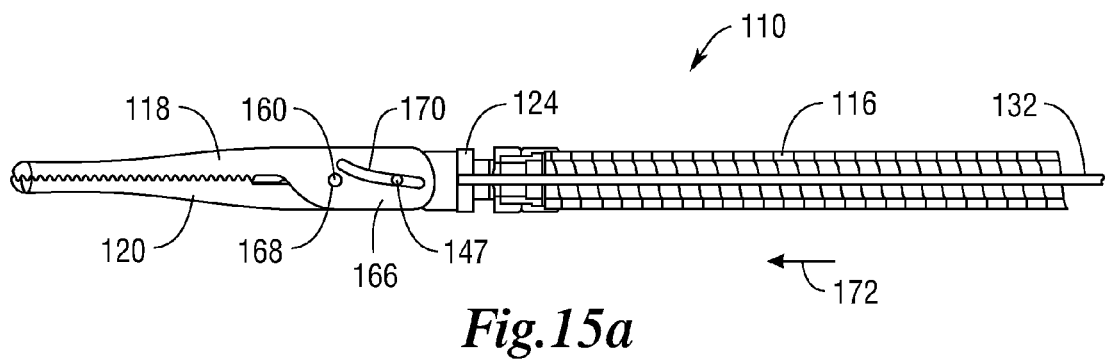
FIG. 15a is a cross-sectional view of one embodiment of the surgical grasping device shown in FIG. 15 taken along the longitudinal axis.

FIGS. 15, 15*a*, 16, 16*a*, 17, and 17*a* demonstrate a progression of the actuation of one embodiment of surgical device 110. Referring first to FIGS. 15 and 15*a*, a cross-sectional view of one embodiment of surgical device 110 taken along the longitudinal axis of FIG. 15, surgical device 110 is shown in a "closed position." In its closed position top jaw 118 and bottom jaw 120 are in close proximity to each other, allowing for the cutting, grasping, or ablating of tissue. In order to actuate, or open, top jaw 118 and bottom jaw 120, the user imparts movement to driveline 132. In various embodiments, trigger 182 may be used to impart such movement. Slider 124 is coupled to driveline 132; therefore, movement of driveline 132 in a first direction 172 moves slider 124 longitudinally in first direction 172, or toward the distal end of surgical device 110.

Figure 16:
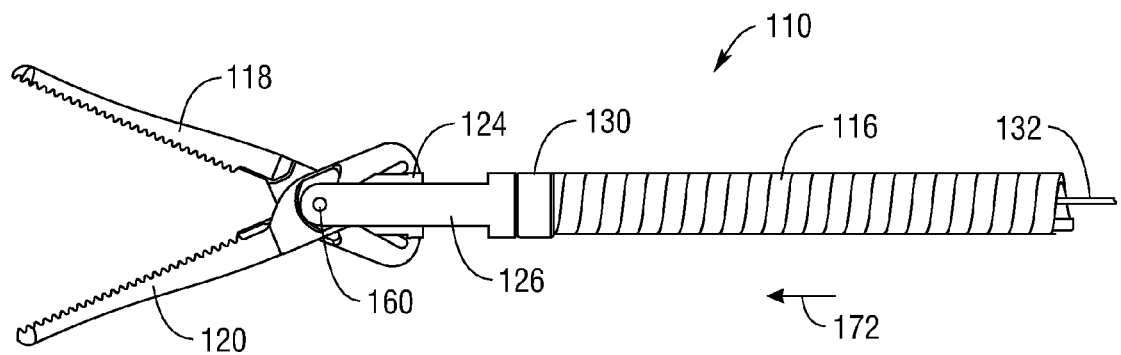
FIG. 16 is a side view of one embodiment of the surgical grasping device shown in FIG. 9 during actuation.
Figure 16A:
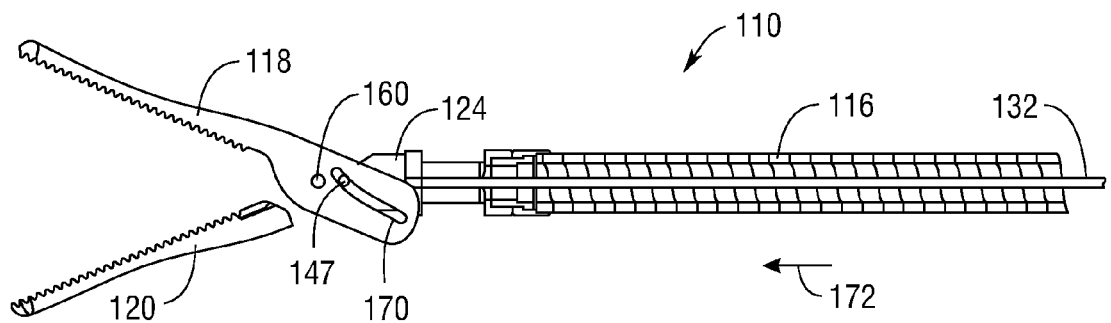
FIG. 16a is a cross-sectional view of one embodiment of the surgical grasping device shown in FIG. 16 taken along the longitudinal axis.

FIG. 16 shows the position of top jaw 118 and bottom jaw 120 after slider 124 has moved in first direction 172. By virtue of the movement of driveline 132, slider 124 has been moved longitudinally along clevis 126. FIG. 16*a* is a cross-sectional perspective view of one embodiment of surgical device 110 taken along the longitudinal axis of FIG. 16. Movement of slider 124 in first direction 172 moves slider pin 147 in first direction 172. This movement of slider pin 147 causes slider pin 147 to travel within slot 158 of bottom jaw 120 and slot 170 of top jaw 118. Due to the profile of slots 158, 170, top jaw 118 and bottom jaw 120 pivot about jaw pin 160 and separate from each other. The profile of slot 170 and slot 148 allow for greater opening force during operation. Those skilled in the art will appreciate that different slot profiles will allow for different opening and closing force characteristics, or force profiles, for various embodiments.

Figure 17:
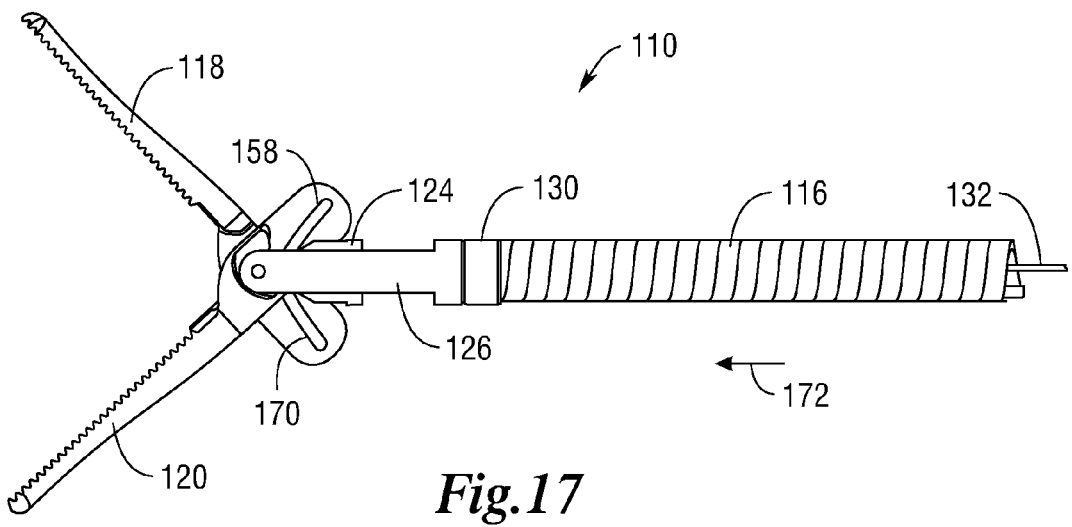
FIG. 17 is a side view of one embodiment of the surgical grasping device shown in FIG. 9 during actuation.
Figure 17A:
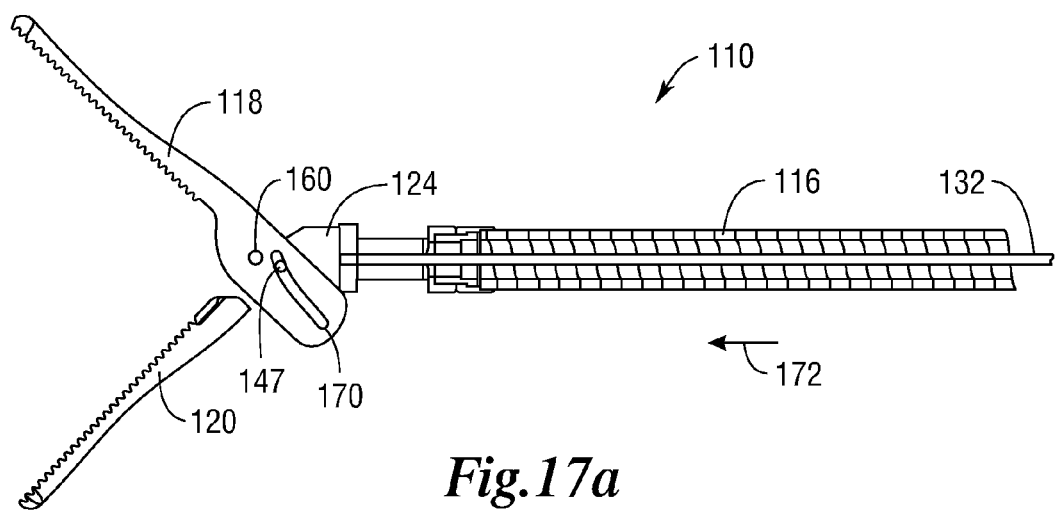
FIG. 17a is a cross-sectional view of one embodiment of the surgical grasping device shown in FIG. 17 taken along the longitudinal axis.

FIG. 17 shows the position of top jaw 118 and bottom jaw 120 after slider 124 has moved further in first direction 172. Slider 124 has been moved longitudinally further along clevis 126. FIG. 17*a* is a cross-sectional perspective view of one embodiment of surgical device 110 taken along the longitudinal axis of FIG. 17. Due to the profile of slots 158, 170, top jaw 118 and bottom jaw 120 pivot about jaw pin 160 and separate further from each other. As shown, top jaw 118 and bottom jaw 120 are nearly at a completely opened position. Furthermore, pin 147 has traveled nearly the full length of slots 158, 170.

Figure 18:
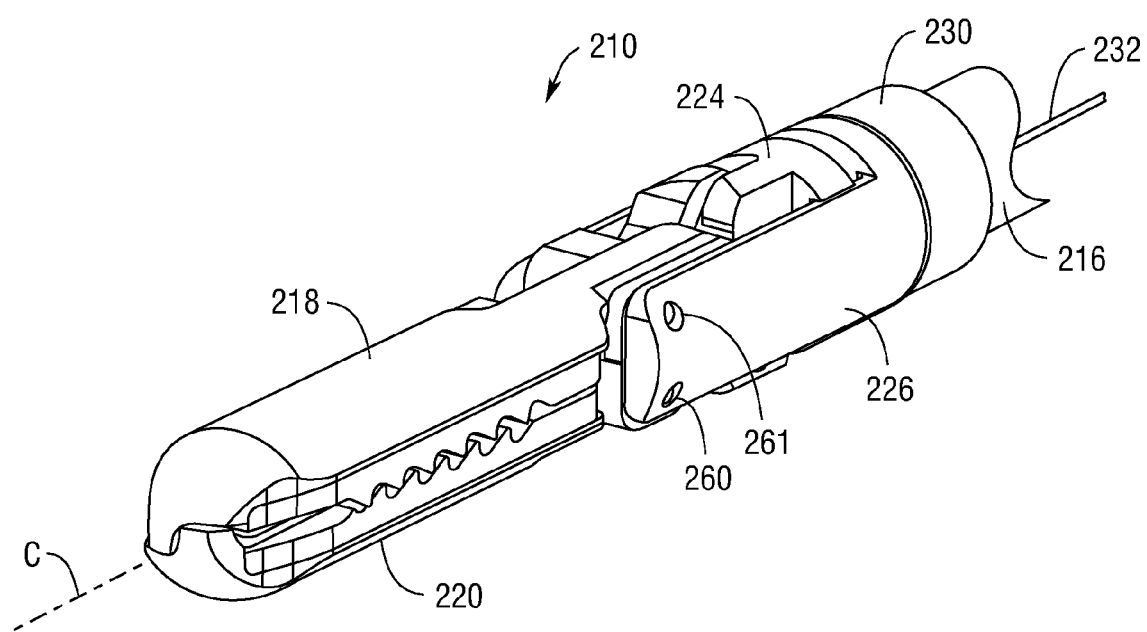
FIG. 18 is a perspective view of one embodiment of a surgical grasping device.

FIG. 18 shows one embodiment of surgical device 210. In various embodiments, surgical device 210 may have a top jaw 218 and a bottom jaw 220 pivotally coupled to a clevis 226. Surgical device 210 may further comprise a slider 224 and a coupling 230. Coupling 230 allows for the attachment of clevis 226 to shaft 216. In various embodiments coupling 130 may be optionally configured to allow the surgical device 110 to rotate relative to and about a longitudinal axis "C", thus allowing surgical device 110 to be positioned in multiple angular orientations. Some embodiments may have multiple couplings 130. Optionally, surgical device 210 may, for example, be attached to a laparoscopic and endoscopic instrument. In various embodiments, shaft 216 made be flexible or rigid, or a combination thereof. A driveline 232 is located inside shaft 216. In various embodiments, driveline 232 passes through the center of coupling 230 and is attached to slider 224. Driveline 232 may be coupled to slider 224 using any suitable means, such as laser welding. Slider 224 functions to slide on longitudinal axis "C."

As the user squeezes trigger 282 (FIG. 19), driveline 232 is moved longitudinally inside shaft 216.

As shown in FIG. 18, top jaw 218 and bottom jaw 220 may comprise a plurality of teeth 250, but in various embodiments other jaw configurations may be used, such as scissors, or the jaw may be configured with an electrode, or plurality of electrodes, for ablation.

Figure 19:
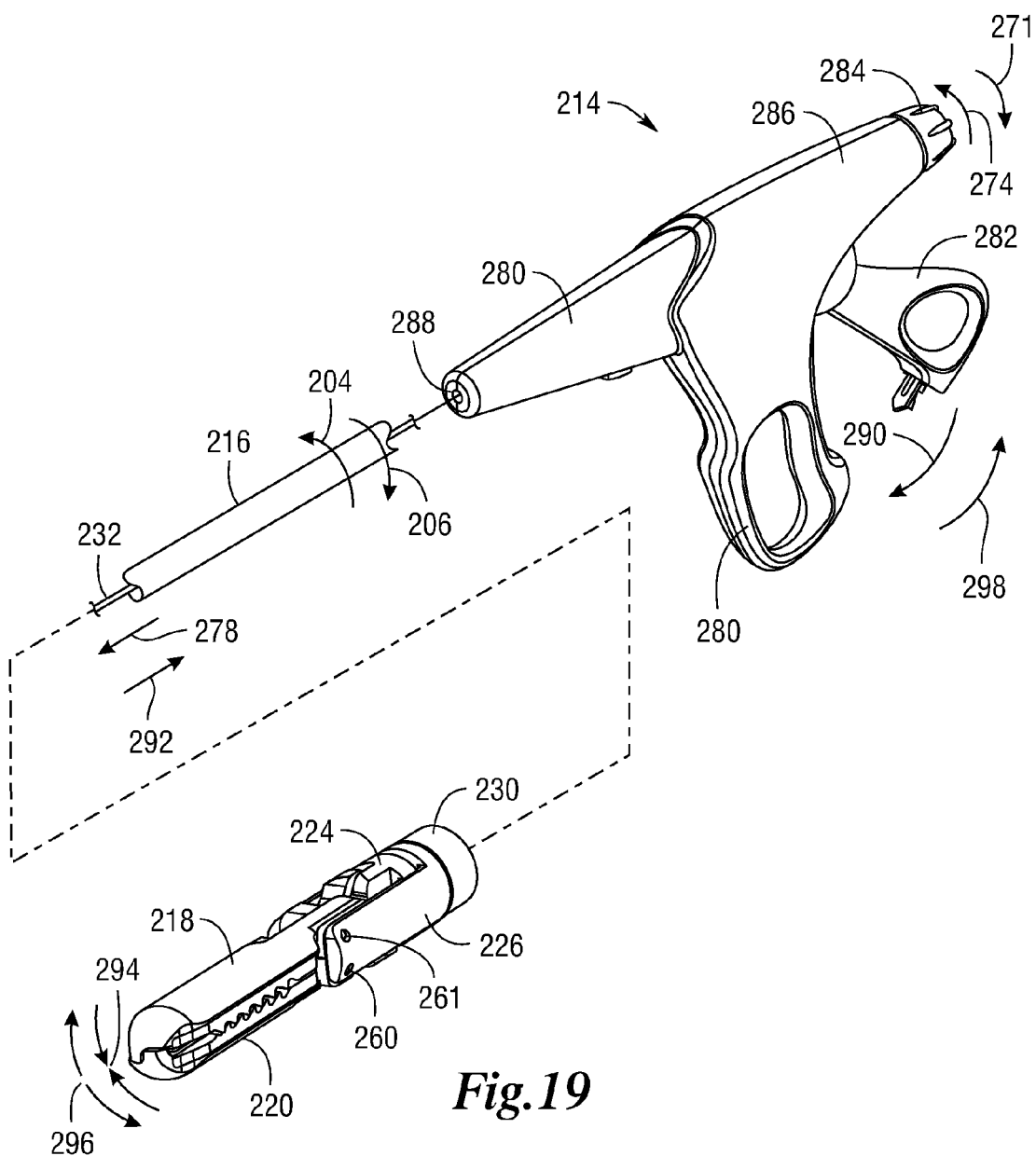
FIG. 19 is a perspective view of one embodiment of a system comprising the surgical grasping device shown in FIG. 18.

FIG. 19 is a perspective view of surgical device 210 and a handle assembly 214 coupled thereto. It is understood by those skilled in the art that surgical device 210 can be coupled to any control device, mechanical or electrical, which allows for actuation of top jaw 218 and bottom jaw 220. The handle assembly 214 comprises a base handle portion 286, a trigger 282, a rotation knob 284, and an opening 288 to receive the proximal end of driveline 232. Trigger 282 is operatively coupled to driveline 232. When trigger 282 is pivotally moved (e.g., squeezed) in a direction indicated by arrow 290, driveline 232 moves in a direction indicated by arrow 292, and top and bottom jaw members 218, 220 close in a direction indicated by arrow 294. When trigger 282 is pivotally moved (e.g., released) in a direction indicated by arrow 298, driveline 232 moves in a direction indicated by arrow 278, and top and bottom jaw members 218, 220 open in a direction indicated by arrow 296. The distal end of driveline 232 is received within rotation knob 284. When rotation knob 284 is rotated in a direction indicated by arrow 274, surgical device 210 also is rotated in a direction indicated by arrow 204. When rotation knob 284 is rotated in a direction indicated by arrow 276, surgical device 210 is also rotated in a direction indicated by arrow 206. In various embodiments, a waveform generator (similar to energy source 301 shown in FIG. 9) may be connected to surgical device 210 in order to provide electrical energy to any electrodes incorporated into surgical device 210.

Figure 20:
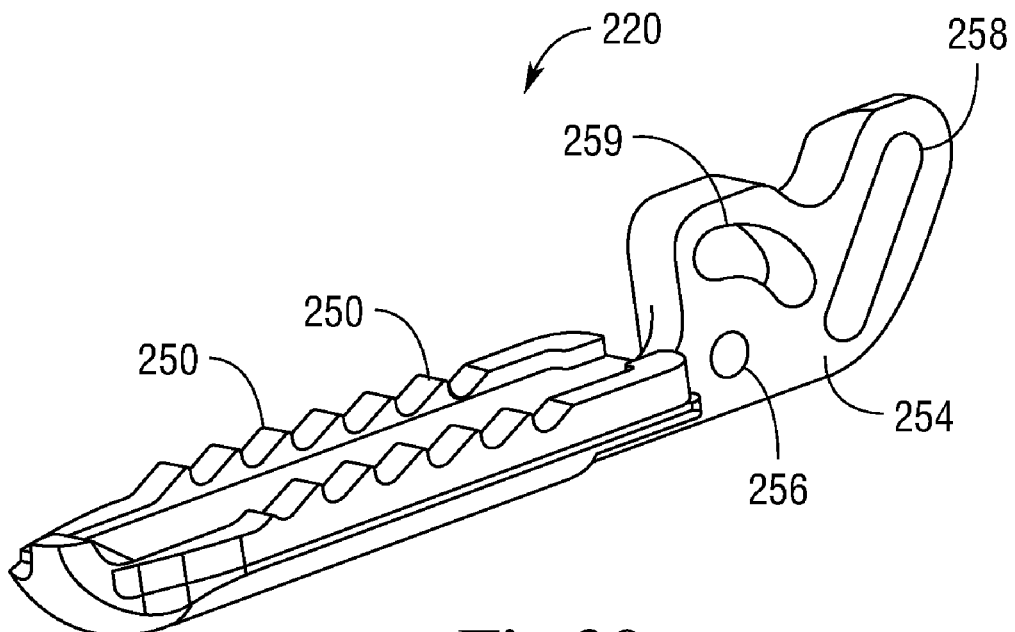
FIG. 20 illustrates one embodiment of a bottom jaw of the surgical grasping device shown in FIG. 18.

FIG. 20 shows a perspective view of one embodiment of bottom jaw 220 of surgical device 210. Bottom jaw 220 may include a plurality of teeth 250. A rear fin 254 defines a hole 256, a first slot 258, and a second slot 259. Hole 256 is suitable to receive first jaw pin 260 (FIG. 17), and second slot 259 is suitable to receive second jaw pin 261 (FIG. 17). First slot 258 and second slot 259 may extend through rear fin 254 to create elongated openings or may only extend partially into fin 254 to create a groove or indention in rear fin 254. In various embodiments, one slot may extend through rear fin 254 while the other slot only extends partially through fin 254. First slot 258 and second slot 259 may be of any desired curved, arcuate, or generally linear profile. In some embodiments, slots 258, 259 may comprise any combination of curved, arcuate, or generally linear sections in order to achieve the desired functionality.

Figure 21:
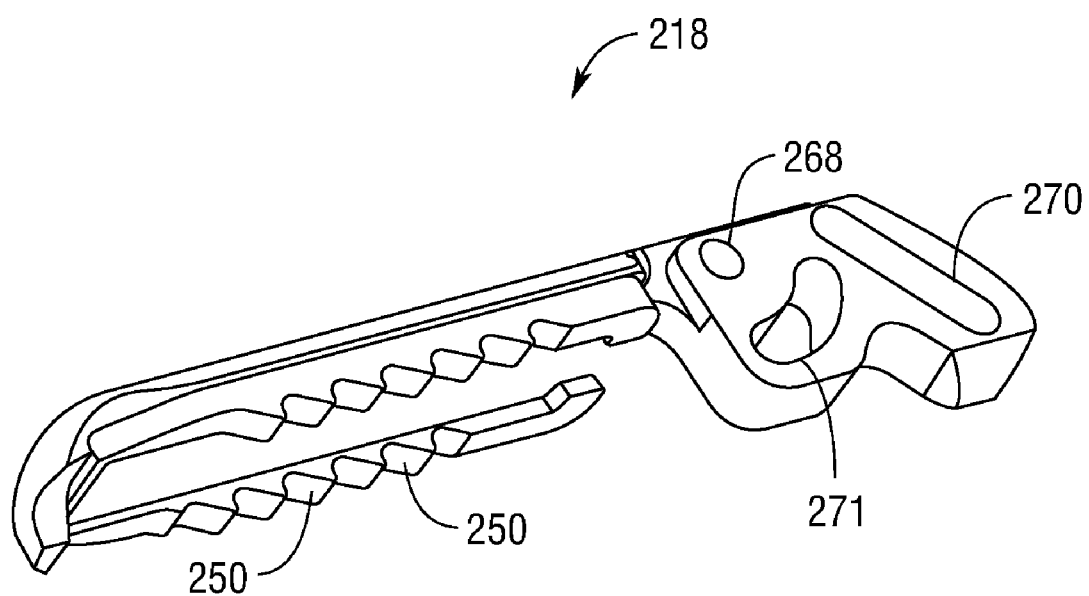
FIG. 21 illustrates one embodiment of a top jaw of the surgical grasping device shown in FIG. 18.

FIG. 21 shows a perspective view of top jaw 218 in accordance with various embodiments of the present invention. Top jaw 218 is constructed similarly to bottom jaw 220. Top jaw 218 may include a plurality of teeth 250. A rear fin 266 defines a hole 268 and may have a first slot 270 and a second slot 271. Hole 268 is suitable to receive second jaw pin 261 (FIG. 17), and second slot 271 is suitable to receive first jaw pin 260 (FIG. 17). First slot 270 and second slot 271 may extend through rear fin 266 to create elongated openings or may only extend partially into fin 266 to create a groove or indention in rear fin 266. In various embodiments, one slot may extend through rear fin 266, while the other slot only extends partially through rear fin 266. First slot 270 and second slot 271 may be of any desired curved, arcuate, or generally linear profile. In some embodiments, slots 270, 271 may comprise any combination of curved, arcuate, or generally linear sections in order to achieve the desired functionality.

Figure 22:
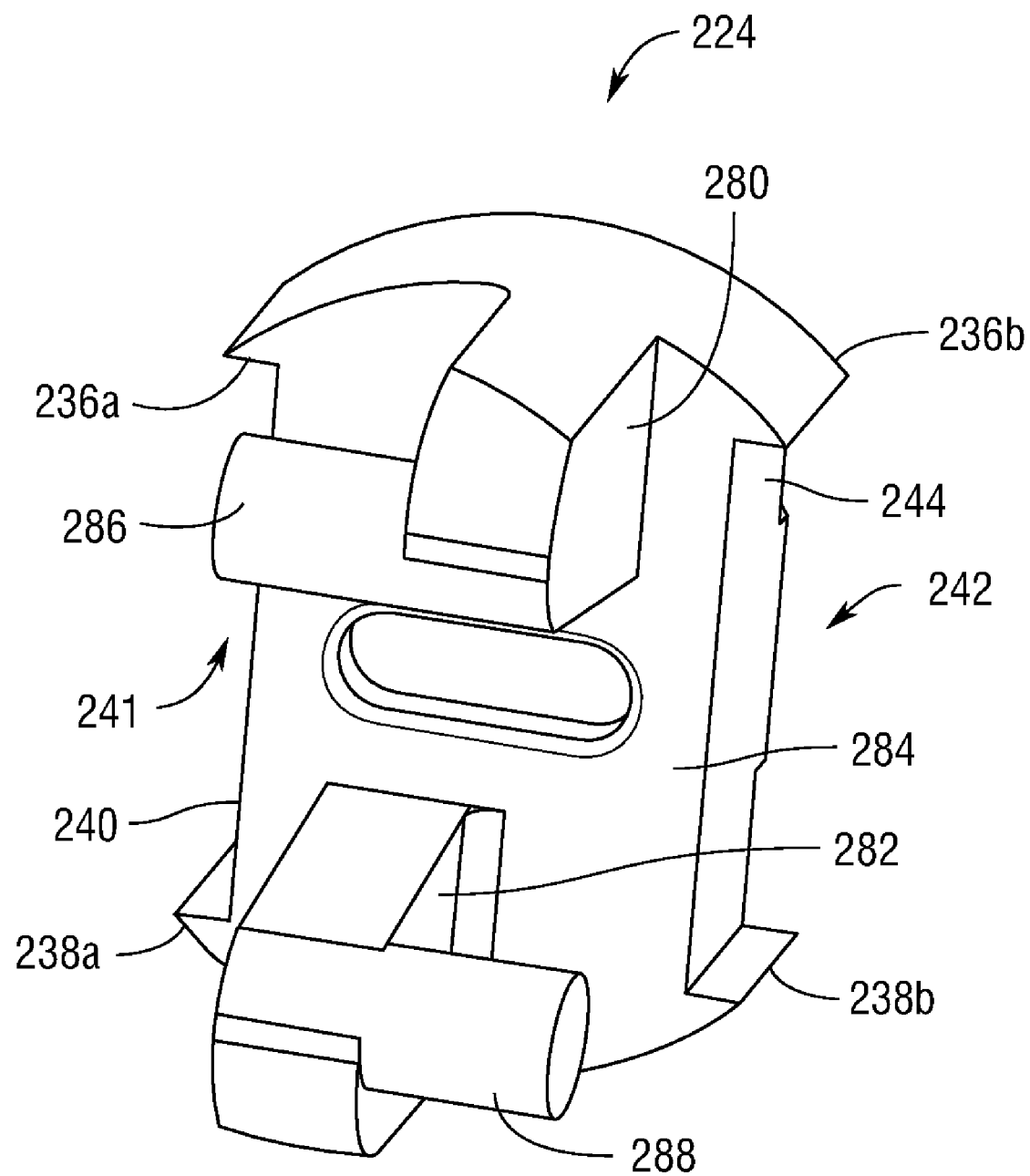
FIG. 22 illustrates one embodiment of a slider of the surgical grasping device shown in FIG. 18.

As shown in FIG. 22 slider 224 may have top flanges 236a, 236b and bottom flanges 238a, 238b extending from either side of slider 224. Top flange 236a and bottom flange 238a on first side 240 define a first channel 241 and top flange 236b and bottom flange 238b define a second channel 242 on second side 244. A top post 280 and a bottom post 282 may extend perpendicularly from a front face 284 of slider 224. In various embodiments, a top pin 286 may extend perpendicularly from top post 280, and a bottom pin 288 may extend perpendicularly from bottom post 282. In various embodiments, slider 224 is positioned in surgical device 210 such that clevis 226 is received by first channel 241 and second channel 242. As described in more detail below, slider 224 functions to slide in a longitudinal axis "C" (shown FIG. 17) along clevis 226. Top flanges 236a, 236b and bottom flanges 238a, 238b keep slider 224 generally affixed to clevis 226. Since driveline 232 is coupled to slider 224, the actuation of trigger 282 also serves to move slider 224. Therefore, movement of trigger 282 is translated into longitudinal movement of slider 224 along clevis 226.

Figure 23:
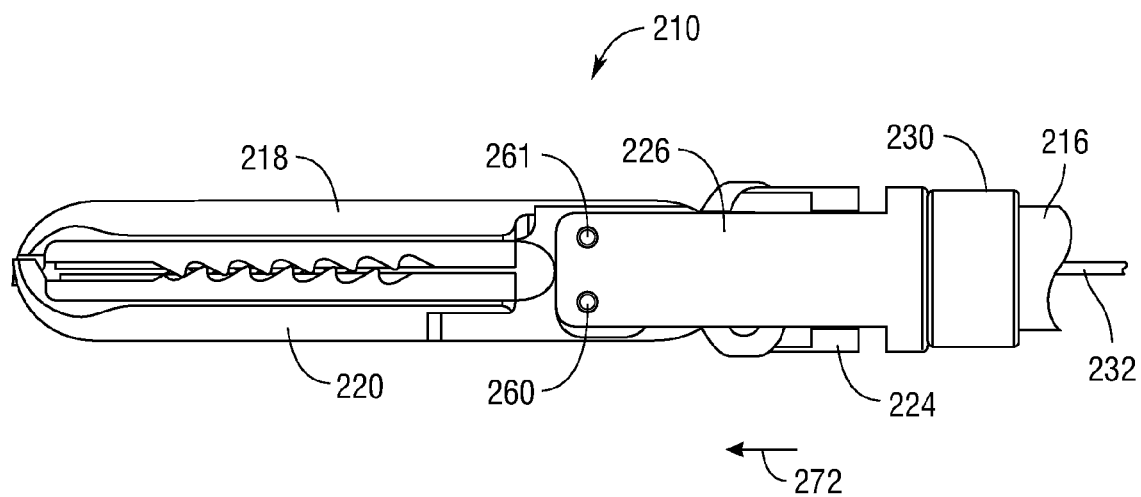
FIG. 23 is a side view of one embodiment of the surgical grasping device shown in FIG. 18.

FIG. 23 is a side view of one embodiment of surgical device 210. When assembled, in various embodiments, second jaw pin 261 is inserted through hole 268 of top jaw 218 and second slot 259 of bottom jaw 220. First jaw pin 260 is inserted into hole 256 of bottom jaw 220 and second slot 271 of top jaw 218. Rear fin 254 and rear fin 266 are positioned beside each other such that top pin 286 may be received by first slot 258 of bottom jaw 220 and bottom pin 288 may be received by first slot 270 of top jaw 218.

Figure 23A:
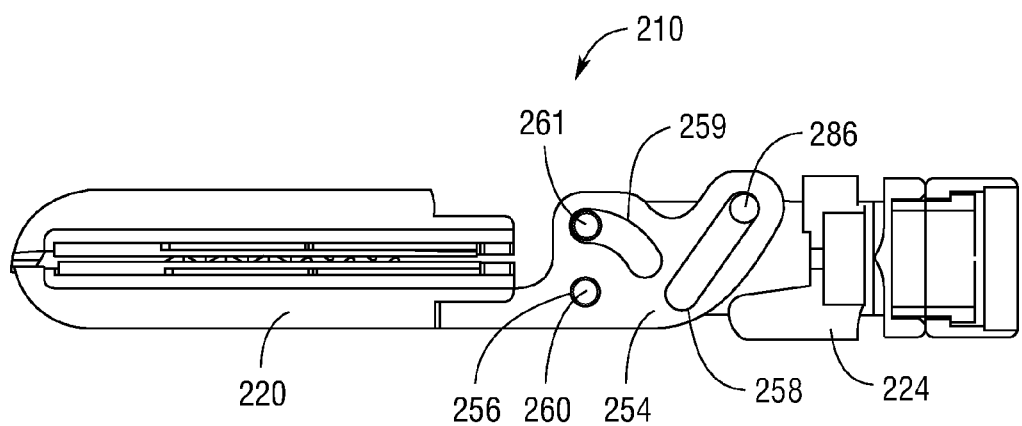
FIG. 23a is a cross-sectional perspective view of one embodiment of the surgical grasping device shown in FIG. 23 taken along the longitudinal axis.

FIGS. 23, 23a, 24, 24a, 25, and 25a demonstrate a progression of the actuation of surgical device 210. Referring first to FIG. 23 and FIG. 23a, a cross-sectional perspective view of one embodiment of surgical device 210 taken along the longitudinal axis of FIG. 23, surgical device 210 is shown in a "closed position." In its closed position, top jaw 218 and bottom jaw 220 are in close proximity to each other, allowing for the cutting, grasping, or ablating of tissue. In order to actuate, or open, top jaw 218 and bottom jaw 220, the user imparts movement to driveline 232. In various embodiments, trigger 282 may be used to impart such movement. Since slider 224 is coupled to driveline 232, movement of driveline 232 in a first direction 272 moves slider 224 longitudinally in first direction 272, or toward the distal end of surgical device 210.

Figure 24:
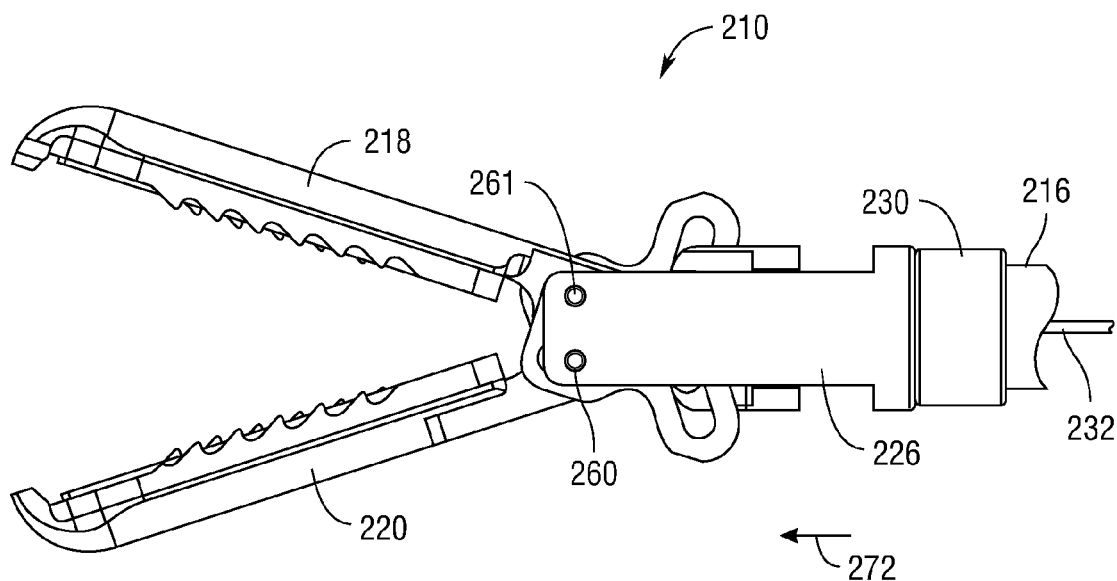
FIG. 24 is a side view of one embodiment of the surgical grasping device shown in FIG. 18 during actuation.
Figure 24A:
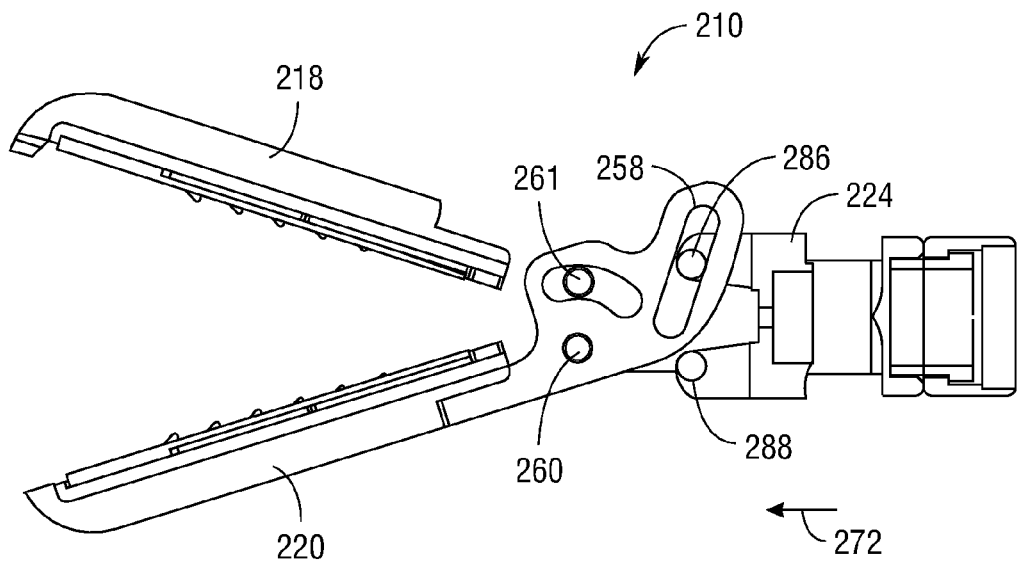
FIG. 24a is a cross-sectional perspective view of one embodiment of the surgical grasping device shown in FIG. 24 taken along the longitudinal axis.

FIG. 24 shows the position of top jaw 218 and bottom jaw 220 after slider 224 has moved in first direction 272. By virtue of the movement of driveline 232, slider 224 has been moved longitudinally along clevis 226. FIG. 24a is a cross-sectional view of one embodiment of surgical device 210 taken along the longitudinal axis of FIG. 24. Movement of slider 224 in first direction 272 moves top pin 286 and bottom pin 288 in first direction 272. This movement of top pin 286 and bottom pin 288 causes top pin 286 and bottom pin 288 to travel within first slot 258 and first slot 270, respectively. Additionally, second jaw pin 261 travels within second slot 259 and first jaw pin 260 travels within second slot 271 as top jaw 218 and bottom jaw 220 rotate with respect to each other. Due to the profile of first slots 258, 270, top jaw 218 and bottom jaw 220 pivot about jaw pins 260, 261 and pivotally separate from each other.

Figure 25A:
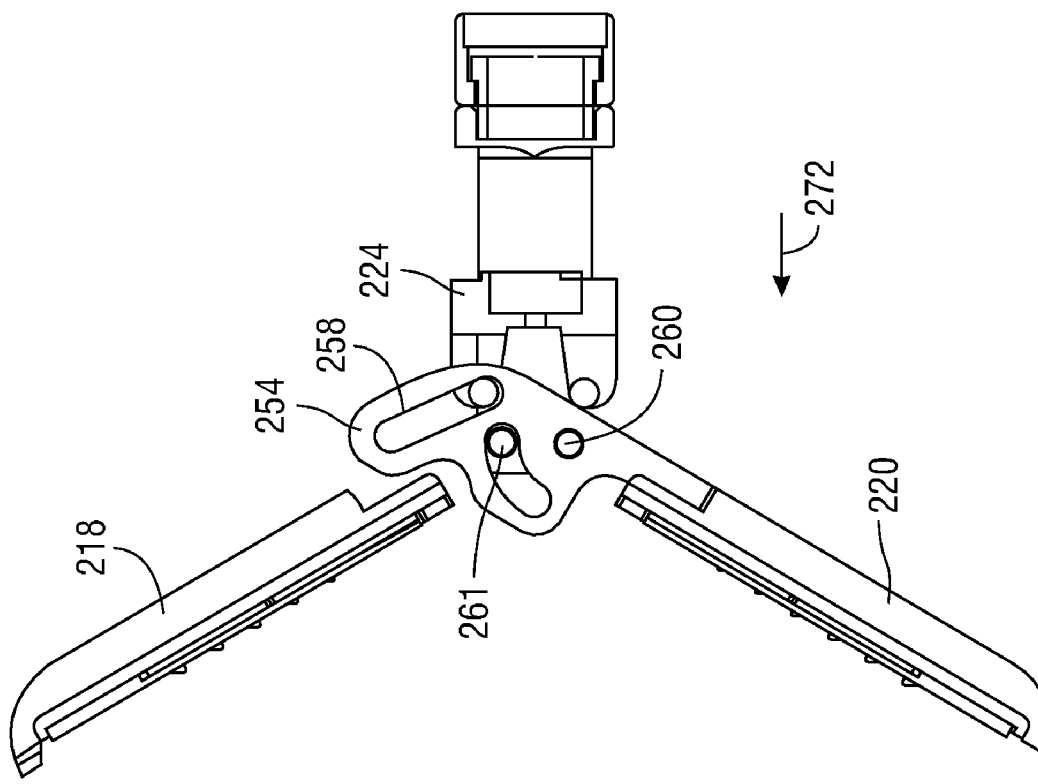
FIG. 25a is a cross-sectional perspective view of one embodiment of the surgical grasping device shown in FIG. 25 taken along the longitudinal axis.
Figure 25:
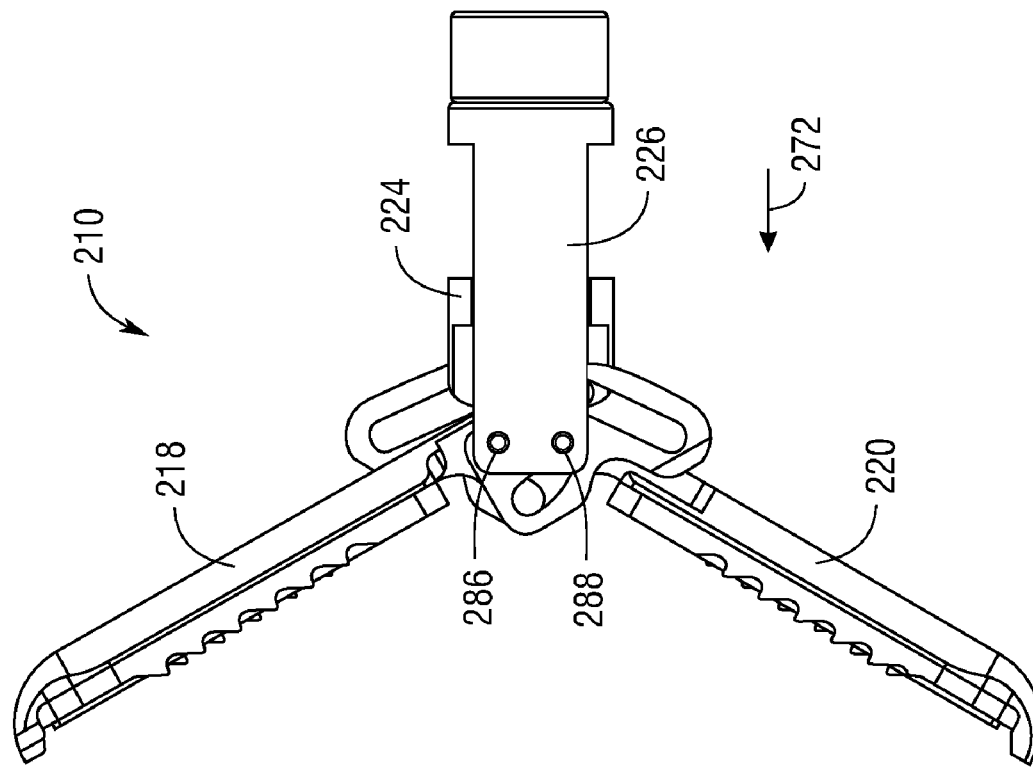
FIG. 25 is a side view of one embodiment of the surgical grasping device shown in FIG. 18 during actuation.

FIG. 25 shows the position of top jaw 218 and bottom jaw 220 after slider 224 has moved further in first direction 272. Slider 224 has been moved longitudinally further along clevis 226. FIG. 25a is a cross-sectional view of one embodiment of surgical device 210 taken along the longitudinal axis of FIG. 25. Due to the profile of slots 258, 270, top jaw 218 and bottom jaw 220 pivot about jaw pins 260, 261 and separate further from each other. As shown, top jaw 218 and bottom jaw 220 are nearly at a completely opened position. Furthermore, top pin 286 has traveled nearly the full length of first slot 258, and bottom pin 288 has traveled nearly the full length of first slot 270. Similarly, second jaw pin 261 has traveled nearly the full length of second slot 259, and first jaw pin 260 has traveled nearly the full length of second slot 271.

FIG. 26 shows an embodiment of surgical device 310. In various embodiments, surgical device 310 may have a top jaw 318 and a bottom jaw 320 pivotally coupled to a clevis 326. As illustrated, top jaw 318 may house a top electrode 322 and bottom jaw 320 may house a bottom electrode 328. A coupling 330 may allow for the attachment of clevis 26 to a shaft 316. In various embodiments coupling 330 may be optionally configured to allow the surgical device 310 to rotate relative to and about a longitudinal axis "D", thus allowing surgical device 310 to be positioned in multiple angular orientations. Some embodiments may have multiple couplings 330. Optionally, surgical device 310 may, for example, be attached to a laparoscopic and endoscopic instrument. Accordingly, in various embodiments, shaft 316 may be either flexible or rigid, or a combination thereof. A driveline 332 is located inside shaft 316. In various embodiments, driveline 332 passes through the center of coupling 330 and is attached to slider 324. Driveline 332 may be coupled to slider 324 using any suitable means, such as laser welding. Slider 324 functions to slide on longitudinal axis "D."

As shown in FIGS. 26a-b, surgical device 310 is configured for electrical therapy ablation, but in other embodiments may be configured for cutting, dissecting, or grasping. For example, top jaw 318 and bottom jaw 320 may be configured with cutting blades, a plurality of teeth, or any other configuration providing the required functionality. It is understood by those skilled in the art that surgical device 310 can be coupled to any control device, mechanical or electrical, which allows for actuation of top jaw 318 and bottom jaw 320, such as handle assembly 14 shown in FIG. 2.

FIG. 27a shows a perspective view of bottom jaw 320 of one embodiment of surgical device 310. Jaw may include a plurality of teeth (not shown). Jaw 320 also may house bottom electrode 328 and a bottom insulator 329. A rear fin 354 may define a first hole 356 and a second hole 358. First hole 356 and second hole 358 are suitable to receive a first jaw pin 360 and second jaw pin 361 (FIG. 26a). In various embodiments first jaw pin 360 may be unitary or integral with bottom jaw 320. Similarly, in various embodiments, embodiments second jaw pin 361 may be unitary or integral with bottom jaw 320. In the illustrated embodiment of bottom jaw 320 shown in FIG. 27b, rear fin 354 comprises a recessed section 355. Recessed section 355 may include a pin 357 protruding from the recessed section. In various embodiments, pin 357 may be unitary with rear fin 354 or, in various embodiments, pin 357 may be a member inserted into a hole.

FIG. 28a shows a perspective view of top jaw 318 of one embodiment of the surgical device 310. Top jaw 318 is constructed similarly to bottom jaw 320. Jaw 318 may include a plurality of teeth (not shown). Jaw 318 also may house top electrode 322 and a top insulator 323. A rear fin 366 may define a first hole 368 and a second hole 370. First hole 368 and second hole 370 are suitable to receive a first jaw pin 312 and a second jaw pin 314 (FIG. 26b). In various embodiments the jaw pins may be unitary or integral with bottom jaw 320. As shown in FIG. 28b, in various embodiments, top jaw 318 may comprise a pin 359 protruding from rear fin 366. In various embodiments, pin 359 may be unitary with rear fin 366 or, in various embodiments, pin 359 may be a member inserted into a hole.

As shown in FIGS. 29a-b, slider 324 may have top flanges 336a, 336b and bottom flanges 338a, 338b extending from either side of slider 324. Top flange 336a and bottom flange 338a on first side 340 define a first channel 341, and top flange 336b and bottom flange 338b define a second channel 342 on second side 344. First side 340 and second side 342 also may define a first hole 346 and second hole 348, respectively. First hole 346 and second hole 348 are suitable to receive a slider pin 347 and a slider pin 348, respectively (FIGS. 30a-b). In various embodiments, slider 324 may be positioned in surgical device 310 such that clevis 326 is received by first channel 341 and second channel 342. As described in more detail below, slider 324 functions to slide on longitudinal axis "D", as shown in FIG. 26, along clevis 326. Top flanges 336a, 336b and bottom flanges 338a, 338b keep slider 324 generally affixed to clevis 326 while allowing for axial movement. Since driveline 332 is coupled to slider 324, the actuation of trigger 82 also serves to move slider 324. Therefore, movement of trigger 82 (FIG. 2) is translated into longitudinal movement of slider 324 along clevis 326.

FIGS. 30a-c illustrate an embodiment of linkage 380. In various embodiments, linkage 380 may be comprised of a first link 382 and a second link 384. First link 382 may connect slider 324 to bottom jaw 320 and second link 384 may connect slider 324 to top jaw 318. In some embodiments, linkage 380 may comprise additional components. As shown in FIG. 30c first link 382 may define a first hole 386 and a second hole 388. Similarly, second link 384 may define a first hole 390 and a second hole 392. Links 382 and 384 may be any suitable shape. Examples of suitable shapes may include oblong, rectangular, or rod-like. In various embodiments slider pin 347 may be received in second hole 388 and slider pin 348 may be received by second hole 392. Pin 357 may be received by first hold 386 and pin 359 may be received by first hole 390.

FIGS. 31a-b illustrates a perspective view an embodiment of clevis 326 from two different angles. Clevis 326 has a distal end 400 and a proximal end 402. Proximal end 402 may be configured to couple to coupling 330. In various embodiments, distal end 400 might define a first hole 404 and a second hole 406. In various embodiments a pin (not shown) may be placed through first hole 404 and second 406 to reduce movement of first side 408 relative to second side 410 during operation of surgical device 310. Clevis 326 may have a first side 408 extending from proximal end 402 and a second side 410 extending from proximal end 402. In various embodiments, first side 408 and second side 410 may be substantially parallel. First side 408 may define a slot 412 and second side 410 may define a groove 414 for housing conductors.

Distal end of first side 408 may comprise a plurality of slots. In the illustrated embodiment, first side 408 comprises a first slot 416 and a second slot, comprised of first section 418a and second section 418b. An exemplary embodiment of first slot 416, first section 418a, and second section 418b are illustrated in FIG. 32a. The longitudinal axis "A1" of first section 418a may be substantially parallel to longitudinal axis "A2" of first slot 416. Axis A1 and A2 may in positioned in an angular relationship to longitudinal axis "E", the angular relationship identified by angle $\theta_1$. Second section 418b diverges from first section 418a at an angle $\theta_2$. In various embodiments, second section 418b may be curved. In some embodiments, second section 418b may have a curvature with a radius "r," which converges on a point 420. First jaw pin 360 may be configured to engage and travel along the path defined by first section 418a and second section 418b. Second jaw pin 361 may be configured to engage and travel along the path defined by first slot 416.

Distal end of second side 410 may comprise a plurality of slots. In the illustrated embodiment, second side 410 comprises a first slot 422 and a second slot, comprised of first section 424a and second section 424b. An exemplary embodiment of first slot 422, first section 424a, and second section 424b are illustrated in FIG. 32b. The longitudinal axis "B1" of first section 424a may be substantially parallel to longitudinal axis "B2" of first slot 422. Axis B1 and B2 may be positioned in an angular relationship to longitudinal axis "E", the angular relationship identified by angle $\theta_1$. Second section 424b diverges from first section 424a at an angle $\theta_2$. In various embodiments, section 424b may have a curvature with a radius "r," which converges on a point 426. Second jaw pin 314 may be configured to engage and travel along the patent defined by first section 424a and second section 424b. First jaw pin 312 may be configured to engage and travel along the path defined by first slot 422.

FIGS. 33-35 demonstrate a progression of the actuation of surgical device 310. Referring first to FIG. 33, surgical device 310 is shown in a "closed position." In its closed position, top jaw 318 and bottom jaw 320 are in close proximity to each other, allowing for the cutting, grasping, or ablating of tissue. In the illustrated embodiment, first jaw pin 360 and second jaw pin 361 are located near the proximal end of first section 418a and first slot 416, respectively. In order to actuate, or open, top jaw 318 and bottom jaw 320, the user may impart movement to driveline 332. In various embodiments, trigger 82 may be used to impart such movement. Since slider 324 is coupled to driveline 332, movement of driveline 232 in a first direction 372 moves slider 324 longitudinally in first direction 372, or toward the distal end of surgical device 310. FIG. 33a is a cross-sectional view of one embodiment of surgical device 310 taken along the longitudinal axis of FIG. 33.

FIG. 34 shows the position of top jaw 318 and bottom jaw 320 after slider 324 and linkage 380 have moved in first direction 372. By virtue of the movement of driveline 332, slider 324 has been moved longitudinally along clevis 326. Slider 324 may be coupled to first link 382 and a second link 384 which are coupled to top jaw 318 and bottom jaw 320, respectively. Thus, movement of slider 324 in first direction 372 moves first jaw pin 360 and second jaw pin 361 distally along the paths defined by first section 418a and first slot 416, respectively. Movement of slider 324 in first direction 372 also moves first jaw pin 312 and second jaw pin 314 distally along the paths defined by first slot 422 and first section 424a, respectively. Due to the profile of first section 418a, first slot 416, first slot 422, and 424a, top jaw 318 and bottom jaw 320 separate from each other in a direction indicated by arrows 429 while remaining substantially parallel. FIG. 34a is a cross-sectional view of one embodiment of surgical device 310 taken along the longitudinal axis of FIG. 34.

FIG. 35 shows the position of top jaw 318 and bottom jaw 320 after slider 324 and linkage 380 have moved further in first direction 372. Slider 324 has been moved longitudinally further along clevis 326. Due to the profile of first section 418a, first grove 416, first grove 422, and 424a, top jaw 318 and bottom jaw 320 separate further from each other in a direction indicated by arrows 429 while remaining substantially parallel. Furthermore, second jaw pin 361 has traveled nearly the full length of the path defined by first grove 416, and first jaw pin 360 has traveled nearly the full length of the path defined by first section 418a. Similarly, first jaw pin 312 has traveled nearly the full length of the path defined by first grove 422 and second jaw pin 314 has traveled nearly the full length of the path defined by first section 424a. FIG. 35a is a cross-sectional view of one embodiment of surgical device 310 taken along the longitudinal axis of FIG. 35.

FIG. 36 shows the position of top jaw 318 and bottom jaw 320 after slider 324 and linkage 380 have has moved further in first direction 372. Slider 324 has been moved longitudinally further along clevis 326. First jaw pin 360 is located in the path defined by second section 418b. Second jaw pin 314 is located in the path defined by second section 424b. As slider 324 is moved in first direction 372, first jaw pin 360 pivots about second jaw pin 361 and second jaw pin 314 pivots about first jaw pin 312. As first jaw pin 360 and second jaw pin 314 pivot, top jaw 318 and bottom jaw 320 angularly separate from each other the direction indicated by arrows 430. FIG. 36a is a cross-sectional view of one embodiment of surgical device 310 taken along the longitudinal axis of FIG. 36.

FIG. 37 shows the position of top jaw 318 and bottom jaw 320 after slider 324 and linkage 380 have has moved further in first direction 372. Slider 324 has been moved longitudinally further along clevis 326. First jaw pin 360 is located near the distal end of the path defined by second section 418b. Second jaw pin 314 is located near the distal end of the path defined by second section 424b. First jaw pin 360 has pivoted further about second jaw pin 361 and second jaw pin 314 has pivoted further about first jaw pin 312. Top jaw 318 and bottom jaw 320 have angularly separated further from each other the direction indicated by 430 to achieve a fully opened position. FIG. 37a is a cross-sectional view of one embodiment of surgical device 310 taken along the longitudinal axis of FIG. 37.

An exemplary procedure for use with surgical device 310 is illustrated in FIGS. 38-40. It will be appreciated by those skilled in the art that the methods described are also applicable to other embodiments or devices. After approaching an organ or tissue, such as artery 431, surgical device 310 is actuated to separate top jaw 318 and bottom jaw 320 so that the target, illustrated as artery 431, may be received between the jaw members (FIG. 38). Top jaw 318 and bottom jaw 320 are then "closed" to clamp artery 431 between top electrode 322 and bottom electrode 328. As top jaw 318 and bottom jaw 320 close in direction 432, they change from having an angular relationship (FIG. 38) to having a substantially parallel relationship (FIG. 39). Thus, top jaw 318 and bottom jaw 320 are able to engage artery 430 while in a substantially parallel position. As shown, the artery may be clamped by top jaw 318 and bottom jaw 320 to enable good contact with the ablation surfaces and an even distribution of electrical energy. Clamping also helps to remove blood from the tissue.

As appreciate by those skilled in the art, the pivoting configuration of top jaw 318 and bottom jaw 320 allows for a top electrode 322 and bottom electrode 328 to be in a parallel arrangement, even if the top jaw 318 and bottom jaw 320 are not in a fully "closed" position. Ablation energy is more effectively delivered to tissue if top electrode 322 and bottom electrode 328 are in a parallel arrangement. Thus, surgical device 310 can grip tissue and deliver energy to the tissue while the electrodes are in a parallel arrangement, even though the top jaw 318 and bottom jaw 320 are separated from each other. After energy has been delivered to the top electrode 322 and bottom electrode 328 by any suitable technique, top jaw 318 and bottom jaw 320 of surgical device 310 may be opened and removed from the ablation sight 434 of artery 431.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by the cleaning or replacement of particular pieces, and subsequent reassembly. In particular, the device can be disassembled, and any number of the particular pieces or parts of the device can be selectively replaced or removed in any combination. Upon the cleaning and/or replacement of particular parts, the device can be reassembled for subsequent use either at a reconditioning facility or by a surgical team immediately prior to a surgical procedure. Those skilled in the art will appreciate that the reconditioning of a device can utilize a variety of techniques for disassembly, cleaning/replacement, and reassembly. The use of such techniques, and the resulting reconditioned device, are all within the scope of the present application.

Preferably, the various embodiments described herein will be processed before surgery. First, a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that the device is sterilized. This can be done by any number of ways known to those skilled in the art, including beta or gamma radiation, ethylene oxide, or steam.

Although the various embodiments have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modifications and variations.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical device comprising:
   a clevis defining a longitudinal axis, wherein the clevis comprises a first prong and a second prong;
   a jaw comprising a first member and a second member, wherein the first member comprises a first slot, a third slot, and a first member pin, wherein the second member comprises a second slot, a fourth slot, and a second member pin, wherein the first member pin is receivably engaged in the second slot, and wherein the second member pin is receivably engaged in the first slot; and
   a slider slidably engaged to the clevis, the slider comprising:
      a first channel on a first lateral side of the clevis;
      a second channel on a second lateral side of the clevis, wherein the first channel is configured to receive a portion of the first prong of the clevis and the second channel is configured to receive a portion of the second prong of the clevis, and wherein the first and second prongs of the clevis guide longitudinal movement of the slider therebetween; and
      a plurality of slider pins, wherein each slider pin of the plurality of slider pins is receiveably engaged in one of the third slot and the fourth slot, wherein the jaw is selectively moveable between a first position and a second position through longitudinal movement of the slider, and wherein the surgical device is dimensioned to be inserted through a working channel of an endoscope.

2. The surgical device of claim 1, wherein the jaw comprises a cutting element.

3. The surgical device of claim 1, wherein the first fourth slot and the third slot are linear.

4. The surgical device of claim 1, wherein the first slot and the second slot are non-linear.

5. The surgical device of claim 1, wherein a driveline is coupled to the slider.

6. The surgical device of claim 5, comprising:
   a handle portion to receive a proximal end of the driveline;
   a trigger operatively coupled to the driveline;
   wherein the trigger is pivotally moveable in a first rotational direction to move the driveline in the first direction to open the jaw; and
   wherein the trigger is pivotally moved in a second rotational direction to move the driveline in the second direction to close the jaw.

7. A surgical device comprising:
   a clevis defining a longitudinal axis, wherein the clevis comprises a first clevis side and a second clevis side;
   a jaw comprising a first member and a second member, the first member defining a first slot and a third slot and the second member defining a second slot and a fourth slot; and
   a slider slidably engaged to the clevis, the slider comprising:
      a first channel on a first lateral side of the slider, wherein the first channel is configured to receive the first clevis side;
      a second channel on a second lateral side of the slider, wherein the second channel is configured to receive the second clevis side, and wherein the first and second clevis sides guide longitudinal movement of the slider therebetween;
      a first pin; and
      a second pin, wherein the first pin is receiveably engaged in the third slot, wherein the second pin is receivably engaged in the fourth slot, and wherein the jaw is selectively moveable between a first position and a second position through longitudinal movement of the slider, wherein the surgical device is dimensioned to be inserted through a working channel of an endoscope.

8. The surgical device of claim 7, comprising:
   a driveline coupled to the slider;
   a handle portion to receive a proximal end of the driveline;
   a trigger operatively coupled to the driveline; and
   wherein the trigger is pivotally moveable in a first rotational direction to move the driveline in the first direction to open the jaw; and is pivotally moved in a second rotational direction to move the driveline in the second direction to close the jaw.

9. The surgical device of claim 8, wherein the slider is moved in a direction toward the distal end of the surgical device to open the jaw and the slider is moved in a direction toward the proximal end of the surgical device to close the jaw.

10. The surgical device of claim 9, wherein the first slot is non-linear.

11. The surgical device of claim 10, wherein the second slot is non-linear.

12. A surgical device comprising:
    a clevis defining a longitudinal axis, wherein the clevis comprises a first pronged portion and a second pronged portion;
    a jaw comprising a first member and a second member, wherein the first member comprises a first slot and a third slot, and wherein the second member comprises a second slot and a fourth slot;
    a slider slidably engaged to the clevis, the slider comprising:

a first channel and a second channel, wherein the first channel is positioned on a first lateral side of the clevis and is configured to receive the first pronged portion, wherein the second channel is positioned on a second lateral side of the clevis and is configured to receive the second pronged portion, and wherein the first and second pronged portions of the clevis guide longitudinal movement of the slider therebetween; and a first pin and a second pin, wherein the third slot of the first member receives the first pin, and wherein the fourth slot of the second member receives the second pin;

a driveline coupled to the slider, wherein the jaw is selectively moveable between a first position and a second position through longitudinal movement of the driveline;

a handle portion to receive a proximal end of the driveline;

a trigger operatively coupled to the driveline;

wherein the trigger is pivotally moveable in a first rotational direction to move the driveline in the first direction to open the jaw; and wherein the trigger is pivotally moved in a second rotational direction to move the driveline in the second direction to close the jaw.

13. The surgical device of claim 12, wherein first and second electrode portions are coupled to the first member and a second member, and wherein the first and second electrode portions are adapted to receive an electrical waveform.

14. The surgical device of claim 13, wherein an electrical waveform generator is coupled to the first and second electrode portions and the first and second electrode portions are adapted to receive an electrical waveform.

15. The surgical device of claim 14, wherein the first slot is non-linear.

16. The surgical device of claim 15, wherein the second slot is non-linear.

17. A surgical instrument comprising:
a housing, the housing dimensioned to be inserted through a working channel of an endoscope, wherein the housing comprises a longitudinal axis, a first slot, a second slot, a third slot, and a fourth slot, wherein the first, second, third, and fourth slots are elongate in the direction of the longitudinal axis, and a portion of the first slot is parallel to a portion of the second slot and wherein a portion of the third slot is parallel to a portion of the fourth slot; and a jaw comprising a first member, a second member, and an electrode, the jaw pivotally connected to the housing, wherein the first jaw comprises a first pivot pin and a second pivot pin and wherein the second jaw comprises a third pivot pin and fourth pivot pin, wherein the first pin is received by the first slot, the second pin is received by the second slot, the third pin is received by the third slot, and the fourth pin is received by the fourth slot, wherein the jaw is selectively movable between a first position, a second position, and a third position, wherein the first member and second member are substantially parallel in the first position and substantially parallel in the second position, and wherein the first member and second member are configured in an angular relation in the third position.

18. The surgical instrument of claim 17, further comprising an actuator, wherein the first member and the second member are operably engaged with the actuator such that, when the actuator is moved relative to the housing, the first jaw member and the second jaw member are moved between the first, second, and third positions.

19. The surgical instrument of claim 18, wherein the jaw further comprises a second electrode.

20. The surgical instrument of claim 19, further comprising a switch, wherein the switch is selectively operable to place at least one of the first electrode and the second electrode in electrical communication with an electric current source.

21. The surgical instrument of claim 20, wherein the first slot has a curved portion and the third slot has a curved portion.

22. The surgical instrument of claim 21, wherein the first jaw and the second jaw are in the third position when the first pin is located in the curved portion of the first slot and the third pin is in the curved portion of the third slot.

23. The surgical instrument of claim 17, wherein the first position is a closed position, and wherein the third position is an open position.

24. A surgical instrument, comprising:
a hand piece;
a shaft;
a housing dimensioned to be inserted through a working channel of an endoscope wherein the housing comprises a longitudinal axis, a first slot, a second slot, a third slot, and a fourth slot, wherein the first, second, third, and fourth slots are elongate in the direction of the longitudinal axis; and a grasping device pivotally connected to the housing, comprising:
a first jaw including a first electrode, a first pin, and a second pin, wherein the first slot receives the first pin and the second slot receives the second pin;
a second jaw including a second electrode, a third pin, and a fourth pin, wherein the third slot receives the third pin and the fourth slot receives the fourth pin, wherein the second jaw is selectively movable between an angular open position, a parallel open position, and a parallel closed position.

25. The surgical instrument of claim 24, further comprising an actuator, wherein the first jaw member and the second jaw member are operably engaged with the actuator such that, when the actuator is moved relative to the shaft, the first jaw member and the second jaw member are pivoted between the angular open position, the parallel open position, and the parallel closed position.

26. The surgical instrument of claim 25, wherein the shaft is a flexible shaft.

* * * * *